US012774305B2

(12) United States Patent
Wirtz et al.

(10) Patent No.: US 12,774,305 B2
(45) Date of Patent: Oct. 27, 2026

(54) CYCLIC COMPOUNDS, METHOD FOR THEIR PREPARATION AND THE USE OF SAID CYCLIC COMPOUNDS IN COSMETIC PREPARATIONS

(71) Applicant: EBERHARD KARLS UNIVERSITAET TUEBINGEN, Tuebingen (DE)

(72) Inventors: Sebastian N Wirtz, Tuebingen (DE); Stephanie Grond, Tuebingen (DE); Julian S Saur, Tuebingen (DE); Bernhard Krismer, Kirchentellinsfurt (DE); Andrea Heuer, Kutenholz (DE); Jennifer Huepeden, Hamburg (DE)

(73) Assignee: EBERHARD KARLS UNIVERSITAET TUEBINGEN, Tuebingen (DE)

( * ) Notice: Subject to any disclaimer, the term of this patent is extended or adjusted under 35 U.S.C. 154(b) by 580 days.

(21) Appl. No.: 18/036,269

(22) PCT Filed: Nov. 20, 2021

(86) PCT No.: PCT/EP2021/082388

§ 371 (c)(1),
(2) Date: May 10, 2023

(87) PCT Pub. No.: WO2022/106667

PCT Pub. Date: May 27, 2022

(65) Prior Publication Data

US 2025/0282825 A1 Sep. 11, 2025

(30) Foreign Application Priority Data

Nov. 20, 2020 (EP) .................................... 20208947

(51) Int. Cl.
*C07K 7/56* (2006.01)
*A61K 8/64* (2006.01)
*A61Q 19/00* (2006.01)

(52) U.S. Cl.
CPC .................. *C07K 7/56* (2013.01); *A61K 8/64* (2013.01); *A61Q 19/00* (2013.01); *A61K 2800/74* (2013.01); *A61K 2800/805* (2013.01)

(58) Field of Classification Search
CPC ........................................................ C07K 7/56
See application file for complete search history.

(56) References Cited

U.S. PATENT DOCUMENTS

| | | | |
|---|---|---|---|
| 5,116,824 | A | 5/1992 | Miyata et al. |
| 5,166,187 | A | 11/1992 | Collombel et al. |
| 5,658,331 | A | 8/1997 | Della Valle et al. |
| 6,541,023 | B1 | 4/2003 | Andre et al. |
| 8,518,422 | B2 | 8/2013 | Monks et al. |
| 9,364,413 | B2 | 6/2016 | Lu et al. |
| 11,219,585 | B2 | 1/2022 | Stangl et al. |
| 2005/0249691 | A1 | 11/2005 | Monks et al. |
| 2016/0256379 | A1 | 9/2016 | Stangl et al. |
| 2018/0155397 | A1 | 6/2018 | Krismer et al. |

FOREIGN PATENT DOCUMENTS

| | | | |
|---|---|---|---|
| EP | 0296078 | B1 | 5/1991 |
| EP | 0462426 | B1 | 8/1997 |
| EP | 2340856 | B1 | 12/2014 |
| EP | 3062763 | B1 | 12/2017 |
| EP | 3072899 | B1 | 5/2018 |
| WO | 2009124754 | A1 | 10/2009 |
| WO | 2015062727 | A1 | 5/2015 |
| WO | 2019149450 | A1 | 8/2019 |

OTHER PUBLICATIONS

US 5,808,050 A, 09/1998, Mares-Guia (withdrawn)

Malins, et al. (Journal of the American Chemical Society (abstract), 2017, 139(14), 5233-5241; retrieved from CAPLUS, Accession No. 2017:476613).*

Schilling N A et al. "Synthetic Lugdunin Analogues Reveal Essential Structural Motifs for Antimicrobial Action and Proton Translocation Capability", vol. 58, No. 27, May 27, 2019 (May 27, 2019), pp. 9234-9238, Angewandte Chemie International Edition.

Malins L Ret al. "Peptide Macrocyclization Inspired by Non-Ribosomal Imine Natural 1-3,11-13 Products", vol. 139, No. 14, Apr. 12, 2017 (Apr. 12, 2017), pp. 5233-5241, Journal of the American Chemical Society.

Michinori Tanaka et al. "A Novel Oxazolidine Linker for the Synthesis of Peptide Aldehydes" International Journal of Peptide Research and Therapeutics, vol. 13, No. 1-2, Feb. 3, 2007 (Feb. 3, 2007), pp. 271-279.

Campiglia P et al. "Design and Synthesis of Small Libraries of Peptidomimetics Based 4-7.11 on a Thiazolidine Moiety" Letters in Organic Chemistry, vol. 3, No. 7, Jul. 1, 2006 (Jul. 1, 2006), pp. 539-545.

Lubell W D et al. "Configurational stability of N-protected .alpha.-amino aldehydes" Journal of the American Chemical Society, vol. 109, No. 1, Jan. 1, 1987 (Jan. 1, 1987), pp. 236-239.

Saur J S et al. "Distinct Lugdunins from a New Efficient Synthesis and Broad Exploitation 1-14 of Its MRSA-Antimicrobial Structure" , vol. 64, No. 7, Mar. 29, 2021 (Mar. 29, 2021), pp. 4034-4058, Journal of Medicinal Chemistry.

(Continued)

*Primary Examiner* — Shawquia Jackson

(74) *Attorney, Agent, or Firm* — Abel Schillinger, LLP

(57) ABSTRACT

The present invention relates to novel cyclic compounds; a method for the solid phase synthesis of said novel cyclic compounds; novel thiazolidine and oxazolidine building blocks that can be directly incorporated into the solid phase synthesis of said novel cyclic compounds, and a novel method for the synthesis of said thiazolidine and oxazolidine building blocks; and cosmetic compositions containing said novel cyclic compounds.

11 Claims, 36 Drawing Sheets

(56) References Cited

OTHER PUBLICATIONS

Myers, et al.; "Synthesis of highly epimerizable N-protected-amino aldehydes of high enantiomeric excess," Tetrahedron Letters 41 (2000) 1359-1362.

Meyer, et al.; "Acceleration of the Dess-Martin Oxidation by Water," J. Org. Chem. 1994, 59, 7549-7552.

Bitschar, et al.; "Lugdunin amplifies innate immuno responses in skin in synergy with host- and microbiota-derived factors", Nature Communications (2019)10: 2730 https://doi.org/10.1038/541467-019-10646-7.

* cited by examiner

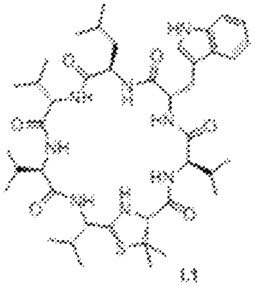

1.1

Chemical sum formula: C[illegible]H[illegible]N[illegible]O[illegible]S
Exact molecular weight: 811.1000

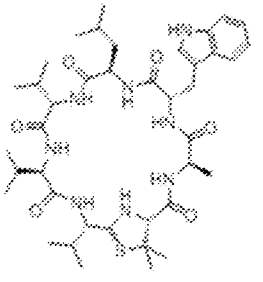

1.2

Chemical sum formula: C[illegible]H[illegible]N[illegible]O[illegible]S
Exact molecular weight: 783.0460

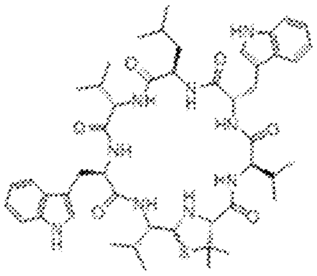

1.3

Chemical sum formula: C[illegible]H[illegible]N[illegible]O[illegible]S
Exact molecular weight: 898.1810

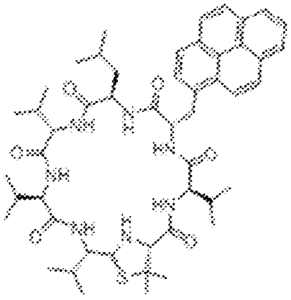

1.4

Chemical sum formula: C[illegible]H[illegible]N[illegible]O[illegible]S
Exact molecular weight: 896.2050

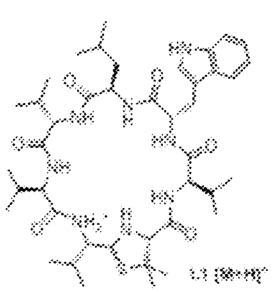

1.1 $[M+H]^+$

Chemical sum formula: C[illegible]H[illegible]N[illegible]O[illegible]$S^+$
Exact molecular weight: 811.4899

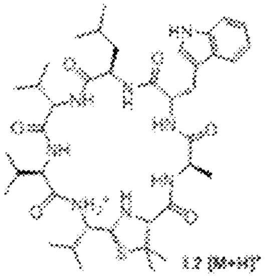

1.2 $[M+H]^+$

Chemical sum formula: C[illegible]H[illegible]N[illegible]O[illegible]$S^+$
Exact molecular weight: 783.4586

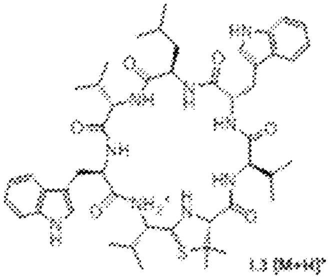

1.3 $[M+H]^+$

Chemical sum formula: C[illegible]H[illegible]N[illegible]O[illegible]$S^+$
Exact molecular weight: 898.5008

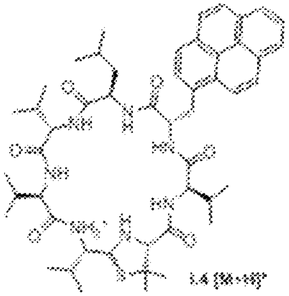

1.4 $[M+H]^+$

Chemical sum formula: C[illegible]H[illegible]N[illegible]O[illegible]$S^+$
Exact molecular weight: 896.5103

FIG. 1A

I.19

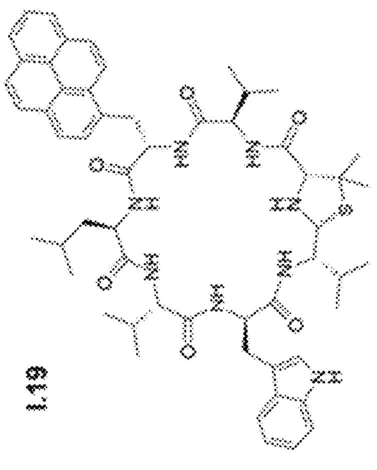

Chemical sum formula C[illegible]H[illegible]N[illegible]O[illegible]S
Exact molecular weight 983.2860

I.20

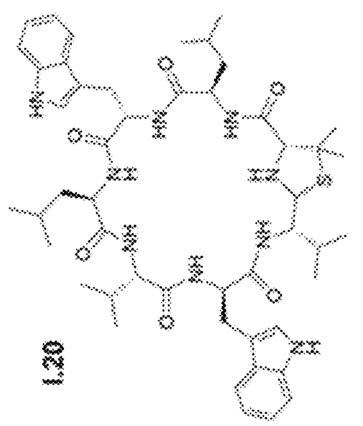

Chemical sum formula C[illegible]H[illegible]N[illegible]O[illegible]S
Exact molecular weight 912.2080

I.21

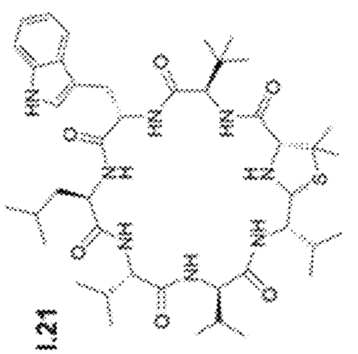

Chemical sum formula C[illegible]H[illegible]N[illegible]O[illegible]S
Exact molecular weight 825.1270

I.19
[M+H]$^+$

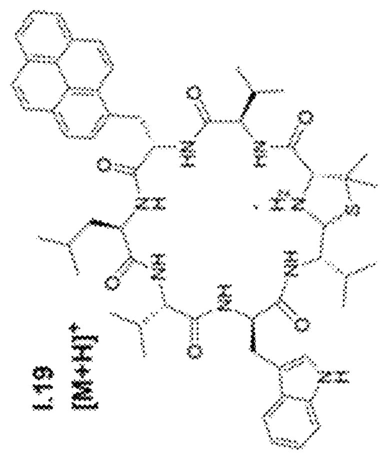

Chemical sum formula C[illegible]H[illegible]N[illegible]O[illegible]S$^+$
Exact molecular weight 984.2935

I.20
[M+H]$^+$

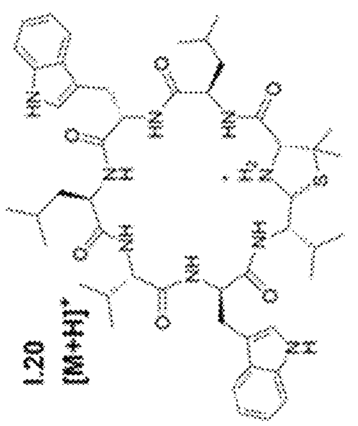

Chemical sum formula C[illegible]H[illegible]N[illegible]O[illegible]S$^+$
Exact molecular weight 913.2155

I.21
[M+H]$^+$

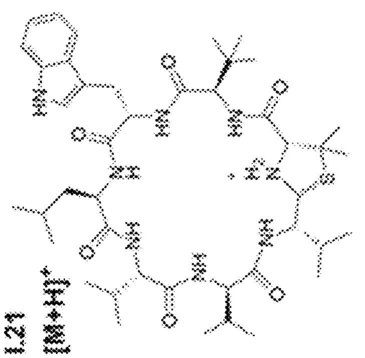

Chemical sum formula C[illegible]H[illegible]N[illegible]O[illegible]S$^+$
Exact molecular weight 826.1345

FIG. 1B

Chemical sum formula: $C_{42}H_{66}N_{8}O_{6}S$
Exact molecular weight: 811.1000

I.23

Chemical sum formula: $C_{48}H_{67}N_{9}O_{6}S$
Exact molecular weight: 898.1810

I.24

Chemical sum formula: $C_{48}H_{63}N_{9}O_{6}S$
Exact molecular weight: 894.1490

I.22
[M+H]+

Chemical sum formula: $C_{42}H_{67}N_{8}O_{6}S^{+}$
Exact molecular weight: 812.1075

I.23
[M+H]+

Chemical sum formula: $C_{48}H_{68}N_{9}O_{6}S^{+}$
Exact molecular weight: 899.1885

I.24
[M+H]+

Chemical sum formula: $C_{48}H_{64}N_{9}O_{6}S^{+}$
Exact molecular weight: 895.1565

| Cyclic compound | Final test concentrations of the cyclic compounds (µg·mL⁻¹ or µM, respectively) | | | | | | | | | | |
|---|---|---|---|---|---|---|---|---|---|---|---|
| | 100 | 50 | 25 | 12.5 | 6.3 | 3.1 | 1.6 | 0.8 | 0.4 | 0.2 | 0 |
| **Stock solution** | $OD_{600}$ cell density of *Staphylococcus aureus* USA300 LAC | | | | | | | | | | |
| **I.1** (mg·mL⁻¹) | 0.058 | 0.04 | 0.027 | 0.023 | 0.233 | 1.155 | 1.605 | 1.428 | 1.474 | 1.494 | 1.524 |
| **I.1** (mM) | 0.005 | -0.01 | -0.013 | -0.017 | 0.177 | 1.227 | 1.454 | 1.489 | 1.479 | 1.585 | 1.603 |
| | | | | | | | | | | | |
| **I.2** (mg·mL⁻¹) | 0.01 | -0.02 | 0.091 | 0.758 | 1.488 | 1.548 | 1.592 | 1.577 | 1.629 | 1.594 | 1.587 |
| **I.2** (mM) | 0.00098 | -0.02 | 0.502 | 0.883 | 1.542 | 1.55 | 1.548 | 1.498 | 1.533 | 1.601 | 1.504 |
| | | | | | | | | | | | |
| **I.3** (mg·mL⁻¹) | 0.055 | -0.003 | -0.004 | -0.012 | -0.013 | 0.107 | 1.277 | 1.478 | 1.512 | 1.492 | 1.643 |
| **I.3** (mM) | 0.005 | -0.001 | -0.008 | -0.015 | -0.016 | 0.27 | 1.326 | 1.469 | 1.464 | 1.504 | 1.611 |
| | | | | | | | | | | | |
| **I.4** (mg·mL⁻¹) | 0.019 | 0.011 | 0.008 | 0.006 | 0.03 | 0.128 | 0.628 | 0.683 | 0.738 | 0.718 | 0.723 |
| **I.4** (mM) | 0.036 | 0.029 | 0.015 | 0.009 | 0.02 | 0.216 | 0.644 | 0.679 | 0.7 | 0.725 | 0.696 |
| | | | | | | | | | | | |
| **Neg. control** | | | | | | | | | | | |
| **DMSO** (mg·mL⁻¹) | 1.532 | 1.533 | 1.499 | 1.509 | 1.527 | 1.527 | 1.494 | 1.517 | 1.52 | 1.5 | 1.545 |

FIG. 2A

| Cyclic compound | Final test concentrations of the cyclic compounds (µg·mL⁻¹ or µM, respectively) | | | | | | | | | | |
|---|---|---|---|---|---|---|---|---|---|---|---|
| | 100 | 50 | 25 | 12.5 | 6.25 | 3.125 | 1.563 | 0.781 | 0.391 | 0.195 | 0 |
| **Stock solution** | $OD_{600}$ cell density of *Staphylococcus aureus* USA300 LAC | | | | | | | | | | |
| **I.19** (mg·mL⁻¹) | 0.087 | 0.389 | 0.437 | 0.462 | 0.52 | 0.613 | 0.632 | 0.658 | 0.671 | 0.722 | 0.737 |
| **I.19** (mM) | 0.354 | 0.442 | 0.437 | 0.438 | 0.547 | 0.529 | 0.588 | 0.611 | 0.64 | 0.68 | 0.694 |
| **I.20** (mg·mL⁻¹) | 0.021 | -0.006 | -0.011 | -0.018 | -0.019 | -0.003 | 0.539 | 0.588 | 0.588 | 0.602 | 0.63 |
| **I.20** (mM) | -0.011 | -0.011 | -0.021 | -0.023 | -0.022 | -0.006 | 0.536 | 0.598 | 0.618 | 0.613 | 0.631 |
| **I.21** (mg·mL⁻¹) | -0.005 | -0.011 | -0.014 | -0.014 | 0.016 | 0.101 | 0.991 | 1.018 | 0.989 | 0.973 | 1.004 |
| **I.21** (mM) | -0.012 | -0.012 | -0.013 | -0.015 | 0.026 | 0.13 | 0.969 | 0.99 | 0.974 | 0.974 | 0.973 |
| **I.22** (mg·mL⁻¹) | 0.000375 | -0.004 | -0.012 | -0.014 | 0.605 | 0.85 | 0.908 | 0.933 | 0.931 | 1.003 | 0.979 |
| **I.22** (mM) | -0.006 | -0.013 | -0.017 | -0.018 | 0.584 | 0.873 | 0.846 | 0.951 | 0.924 | 0.947 | 0.945 |
| **I.23** (mg·mL⁻¹) | 0.111 | 0.065 | 0.418 | 0.882 | 0.744 | 0.79 | 0.931 | 0.924 | 0.81 | 0.916 | 0.893 |
| **I.23** (mM) | 0.141 | 0.106 | 0.898 | 1.22 | 1.08 | 0.99 | 0.92 | 0.975 | 0.939 | 1.039 | 0.993 |
| **I.24** (mg·mL⁻¹) | 0.003 | 0.002 | -0.006 | -0.008 | 0.513 | 0.991 | 0.992 | 0.988 | 0.963 | 0.949 | 0.976 |
| **I.24** (mM) | -0.004 | -0.002 | -0.006 | -0.011 | 0.294 | 0.919 | 1.001 | 0.962 | 0.964 | 0.934 | 0.973 |
| **Neg. control** | | | | | | | | | | | |
| **DMSO** (mg·mL⁻¹) | 0.642 | 0.615 | 0.664 | 0.662 | 0.672 | 0.654 | 0.668 | 0.692 | 0.697 | 0.698 | 0.692 |

FIG. 2B

Isomer I

Isomer II

Isomer I

Isomer II

Isomer I

Isomer II

Isomer II

Isomer I

CYCLIC COMPOUNDS, METHOD FOR THEIR PREPARATION AND THE USE OF SAID CYCLIC COMPOUNDS IN COSMETIC PREPARATIONS

The present invention relates to novel cyclic compounds; a method for solid-phase synthesis of said novel cyclic compounds; novel thiazolidine and oxazolidine building blocks that can be directly incorporated into the solid-phase synthesis of said novel cyclic compounds, and a novel method for synthesis of said thiazolidine and oxazolidine building blocks; and the use of the cyclic compounds in cosmetic compositions.

BACKGROUND OF THE INVENTION

Blemished skin, acne and other skin phenomena, conditions and disorders that are amenable to treatment with cosmetic preparations affect the well-being of affected persons, even in mild cases. Virtually everyone is affected by such skin phenomena, conditions or disorders at some time. In many cases, these can be treated with cosmetic preparations without the need for pharmaceutical preparations with strong pharmaceutical active ingredients, which have side effects and can thus have negative consequences for the person being treated.

Such pharmaceutical preparations with highly potent pharmaceutical active ingredients are usually not suitable for cosmetic use, since for the patient treated with such pharmaceutical preparations, negative effects or consequences may often occur in some way, e.g. at the systemic level, especially in the metabolic functions of the body, when they are used.

Peptides and peptide derivatives in unicellular up to complex multicellular organisms such as humans have an important signaling function and coordinate many biochemical processes, with the respective functions being defined in each case by the specific structure of a peptide or peptide derivative. Because of this structure-specific functional diversity, they represent promising components of preparations, especially in the cosmetics industry, where there is a constant search for novel compounds that can embellish the skin to improve general well-being.

Peptides and peptide derivatives have long been used in cosmetic preparations. For example, EP 0 296 078, EP 0 462 426, EP 2340856 and U.S. Pat. Nos. 5,116,824, 6,541,023 and 5,808,050 disclose cosmetic preparations comprising chitosans, collagens and glycosylaminoglycans. EP 3,062, 763 discloses cosmetic preparation comprising glycoprotein 1 and 2.

Certain cyclic peptides and peptide derivatives with specific structural features are proposed in the prior art for use in cosmetic preparations, for example, to maintain or improve the general condition of the skin or hair, as anti-aging and for reducing the appearance of wrinkles.

WO 2009/124754 discloses, for example, the use of certain cyclic peptides in topical, cosmetic and/or personal care compositions having improved handling properties, improved stability properties and/or advantageous integrin-modulating activity, for the care, maintenance or improvement of the general condition of the skin or hair and for prophylaxis against time and/or light-related aging processes of human skin or human hair, as well as for prophylaxis and/or treatment of skin diseases associated with defective keratinization related to differentiation and cell proliferation.

U.S. Pat. No. 9,364,413 B2 discloses the use of the cycloaliphatic heptapeptide surfactin in cosmetic compositions as an anti-aging, anti-wrinkle and skin penetration enhancer.

WO 2019/149450 A1 discloses the use of certain cyclic peptides of at least five amino acids, including at least one proline (Pro) and at least two phenylalanines (Phe), as active components in a non-therapeutic peptide-based cosmetic treatment of the skin and/or its appendages. These cyclic peptides are to improve the density and thickness of the dermis, reduce the appearance of wrinkles, maintain the flexibility of the epidermis, reduce the pore size of the skin, reduce the unpleasant sensation of sensitive skin and of redness, and limit the deterioration of the quality of the supporting tissue and the premature aging of the skin.

Cyclic peptide derivatives comprising, for example, five to seven amino acids or amino acid derivatives and a thiazolidine, oxazolidine or imidazolidine ring are described in patent specification EP 3 072 899. In particular, EP 3 072 899 describes the finding and isolation of the bactericidal peptide anti-infective lugdunin comprising six amino acids and a thiazolidine ring, in *S. lugdunensis*. Bitschar et al, Nat. Commun. 2019 06 21; 10(1):2730 also describes that lugdunin may provide a potentially three-tiered protection against *S. aureus* in host skin. First, it may act as a bactericide, for example, in synergy with the human antimicrobial peptides DCD-1(L) and LL-37 to kill *S. aureus*; second, lugdunin may enhance the commensal-induced innate immune response in primary human keratinocytes; and third, lugdunin-induced recruitment of phagocytotic cells could potentially contribute to effective killing of *S. aureus*.

It is an object of the present invention to provide a novel, simplified method which allows for preparing novel compounds in a simple fashion and with high purity via chemical solid phase synthesis.

In view of the above, it is an object of the present invention to provide said novel compounds in the non-therapeutic treatment of cosmetic or dermatological phenomena.

SUMMARY OF THE INVENTION

The present inventors have now discovered novel cyclic compounds which, surprisingly, are suitable for use in cosmetic preparations due to their advantageous properties. The novel cyclic compounds according to the invention combine a number of advantageous properties.

In particular, the cyclic compounds according to the invention preferably exhibit antimicrobial, in particular antiviral, antibacterial and/or antifungal, preferably antiviral and/or (non-selective) antibacterial, activity in cosmetic use. For example, it was surprisingly found that the cyclic compounds according to the invention exhibit non-selective antimicrobial, in particular non-selective antibacterial activity, preferably against Gram-positive bacteria. Preferably, on the other hand, the cyclic compounds according to the invention exhibit no or only minimal antibacterial activity against Gram-negative bacteria.

Furthermore, the novel cyclic compounds according to the invention exhibit a supportive effect on the innate immune response. For example, the novel cyclic compounds according to the invention are surprisingly particularly effective, in cosmetic use, in supporting the innate immune response of the skin against infections with microorganisms, such as bacteria. The cyclic compounds according to the invention are thus, for example, excellently suited for use as cosmetic active ingredients for non-therapeutic use in cosmetic preparations, in particular for topical application.

In addition, it was surprisingly found that the non-selectively antibacterially active cyclic compounds according to the invention when used do not lead to any, or only to an extremely small extent to formation of resistance; the cyclic compounds according to the invention in particular, for example, do not exhibit any relevant formation of resistance, whereas the prior art compound lugdunin does, and thus there is a significant difference with respect to the formation of resistance. Surprisingly, it was found that the cyclic compounds according to the invention differ from the known compound lugdunine, for example, with respect to the mode of action.

The novel cyclic compounds according to the invention are characterized by excellent solubility and stability in common solvents and carriers, which favors their use especially in cosmetic preparations. Also, the novel cyclic compounds according to the invention are surprisingly not or not readily degraded by conventional proteases, which favors their use on the skin.

The present inventors have found a novel efficient chemical synthesis route using solid-phase peptide synthesis resin, which allows to synthesize the novel cyclic compounds with the mentioned advantageous properties easily and in high purity (>90% purity after optimized aqueous washing, but still before specific purification, for example, by preparative chromatography) and high yield, which was not possible so far. This novelly created synthesis route allows the production of the novel cyclic compounds according to the invention in commercially relevant quantities without difficulty, or, respectively, the simple upscaling of the synthesis method on an industrial scale to increase the synthesis performance.

The novel synthetic route according to the invention is based on the preparation of previously unknown alkyl, aryl, or alkynyl heterocycle amino acid derivatives, the novel thiazolidine and oxazolidine building blocks, necessary for step (i) or (ii). The novel thiazolidine and oxazolidine building blocks are particularly characterized by excellent solubility in organic solvents and superior coupling properties in solid phase synthesis associated therewith. Furthermore, the present inventors have developed a synthesis method for the novel thiazolidine and oxazolidine building blocks.

The synthesis of the thiazolidine and oxazolidine building blocks can thus be advantageously incorporated into the efficient method of solid-phase peptide synthesis for the first time. This allows a simple, controlled and highly efficient synthesis of the novel cyclic compounds, by solid-phase peptide synthesis via a linear precursor (i.e. via a linear peptide derivative bound to the solid phase), and easier upscaling. Following established principles, the linear precursor can finally be cyclized to the cyclic compound under optimized conditions in the final step and isolated in optimized washing steps with a high degree of purity (>90% purity).

Thus, to solve the above-mentioned problem, the present invention provides novel cyclic compounds as well as cosmetic, in particular topical, preparations containing the novel cyclic compounds as cosmetic active ingredients.

Furthermore, the present invention provides a novel chemical synthesis method in the form of a solid-phase peptide synthesis, which allows the novel cyclic compounds according to the invention to be prepared easily and in high purity. In connection with this novel synthesis method, there are also provided novel compounds in the form of thiazolidine and oxazolidine building blocks which, via a novel synthetic route, are advantageously incorporated directly into the novel solid-phase peptide synthesis method as a starting point for the synthesis of the novel cyclic compounds. The present invention relates to the objects defined in the following items 1 to 13:

[1]A cyclic compound of formula (I):

(I)

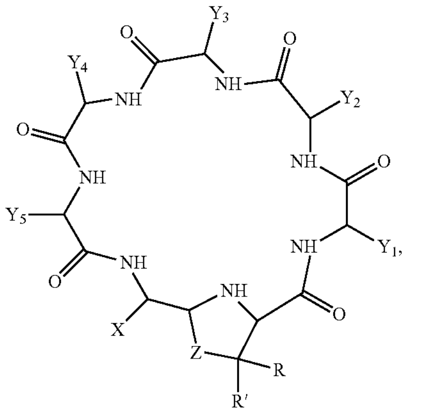

wherein:

X and $Y_1$ to $Y_5$ are each selected from the group consisting of: methyl, ethyl, n-propyl, 2-propenyl ($H_2C{=}CH{-}CH_2{-}$), 1-methylethyl, n-butyl, 2-methylpropyl, 1-methylpropyl, 1,1-dimethylethyl, n-pentyl, 3-methylbutyl, benzyl (Bn), propargyl ($HC{\equiv}C{-}CH_2{-}$), 1H-indole-3-ylmethyl ( 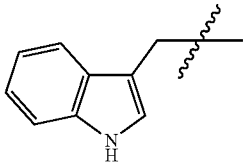 ), 1N-methyl-1H-indole-3-ylmethyl ( 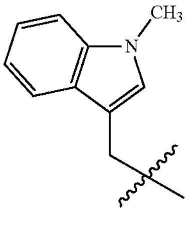 ), 3-benzothienylmethyl (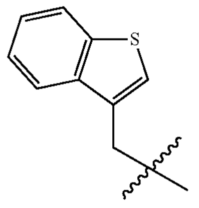), 1-naphthylmethyl (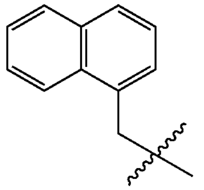), 9-anthracenylmethyl (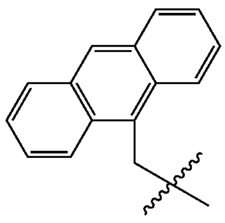)

and pyrenylmethyl;

Z is equal to O or S;

R and R' each are selected from the group consisting of H, methyl, ethyl, n-propyl, 1-methylethyl, n-butyl, 2-methylpropyl, 1-methylpropyl, benzyl and propargyl, with the proviso that when R is H, R' is not H;

the C atoms, which are directly linked to the substituents $Y_1$, $Y_2$, $Y_3$, $Y_4$, $Y_5$ and X, in this order, each have an alternating absolute stereochemical configuration; and the C atom, which is bound to substituent X, and the C atom in position 4 of the thiazolidine or oxazolidine ring have the same absolute stereochemical configuration when Z is O and an opposite absolute stereochemical configuration when Z is S;

with the proviso that when X, $Y_1$, $Y_4$ and $Y_5$ are 1-methylethyl, $Y_2$ is 1H-indole-3-ylmethyl, $Y_3$ is 2-methylpropyl, R is H and R' is methyl, Z is not O;

and the salts thereof, the solvates thereof, and the solvates of the salts thereof.

[2] The cyclic compound according to [1], wherein

R and R' are both methyl; $Y_2$ is 1H-indole-3-ylmethyl or pyrenylmethyl if $Y_5$ is 1-methylethyl, or $Y_2$ is 1-methylethyl, if $Y_5$ is 1H-indole-3-ylmethyl or pyrenylmethyl; and X is 1-methylethyl;

R is H; R' is methyl, ethyl, n-propyl, 1-methylethyl, benzyl or propargyl; $Y_2$ is 1H-indole-3-ylmethyl or pyrenylmethyl if $Y_5$ is 1-methylethyl, or $Y_2$ is 1-methylethyl if $Y_5$ is 1H-indole-3-ylmethyl or pyrenylmethyl; and X is 1-methylethyl;

R is H; R' is methyl, n-propyl, 1-methylethyl, benzyl or propargyl; $Y_2$ is 1H-indole-3-ylmethyl or pyrenylmethyl if $Y_5$ is 1-methylethyl, or $Y_2$ is 1-methylethyl if $Y_5$ is 1H-indole-3-ylmethyl or pyrenylmethyl; and X is 1-methylethyl or 2-methylpropyl; or R and R' are both 1-methylethyl; and $Y_2$ is 1H-indole-3-ylmethyl; and/or characterized by one of the following formulae:

I.1

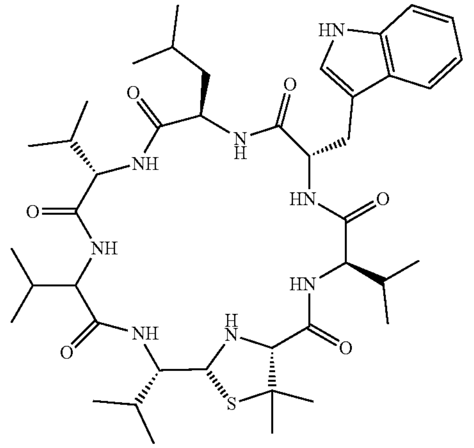

I.2

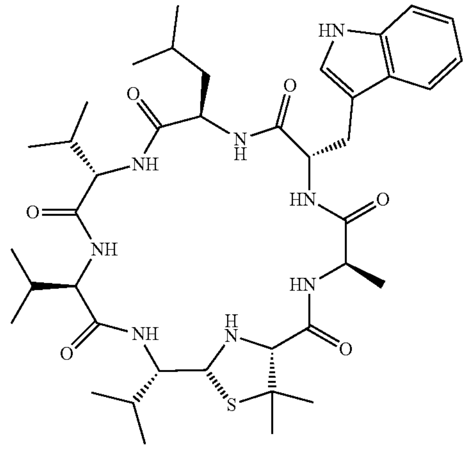

I.3

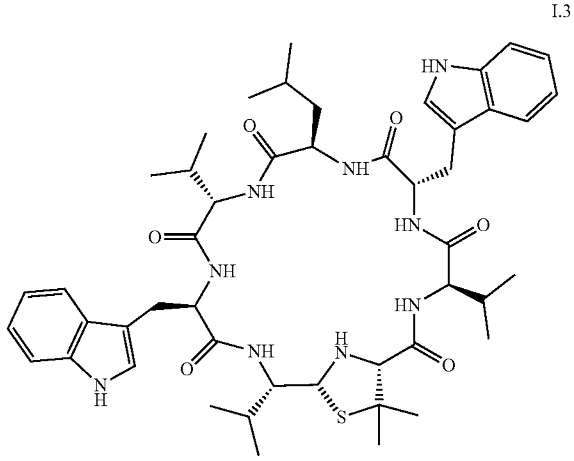

-continued
I.4
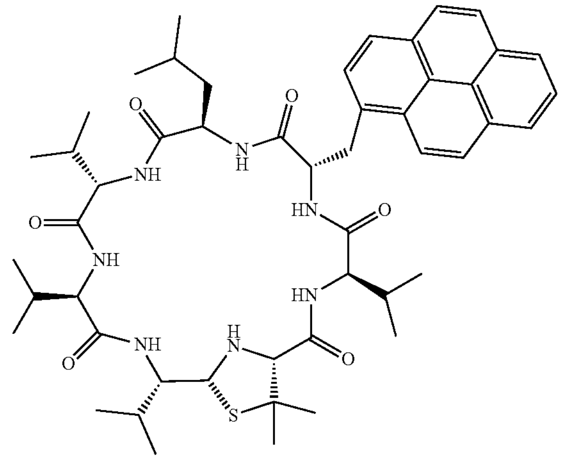
I.5
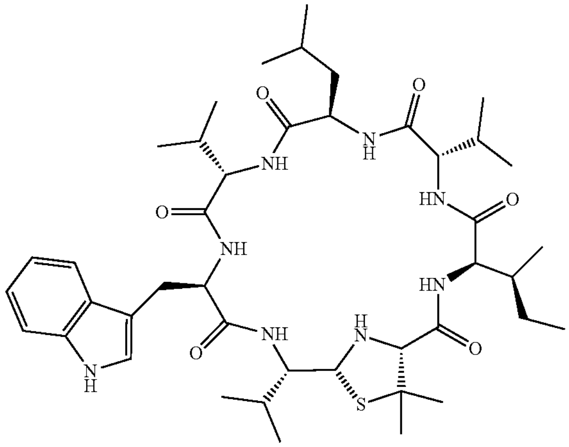
I.6
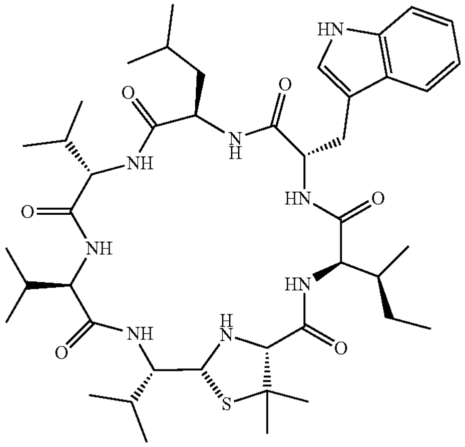
-continued
I.7
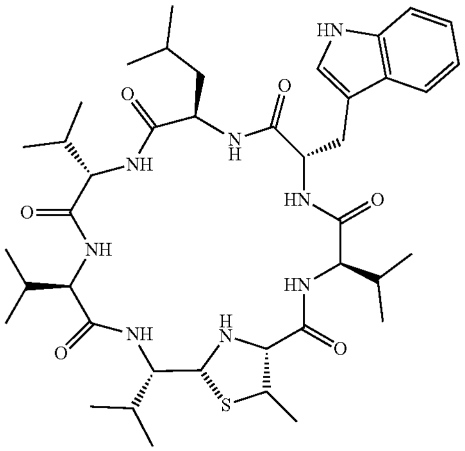
I.8
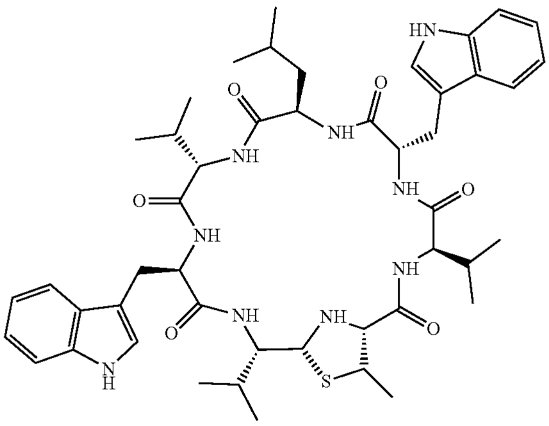
I.9
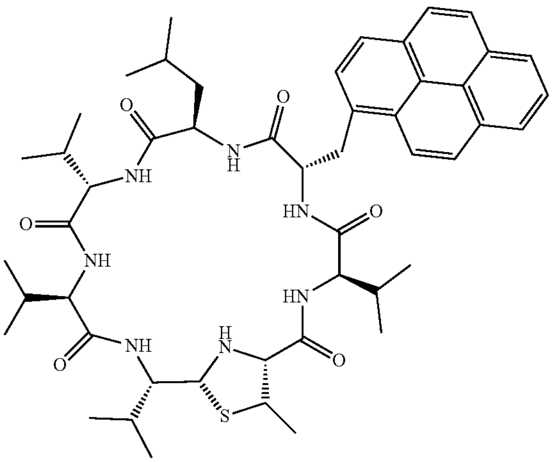

-continued
I.10
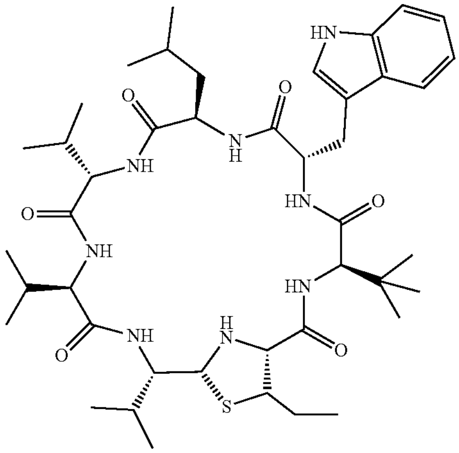
I.11
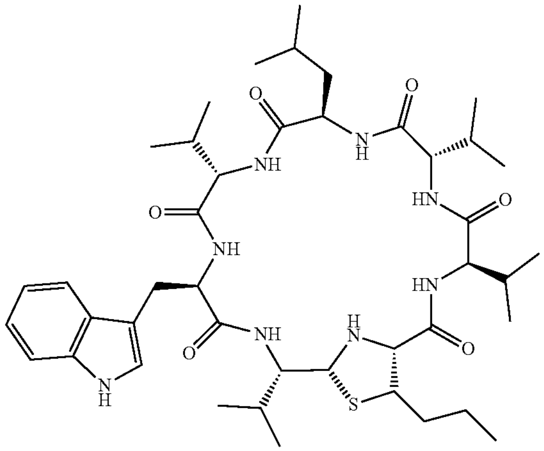
I.12
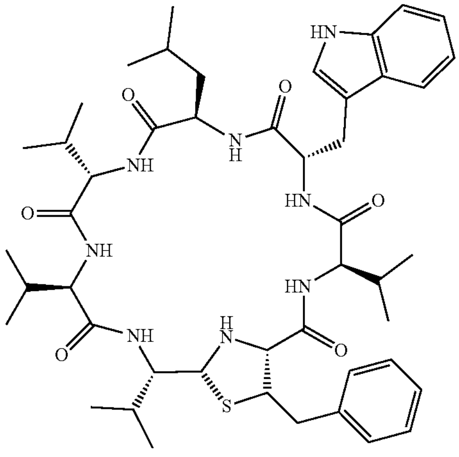
-continued
I.13
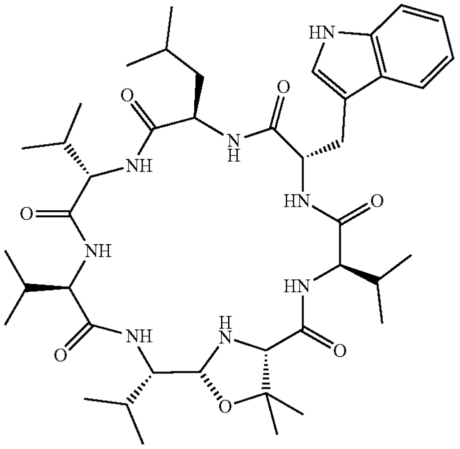
I.14
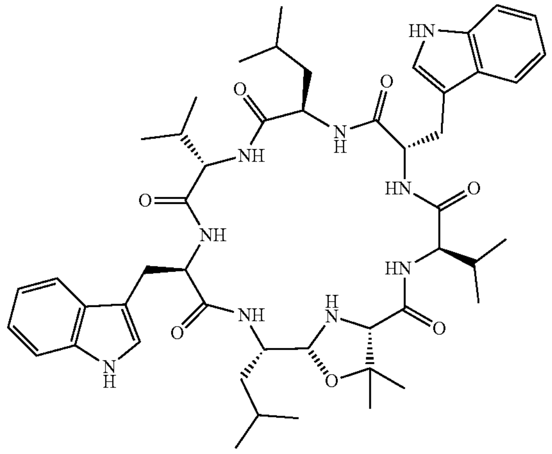
I.15
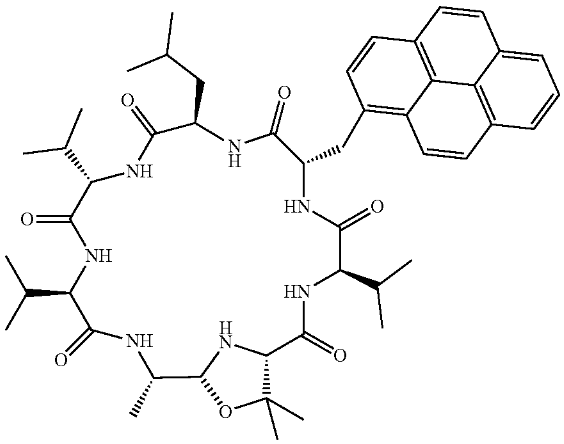

-continued
I.16
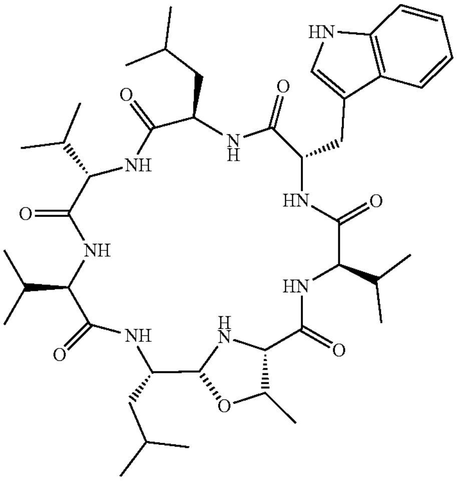
I.17
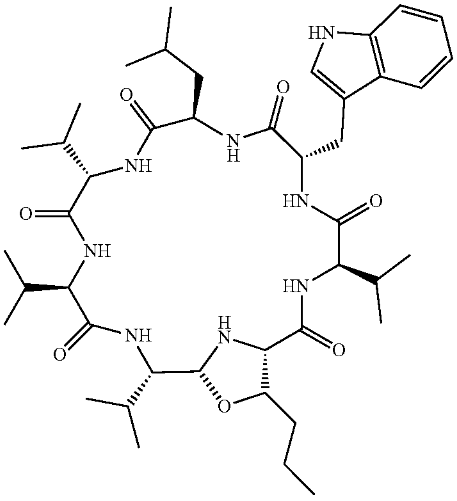
I.18
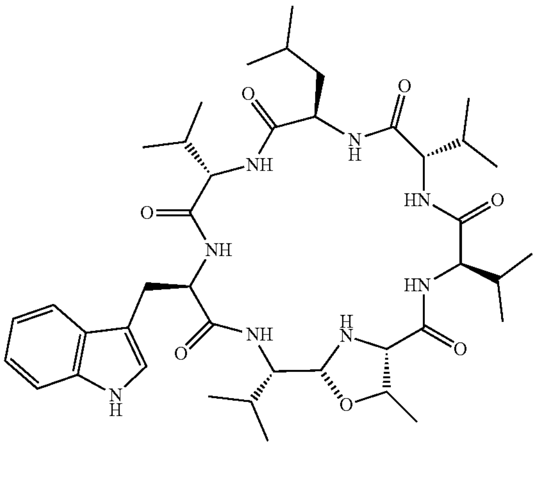
-continued
I.19
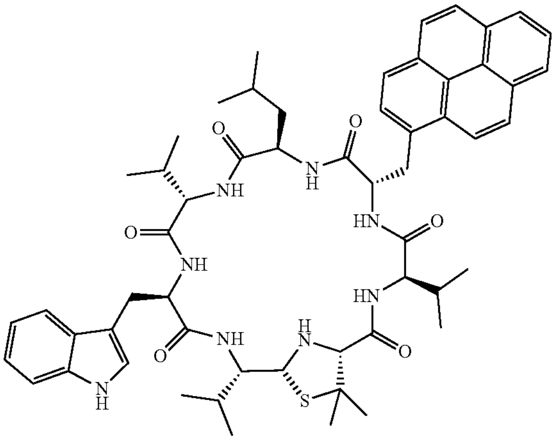
I.20
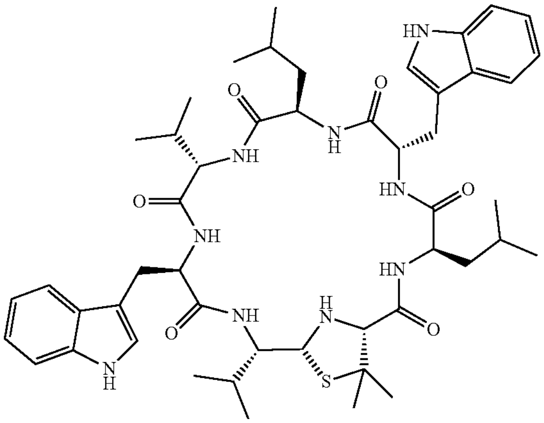
I.21
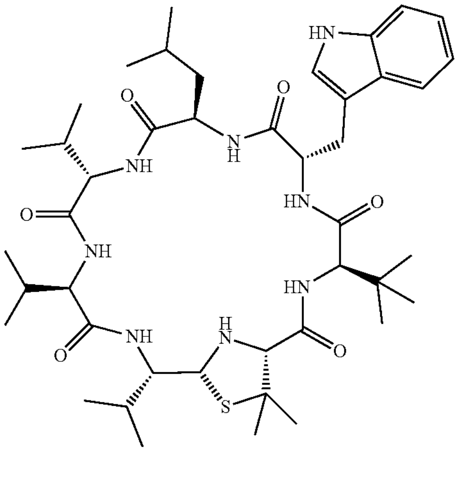

-continued

I.22

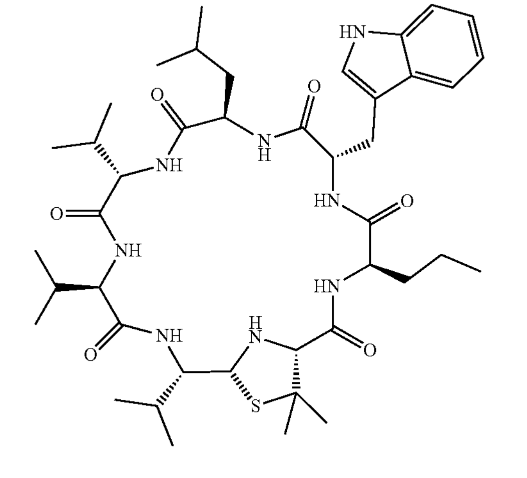

I.23

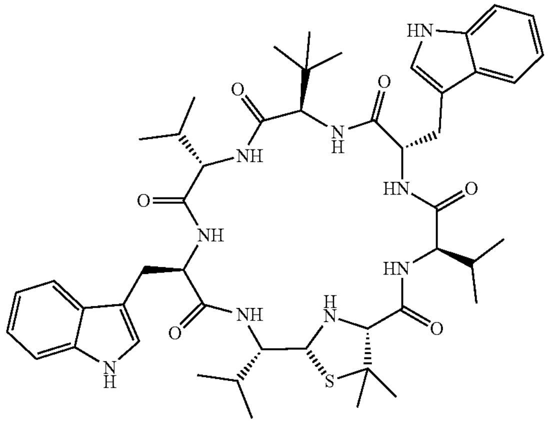

I.24

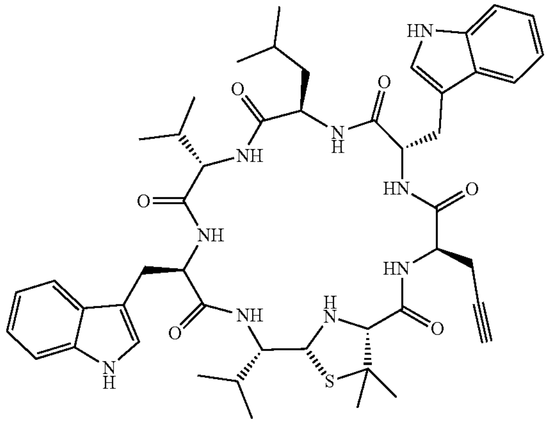

[3] Cyclic compound according to [1] or [2] with antimicrobial, in particular antiviral or non-selective antibacterial (preferably against Gram-positive bacteria, but preferably not or only minimally against Gram-negative bacteria), activity and/or supportive effect on the innate immune response, in particular of the skin.

[4] A thiazolidine or oxazolidine building block of formula (II):

(II)

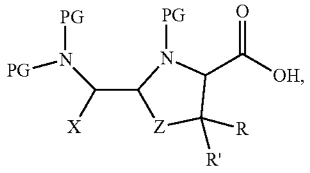

wherein:

Z is O or S;

R and R' each are selected from the group consisting of H, methyl, ethyl, n-propyl, 1-methylethyl, n-butyl, 2-methylpropyl, 1-methylpropyl, benzyl and propargyl, with the proviso that when R is H, R' is not H;

PG each represents H or a protecting group, wherein individual PG may be the same or different, and wherein the protecting group is preferably selected from the group consisting of 9-fluorenylmethoxycarbonyl (Fmoc), tert-butyloxycarbonyl (Boc), benzyloxycarbonyl (Cbz), benzyl (Bn), trityl (Trt), acetyl (Ac) and tosyl (Ts);

X is selected from the group consisting of: methyl, ethyl, n-propyl, 2-propenyl, 1-methylethyl, n-butyl, 2-methylpropyl, 1-methylpropyl, 1,1-dimethylethyl, n-pentyl, 3-methylbutyl, benzyl, propargyl, 1H-indole-3-ylmethyl, 1N-methyl-1H-indole-3-ylmethyl, 3-benzothienylmethyl, 1-naphthylmethyl, 9-anthracenylmethyl and pyrenylmethyl;

the C atom, which is bound to substituent X, and the C atom in position 4 of the thiazolidine or oxazolidine ring have the same absolute stereochemical configuration when Z is O and an opposite absolute stereochemical configuration when Z is S;

with the proviso that, when Z is equal to S and X is equal to methyl, benzyl or 1H-indole-3-ylmethyl, R is not methyl;

and the salts thereof, the solvates thereof, and the solvates of the salts thereof.

[5] Thiazolidine or oxazolidine building block according to [4], characterized by one of the following formulae:

(II.1)

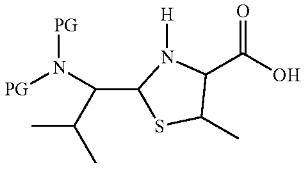

(II.2)

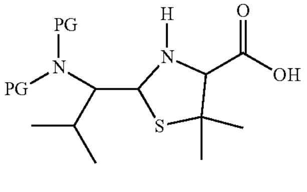

-continued
(II.3)
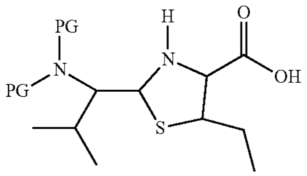
(II.4)
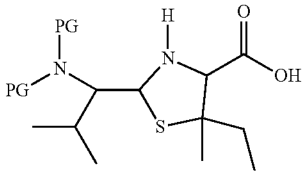
(II.5)
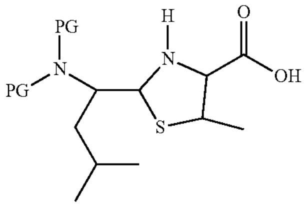
(II.6)
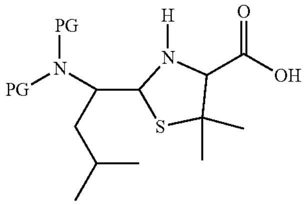
(II.7)
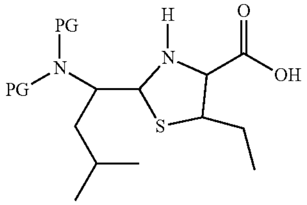
(II.8)
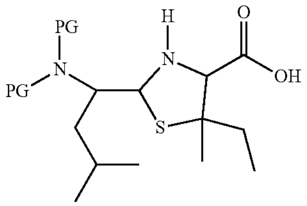
(II.9)
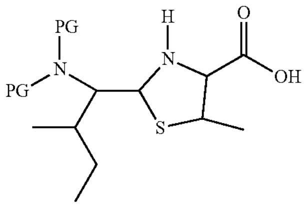
-continued
(II.10)
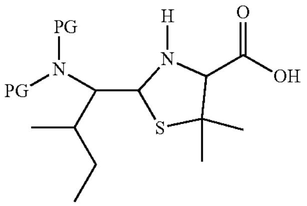
(II.11)
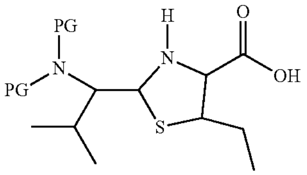
(II.12)
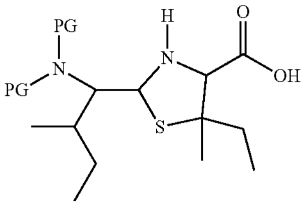
(II.13)
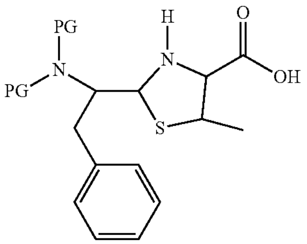
(II.14)
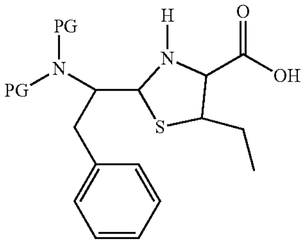
(II.15)
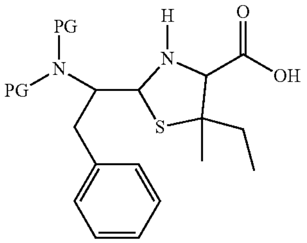
(II.16)
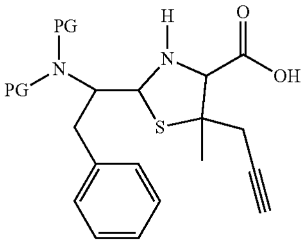

-continued
(II.17)
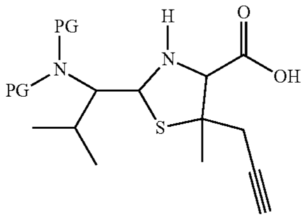
(II.18)
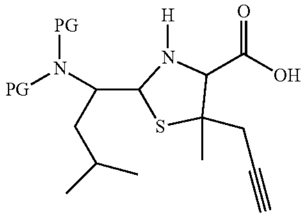
(II.19)
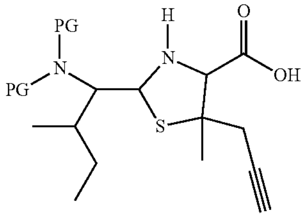
(II.20)
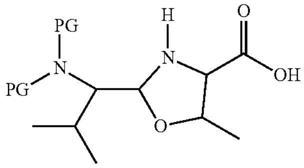
(II.21)
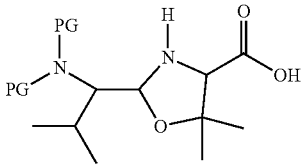
(II.22)
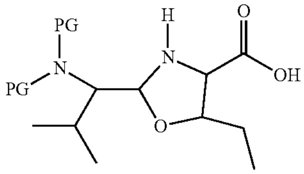
(II.23)
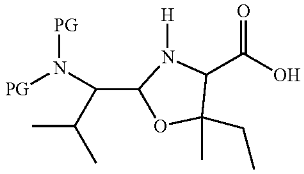
(II.24)
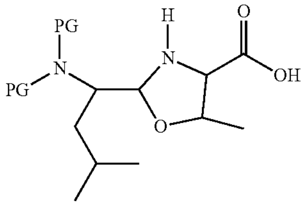
-continued
(II.25)
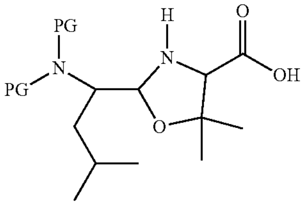
(II.26)
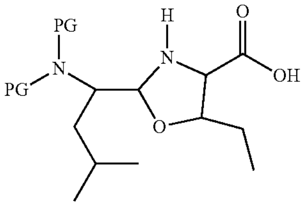
(II.27)
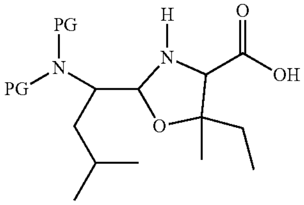
(II.28)
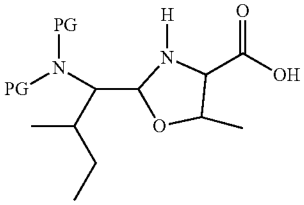
(II.29)
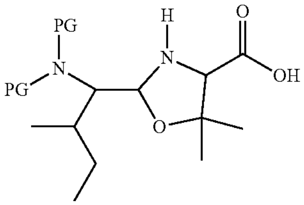
(II.30)
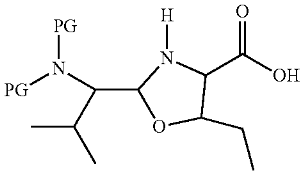
(II.31)
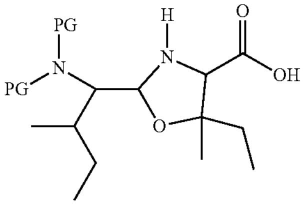

-continued (II.32)

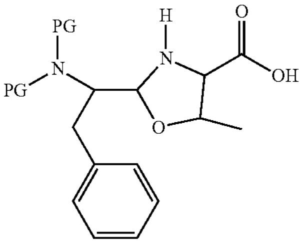

(II.33)

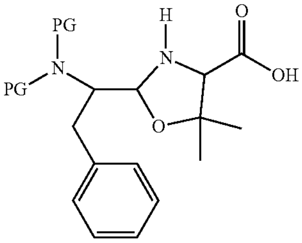

(II.34)

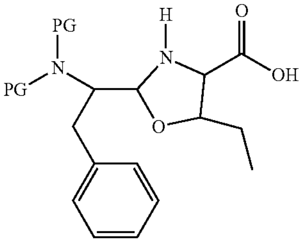

(II.35)

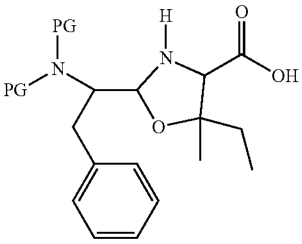

(II.36)

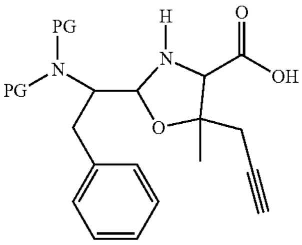

(II.37)

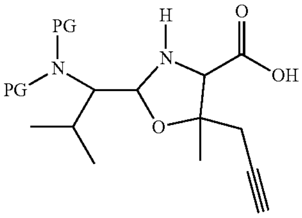

-continued (II.38)

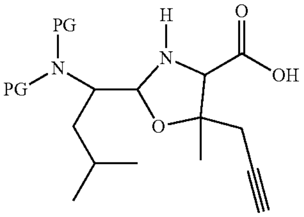

(II.39)

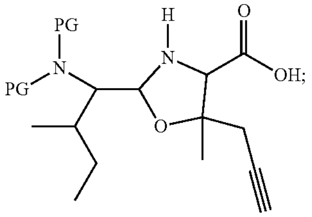

wherein preferably two substituents PG represent an H and one substituent PG (preferably in the terminal amino group) represents a protecting group.

[6]A method for synthesizing a thiazolidine or oxazolidine building block according to [4] or [5], comprising the following steps (a) to (d):

(a) Providing a protected amino acid derivative of formula (III):

(III)

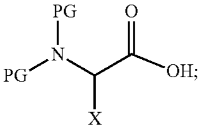

(b) Reducing the amino acid derivative (III) of step (a) to the alcohol of formula (IV) by (b1) in a first activation step, activating the amino acid derivative of formula (III), with an activating reagent, in an inert solvent; and (b2) in a second step, reducing the activation product of step (b1) to a compound of formula (IV):

(IV)

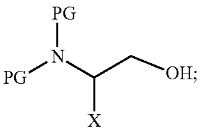

(c) Oxidizing the compound (IV) of step (b), with an oxidizing agent, in an aprotic solvent, and optionally an addition of water, to give the corresponding aldehyde of formula (V):

(V)

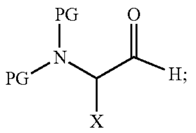

(d) Reacting (condensation) the compound (V) of step (c), preferably in a solvent mixture of water and a polar-protic solvent, in a water:polar-protic solvent ratio of ≤1:1 (v/v) and at a reaction temperature of at least 30° C., with a compound of formula (VI):

(VI)

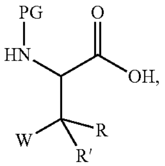

to obtain a thiazolidine or oxazolidine building block according to [4] or [5]; wherein:

W is equal to SH or OH;

R and R' each are selected from the group consisting of H, methyl, ethyl, n-propyl, 1-methylethyl, n-butyl, 2-methylpropyl, 1-methylpropyl, benzyl and propargyl, with the proviso that when R is H, R' is not H;

PG each represents H or a protecting group, wherein individual PG may be the same or different, and wherein the protecting group is preferably selected from the group consisting of 9-fluorenylmethoxycarbonyl (Fmoc), tert-butyloxycarbonyl (Boc), benzyloxycarbonyl (Cbz), benzyl (Bn), trityl (Trt), acetyl (Ac) and tosyl (Ts);

X is selected from the group consisting of: methyl, ethyl, n-propyl, 2-propenyl, 1-methylethyl, n-butyl, 2-methylpropyl, 1-methylpropyl, 1,1-dimethylethyl, n-pentyl, 3-methylbutyl, benzyl, propargyl, 1H-indole-3-ylmethyl, 1N-methyl-1H-indole-3-ylmethyl, 3-benzothienylmethyl, 1-naphthylmethyl, 9-anthracenylmethyl and pyrenylmethyl;

with the proviso that when Z is equal to S and X is equal to methyl, benzyl or 1H-indole-3-ylmethyl, R is not methyl.

[7] Method for the synthesis of a thiazolidine or oxazolidine building block according to [6]

wherein in step (b1) the activating reagent is selected from thionyl chloride, ethylene chloroformate, oxalyl chloride, N,O-dimethylhydroxylamine, or CDI, preferably CDI; an inert cyclic ether solvent such as 1,4-dioxane, cyclopentyl methyl ether, 2-methyltetrahydrofuran (2-Me-THF), tetrahydrofuran (THF), preferably THF, is used; and/or the activation is carried out at 15 to 25° C. for at least 5 min;

wherein in step (b2) the activation product is reduced using $Pd/C/H_2$, Pd/C/triethylsilane, $NiCl_2/NaBH_4$, lithium aluminum hydride ($LiAlH_4$), diisobutyl aluminum hydride (DIBAL-H), sodium cyanoborohydride ($NaBH_3CN$) or sodium borohydride ($NaBH_4$), preferably $NaBH_3CN$ or $NaBH_4$, at 0° C. for at least 15 min;

wherein in step (c) the oxidizing agent is oxalyl chloride/DMSO/$NEt_3$ or DMP, more preferably DMP; the aprotic solvent is ethyl acetate, acetone, toluene, THF, chloroform, or dichloromethane (DCM), preferably toluene, THF, chloroform, or DCM, preferably DCM; the oxidizing agent is between 1.0 to 2.0 equiv.; and/or water, preferably between 1.0 to 1.5 equiv., is added to the reaction; and/or wherein in step (d) the ratio of water to polar-protic solvent is ≤1:1 (v/v); the polar-protic solvent is formic acid, acetic acid, ethanol, isopropanol or methanol, preferably ethanol, isopropanol or methanol, more preferably methanol; and/or the reaction is carried out at at least 50° C., preferably between 55° C. to 75° C.

[8]A method for solid-phase peptide synthesis of a cyclic compound according to any one of [1] to [3], comprising the following steps (i) to (iv):

(i) Providing, bound to a solid phase via its terminal carboxyl group, an amino acid derivative of formula (VII)

(VII)

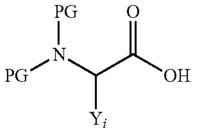

wherein i is 1 to 5;

a linear peptide consisting of two, three, four or five amino acid derivatives of formula (VII); or a Thiazolidine or oxazolidine building block according to [4] or [5];

wherein the terminal amino group is protected by at least one protecting group;

(ii) Carrying out, starting from the amino acid derivative of formula (VII), the peptide, or the thiazolidine or oxazolidine building block of step (i), by carrying out one or more consecutive coupling reactions, adding one or more amino acid derivatives of formula (VII), one or more linear peptides consisting of two to five amino acid derivatives of formula (VII), or of a thiazolidine or oxazolidine building block according to [4] or [5], wherein the terminal amino group is protected by at least one protecting group, a stepwise solid phase synthesis of a linear solid phase-bound compound comprising five amino acid derivatives of formula (VII), wherein i is 1 to 5, and a thiazolidine or oxazolidine building block according to [4] or [5];

(iii) Removing the protecting groups of the linear, solid phase-bound product of step (ii), and cleaving it off from the solid phase to form a linear compound not bound to the solid phase;

(iv) Macrocyclization of the linear compound of step (iii) not bound to the solid phase, preferably by macrolactamization, thereby obtaining the cyclic compound according to any one of [1] to [3];

wherein:

X and $Y_1$ to $Y_5$ are each selected from the group consisting of: methyl, ethyl, n-propyl, 2-propenyl, 1-methylethyl, n-butyl, 2-methylpropyl, 1-methylpropyl, 1,1-dimethylethyl, n-pentyl, 3-methylbutyl, benzyl, propargyl, 1H-indole-3-ylmethyl, 1N-methyl-1H-indole-3-ylmethyl, 3-benzothienylmethyl, 1-naphthylmethyl, 9-anthracenylmethyl and pyrenylmethyl;

Z is equal to O or S;

PG each represents H or a protecting group, wherein individual PG may be the same or different, and wherein the protecting group is preferably selected from the group consisting of 9-fluorenylmethoxycarbonyl (Fmoc), tert-butyloxycarbonyl (Boc), benzyloxycarbonyl (Cbz), benzyl (Bn), trityl (Trt), acetyl (Ac) and tosyl (Ts);

R and R' each are selected from the group consisting of H, methyl, ethyl, n-propyl, 1-methylethyl, n-butyl, 2-methylpropyl, 1-methylpropyl, benzyl and propargyl, with the proviso that when R is H, R' is not H;

with the proviso that when X, $Y_1$, $Y_4$ and $Y_5$ are 1-methylethyl, $Y_2$ is 1H-indole-3-ylmethyl, $Y_3$ is 2-methylpropyl, R is H and R' is methyl, Z is not O.

[9] The method according to [8], wherein the thiazolidine or oxazolidine building block used in step (i) or step (ii) is prepared by the method according to [6] or [7].

[10] Method according to [8] or [9], wherein in step (i) a linear peptide consisting of two to five, preferably five, amino acid derivatives of formula (VII), wherein the terminal amino group is protected by at least one protecting group, is provided;

in step (ii), the amino acid derivatives of formula (VII) or peptides to be added, or the thiazolidine or oxazolidine building block to be added, are not bound to a solid phase; and in each of the one or more coupling reactions, initially the at least one protecting group is removed from the amino acid derivative of formula (VII), the peptide, respectively, the thiazolidine or oxazolidine building block of step (i), and then the coupling with the amino acid derivative of formula (VII), which is not bound to a solid phase, the peptide, or the thiazolidine or oxazolidine building block is carried out;

in step (iii), deprotecting and cleaving off from the solid support is carried out by a first treatment with 0.5-4% (v/v) DBU (1,8-diazabicyclo[5.4.0]undec-7-ene) and 5-15% (v/v) morpholine in DMF and a second treatment with trifluoroacetic acid (TFA), triisopropylsilane (TIPS) and water, preferably in a ratio of 90-92.5:2.5-5:5 (v/v/v); and/or in step (iv), a macrolactamization is carried out, wherein the linear, solid phase-bound compound of step (iii) is cyclized at 15 to 25° C. with HATU, DIPEA and HOAt, using a polar aprotic solvent, preferably DMF.

[11]A cyclic compound according to any one of [1] to [3], thiazolidine or oxazolidine building block according to [4], method according to [6] or [7], and/or method according to any one of [8] to [10], wherein:

X is selected from the group consisting of: 1-methylethyl, 2-methylpropyl, 1-methylpropyl, benzyl, propargyl,

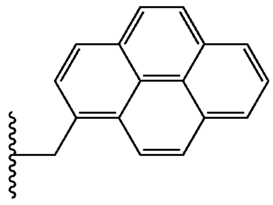 [SMILES: *Cc1ccc2ccc3cccc4ccc1c2c34]

(1-pyrenylmethyl) and

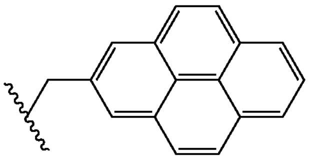 [SMILES: *Cc1cc2ccc3cccc4ccc(c1)c2c34]

(2-pyrenylmethyl);

$Y_1$ to $Y_5$ are each selected from the group consisting of: Methyl, 1-methylethyl, 2-methylpropyl, 1-methylpropyl, benzyl, 1H-indol-3-yl-methyl, propargyl,

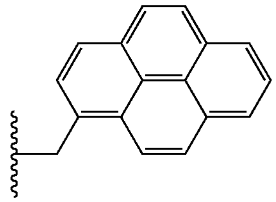 [SMILES: *Cc1ccc2ccc3cccc4ccc1c2c34]

(1-pyrenylmethyl) and

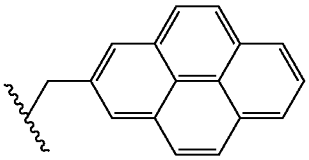

(2-pyrenylmethyl);

W is equal to OH or SH;

Z is equal to O or S; and/or

R and R' are each selected from the group consisting of H, methyl, ethyl, and propargyl.

[12] Cosmetic preparation containing (a) one or more cyclic compounds according to any one of [1] to [3]; and (b) one or more cosmetically acceptable carriers.

[13] Cosmetic preparation according to [12], wherein the cosmetic preparation is in the form of a dermatological preparation for topical application; and/or wherein the one or more cyclic compounds have an antimicrobial, preferably antiviral, antibacterial and/or antifungal, in particular antiviral and/or non-selective antibacterial (preferably against Gram-positive bacteria, but preferably not or only minimally against Gram-negative bacteria), activity and/or have a supportive effect on the innate immune response, in particular of the skin.

[14] Cosmetic preparation according to [12] or [13], containing:

(a) a cyclic compound characterized by the following formula:

I.3

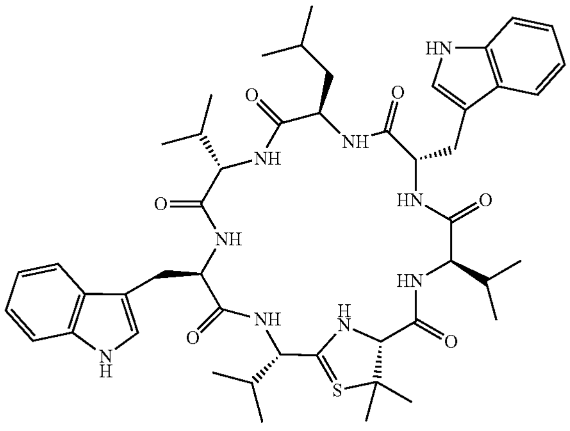

(b) one or more cosmetically acceptable carriers.

BRIEF DESCRIPTION OF THE DRAWINGS

FIG. 2: (A) Bioassay with *Staphylococcus aureus* USA300 LAC (37° C., 160 rpm, 22 h) using the four cyclic compounds I.1, I.2, I.3 and I.4: Table with $OD_{600}$ values in the body of the table, after growth in different concentrations of the cyclic compounds; DMSO as negative control; color coding: minimal inhibitory concentration (MIC); red (or gray, respectively): Growth; white: no growth. (B) Bioassay with *Staphylococcus aureus* USA300 LAC (37° C., 160 rpm, 22 h) using cyclic compounds I.19, I.20, I.21, I.22, I.23 and I.24: table with $OD_{600}$ values in the body of the table, after growth in different concentrations of the cyclic compounds; DMSO as negative control; color coding: minimal inhibitory concentration (MIC); red (or gray, respectively): Growth; white: no growth.

DETAILED DESCRIPTION OF THE INVENTION

Cyclic Compound of Formula (I)

Figure 1C:
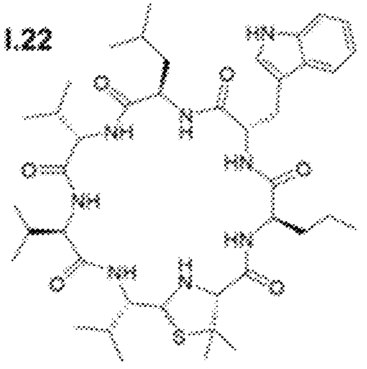
FIG. 1: (A) Structural formulae of the cyclic compounds used in the examples, I.1 (ISW 1-0), I.2 (ISW 1-1), I.3 (ISW 1-2) I.4 (ISW 1-4), including molecular weight. (B) Structural formulae of the cyclic compounds I.19, I.20, and I.21 used in the examples, including molecular mass. (C) Structural formulae of cyclic compounds I.22, I.23 and I.24 used in the examples, including molecular mass.
Figure 1C:
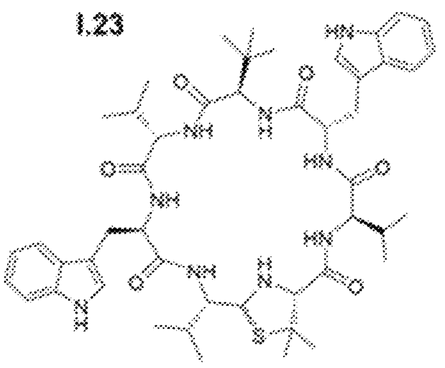
Figure 1C:
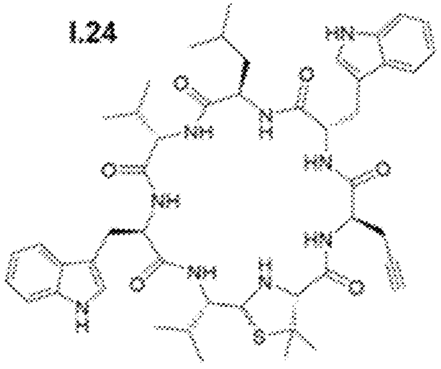
Figure 1C:
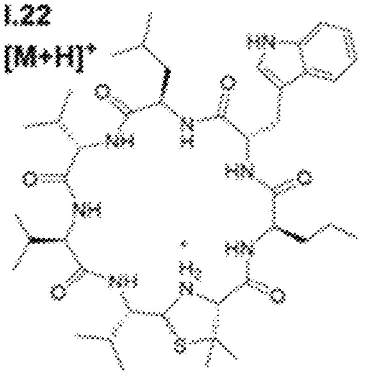
Figure 1C:
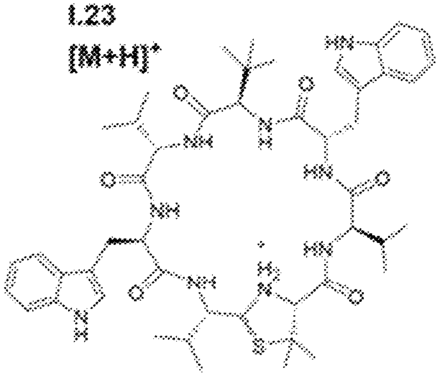
Figure 1C:
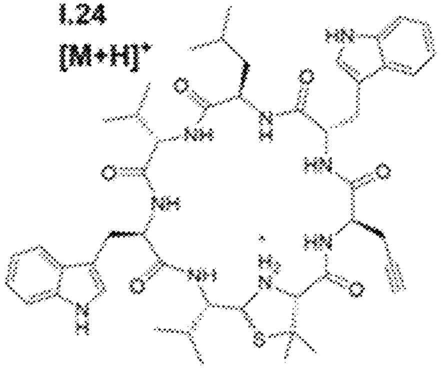

In a first aspect, the present invention is directed to a novel cyclic compound of formula (I):

(I)

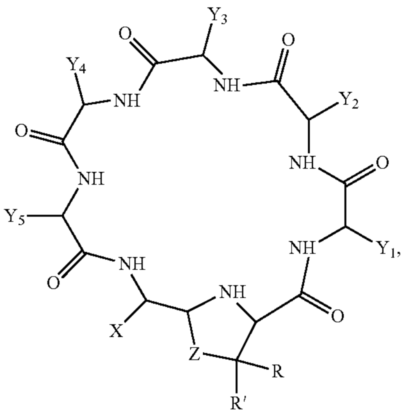

wherein:

- X and $Y_1$ to $Y_5$ are each selected from the group consisting of: methyl, ethyl, n-propyl (having the formula $CH_3—CH_2—CH_2—$), 2-propenyl (having the formula $H_2C═CH—CH_2—$), 1-methylethyl (or isopropyl, having the formula $(CH_3)_2CH—$), n-butyl (having the formula $CH_3—CH_2—CH_2—CH_2—$), 2-methylpropyl (or isobutyl, having the formula $(CH_3)_2CH—CH_2—$), 1-methylpropyl (or butane-2-yl, or, respectively sec-butyl, having the formula $CH_3—CH_2—CH(CH_3)—$), 1,1-dimethylethyl (or tert-butyl having the formula $(CH_3)CH—$), n-pentyl (having the formula $CH_3—CH_2—CH_2—CH_2—CH_2—$), 3-methylbutyl (or isopentyl, having the formula $(CH_3)_2CH—CH_2—CH_2—$), benzyl (or Bn having the formula phenyl-$CH_2—$), propargyl (or ethinylmethyl, having the formula $HC≡C—CH_2—$), 1H-indole-3-ylmethyl (having the formula

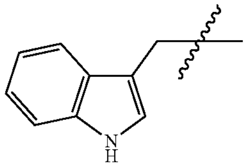

), 1N-methyl-1H-indole-3-ylmethyl (having the formula

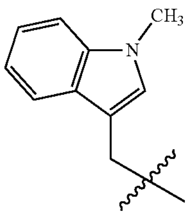

), 3-benzothienylmethyl (having the formula

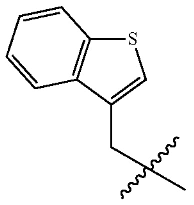

), 1-naphthylmethyl (having the formula

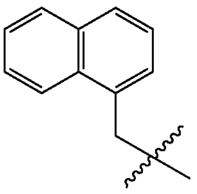

), 9-anthracenylmethyl (having the formula

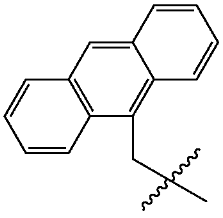

)

and pyrenylmethyl (i.e. 1-pyrenylmethyl having the formula

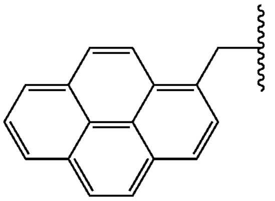

, 2-pyrenylmethyl having the formula

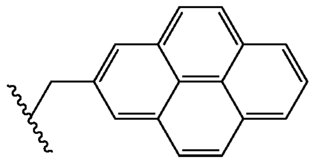 [SMILES: *Cc1cc2ccc3cccc4ccc(c1)c2c34]

, etc.);

Z is equal to O or S;

R and R' each are selected from the group consisting of H, methyl, ethyl, n-propyl, 1-methylethyl, n-butyl, 2-methylpropyl (isobutyl), 1-methylpropyl (butane-2-yl or sec-butyl), benzyl and propargyl, with the proviso that when R is H, R' is not H;

the C atoms, which are directly linked to the substituents $Y_1$, $Y_2$, $Y_3$, $Y_4$, $Y_5$ and X, in this order, each have an alternating absolute stereochemical configuration; and the C atom, which is bound to substituent X, and the C atom in position 4 of the thiazolidine or oxazolidine ring have the same absolute stereochemical configuration when Z is O and an opposite absolute stereochemical configuration when Z is S;

with the proviso that when X, $Y_1$, $Y_4$ and $Y_5$ are 1-methylethyl, $Y_2$ is 1H-indole-3-ylmethyl, $Y_3$ is 2-methylpropyl, R is H and R' is methyl, Z is not O;

and the salts thereof, the solvates thereof, and the solvates of the salts thereof.

The following explanations regarding the various substituents and parameters apply equally to all aspects and embodiments of the present invention.

The term "each selected" with respect to the parameters X and $Y_1$ to $Y_5$, as well as R and R' generally means, apart from certain exceptions, that these substituents may each stand for identical residues from the corresponding lists above or for different residues from these lists. In the cyclic compound of formula (I) according to the invention, Z is not O if, in sum, X, $Y_1$, $Y_4$ and $Y_5$ are 1-methylethyl, $Y_2$ is 1H-indole-3-ylmethyl, $Y_3$ is 2-methylpropyl, R is H and R' is methyl. Furthermore, for substituents R and R' applies, in view of the present invention, that when R is H, R' is not H.

The cyclic compound of formula (I) according to the invention combines a number of advantageous properties, particularly for cosmetic use.

The cyclic compound of formula (I) according to the invention exhibits excellent solubility and stability in common solvents and carriers, especially cosmetically acceptable solvents and cosmetically acceptable carriers, which favors its use in cosmetic preparations. Furthermore, it was surprisingly found that the cyclic compound of formula (I) according to the invention is not or not readily degraded by conventional proteases. This leads to advantageous stability, for example, when used on skin, e.g. against bacterial and mycotic proteases of skin-resident microorganisms and skin's own proteases.

As a cosmetic active ingredient for use in non-therapeutic treatment, the novel cyclic compound of formula (I) is highly potent and thus already applicable in small amounts or low concentrations for cosmetic use. When the compound of formula (I) according to the invention is used as a cosmetic active ingredient for the non-therapeutic treatment and/or prevention of a cosmetic or dermatological phenomenon associated with the (in particular cutaneous) occurrence of viruses, bacteria, mycota, parasites and protozoa, the body's own mechanisms, in particular the skin's own mechanisms, can be advantageously exploited or supported.

The residues listed with respect to substituents X, $Y_1$ to $Y_5$, R and R', in terms of the present invention, are also known to the skilled person as follows (where "-" at the end of the respective simplified structural formulae, or "~" at the respective structural formulae, respectively, indicates in each case where the residue is linked to the compound in question).

In terms of the present invention, the methyl residue has the formula $CH_3$— and is also abbreviated as "Me". The residue ethyl, having the formula $CH_3$—$CH_2$—, is also abbreviated as "Et" herein. The residue n-propyl has the formula $CH_3$—$CH_2$—$CH_2$—. The 2-propenyl residue has the formula $H_2C$═CH—$CH_2$—. The residue 1-methylethyl in terms of the present invention is also known to the skilled person as isopropyl and has the formula $(CH_3)_2CH$—. The residue n-butyl has the formula $CH_3$—$CH_2$—$CH_2$—$CH_2$—. The residue 2-methylpropyl in terms of the present invention is also known to the skilled person as isobutyl and has the formula $(CH_3)_2CH$—$CH_2$—. The residue 1-methylpropyl is also known to the skilled person as butane-2-yl or sec-butyl and has the formula $CH_3$—$CH_2$—$CH(CH_3)$—. The residue 1,1-dimethylethyl in terms of the present invention is also known to the skilled person as tert-butyl and has the formula $(CH_3)_3CH$—. The residue n-pentyl has the formula $CH_3$—$CH_2$—$CH_2$—$CH_2$—$CH_2$—. The residue 3-methylbutyl is also known to the person skilled in the art as isopentyl and has the formula $(CH_3)_2CH$—$CH_2$—$CH_2$—.

The residue benzyl (or (1-phenyl)methyl, respectively) in terms of the present invention is also abbreviated to "Bn" and has the formula phenyl-$CH_2$—. The residue propargyl is also known to the skilled person as ethynylmethyl or 2-propynyl and has the formula HC≡C—$CH_2$—. The residue 1H-indole-3-ylmethyl in terms of the present invention, in terms of the present invention, also known as indole-3-ylmethyl, has the formula

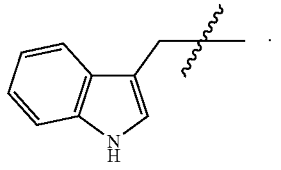 [SMILES: *Cc1c[nH]c2ccccc12]

The residue 1N-methyl-1H-indole-3-ylmethyl, in terms of the present invention, has the formula

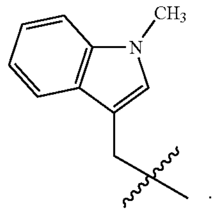 [SMILES: *Cc1cn(C)c2ccccc12]

The residue 3-benzothienylmethyl, in terms of the present invention, has the formula

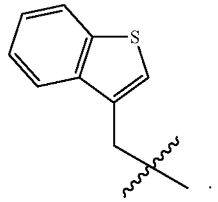 [SMILES: *Cc1csc2ccccc12]

The residue 1-naphthylmethyl, in terms of the present invention, has the formula

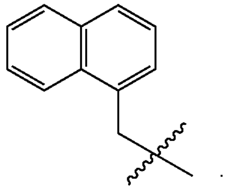 [SMILES: *Cc1cccc2ccccc12]

The residue 9-anthracenylmethyl has the formula

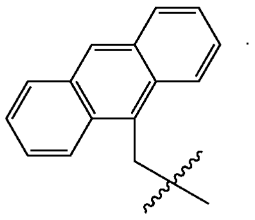 [SMILES: *Cc1c2ccccc2cc2ccccc12]

The residue pyrenylmethyl (or pyren-ylmethyl), as used herein, stands for a pyrene ring which is linked via one of its peripheral ring carbon atoms C1 to C10 to a methyl residue which in turn serves as a connecting point for the pyrenylmethyl overall residue, i.e. 1-pyrenylmethyl, 2-pyrenylmethyl, 3-pyrenylmethyl, 4-pyrenylmethyl, 5-pyrenylmethyl, etc. (or 1-pyren-ylmethyl, 2-pyren-ylmethyl, 3-pyren-ylmethyl, 4-pyren-ylmethyl, 5-pyren-ylmethyl, etc.). For example, the residue 1-pyrenylmethyl (or (1-pyrenyl) methyl, pyren-1-ylmethyl, or (pyren-1-yl)methyl) has the formula

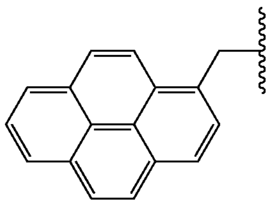
.

The residue 2-pyrenylmethyl (or (2-pyrenyl)methyl, pyren-2-ylmethyl, or (pyren-2-yl)methyl), for example, has the formula

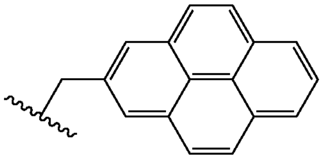
, etc.

The cyclic compounds of the present invention falling within the scope of formula (I) are composed of five amino acid derivatives and one thiazolidine or oxazolidine building block. An "amino acid derivative" in terms of the present invention is generally understood to mean the classical 20 natural L- and D-α-amino acids and their diastereomers but also modified derivatives thereof with deviating residues (R). The cyclic compound of formula (I) according to the invention comprises only amino acid derivatives with residues (R) which correspond to the residues defined for the substituents $Y_1$ to $Y_5$.

A thiazolidine or oxazolidine building block in terms of the present invention comprises a 1,3-thiazolidine ring or a 1,3-oxazolidine ring, which is linked in position 2 to a carbon atom (C atom), which in turn is linked to substituent X (and also to an amino group). The positions in the thiazolidine or oxazolidine ring result from the standard nomenclature as known to the person skilled in the art, i.e:

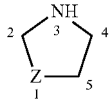

wherein Z is equal to S or O and the numbers 1-5 define the positions in the ring.

The 1,3-thiazolidine ring or 1,3-oxazolidine ring of the thiazolidine or oxazolidine building block is linked to a carboxyl group in position 4, in the free state (i.e., in the state not integrated into a peptide derivative), and, in the linear peptide derivative (i.e. in the linear precursor prior to cyclization to the cyclic compound according to the invention) or in the cyclic peptide derivative (i.e. in the cyclic compound according to the invention), is linked to the peptide derivative backbone via an amide group (i.e. in the C-terminus of the thiazolidine or oxazolidine building block); in the linear peptide derivative, of course, only if the thiazolidine or oxazolidine building block is not C-terminal. The 1,3 thiazolidine ring or 1,3-oxazolidine ring is attached to residues R and R' at position 5.

In the cyclic compound of formula (I) according to the invention, the C atoms directly linked to the substituents $Y_1$, $Y_2$, $Y_3$, $Y_4$, $Y_5$ and X have, in this order, a respective alternating absolute, and also relative, stereochemical configuration. That is, for example, in the cyclic compound of formula (I) according to the invention, directly successive amino acid derivatives, each have an alternating absolute, and also relative, stereochemical configuration of the α-carbon (Ca).

The terms "(alternating) absolute stereochemical configuration" and "(alternating) relative stereochemical configuration" are well known to the skilled person. The term "absolute stereochemical configuration" as used in the context of the present invention refers to the R-/S nomenclature (but not to the relative D-/L nomenclature). Thus, an "alternating absolute stereochemical configuration" in terms of the present invention means that when the absolute stereochemical configuration of a carbon atom (C atom) directly linked to a substituent $Y_1$ to $Y_5$ or X is an R configuration, the closest C atoms along the chain backbone of the cyclic compound of formula (I) on either side, which are also directly linked to a substituent $Y_1$ to $Y_5$ or X, have an S configuration. For example, in the cyclic compound of formula (I), if the $C_{Y3}$ (that is, the C atom directly linked to substituent $Y_3$) has an R configuration, $C_{Y4}$ (and also $C_{Y2}$) has an S configuration, $C_{Y5}$ has an R configuration, $C_X$ has an S configuration, etc. In contrast, if $C_{Y3}$ has an S-configuration, $C_{Y4}$ (and also $C_{Y2}$) has an R-configuration, $C_{Y5}$ has an S-configuration, $C_X$ has an R-configuration, etc.

Also the term "alternating relative stereochemical configuration" as used in the context of the present invention is to be understood in this sense. The term "relative stereochemical configuration" as used in the context of the present invention refers to the D,L nomenclature for amino acids and their derivatives. Thus, an "alternating stereochemical relative configuration" in terms of the present invention means that when the relative stereochemical configuration of a C atom directly linked to a substituent $Y_1$ to $Y_5$ or X is an L configuration, the C atoms closest along the chain backbone of the cyclic compound (I) on either side, which are also directly linked to a substituent $Y_1$ to $Y_5$ or X, have a D configuration. For example, if in the cyclic compound of formula (I), the $C_{Y4}$ (that is, the C atom directly linked to substituent $Y_4$) has an L configuration, $C_{Y5}$ (and also $C_{Y3}$) has a D configuration, $C_X$ has an L configuration, $C_{Y1}$ has a D configuration, etc. In contrast, if $C_{Y4}$ has a D configuration, $C_{Y5}$ (and also $C_{Y3}$) has an L configuration, $C_X$ has a D configuration, $C_{Y1}$ has an L configuration, etc.

Similarly, the terms "opposite absolute stereochemical configuration" and "same absolute stereochemical configuration" and "opposite relative stereochemical configuration" or "same relative stereochemical configuration", respectively, are to be understood in this sense. That is, an "opposite absolute stereochemical configuration", in terms of the present invention, means that if the one absolute stereochemical configuration is an R configuration, the opposite absolute stereochemical configuration is an S configuration. And a "same absolute stereochemical configuration" in terms of the present invention means that if the one absolute configuration is an R configuration, the same absolute configuration is also an R configuration. This applies analogously to the relative stereochemical configuration, so that an "opposite relative stereochemical configuration" in terms of the present invention means that if the one relative stereochemical configuration is a D configuration, the opposite relative stereochemical configuration is an L configuration, etc.

In this context, only the alternating stereochemical configuration is given for the cyclic compound of formula (I)

according to the invention (as well as the corresponding opposite or same absolute stereochemical configuration for the thiazolidine or oxazolidine building block, respectively, as described in the following); in contrast, a concrete assignment of the absolute or relative stereochemical configuration of individual C atoms in the cyclic compound of formula (I) according to the invention is not given.

In particular, the cyclic compound of formula (I) according to the invention can thus, for example, depending on its specific structure, exist in stereoisomeric forms (enantiomers, diastereomers). The invention therefore encompasses also the enantiomers or diastereomers and corresponding mixtures thereof. The stereoisomeric unitary constituents may be isolated from such mixtures of enantiomers and/or diastereomers in a known manner. If the compound according to the invention may occur in tautomeric forms, the present invention encompasses all tautomeric forms.

In the thiazolidine or oxazolidine building block of the cyclic compound of formula (I) according to the invention, the C atom directly linked to substituent X is also linked via a direct bond to a thiazolidine or oxazolidine ring in position 2.

In the cyclic compound of formula (I) according to the invention, the C atom directly linked to substituent X and the C atom in position 4 of the thiazolidine or oxazolidine ring have the same absolute stereochemical configuration when Z is equal to O (i.e. if it is an oxazolidine ring) and an opposite absolute stereochemical configuration when Z is equal to S (i.e. if it is a thiazolidine ring). In this context, the terms “opposite absolute stereochemical configuration” and “same absolute stereochemical configuration” are to be understood as defined above. This means, for example, that if a cyclic compound (I) according to the invention has an oxazolidine ring and this has an R-configuration in position 4, also the C-atom which is directly linked to the substituent X has an R-configuration, or, respectively, if a cyclic compound (I) according to the invention has a thiazolidine ring and this has an R-configuration in position 4, the C-atom which is directly linked to the substituent X has an S-configuration.

Salts preferred for the purposes of the present invention are physiologically (in particular cosmetically) compatible salts of the compound of formula (I) according to the invention. However, also included are salts which are not themselves suitable for cosmetic applications, but which can be used, for example, for isolating or purifying the compound of formula (I) according to the invention.

Examples of cosmetically acceptable salts of the cyclic compound of formula (I) include salts of inorganic bases such as ammonium salts, alkali metal salts, in particular sodium or potassium salts, alkaline earth metal salts, in particular magnesium or calcium salts; salts of organic bases, in particular salts derived from cyclohexylamine, benzylamine, octylamine, ethanolamine, diethanolamine, diethylamine, triethylamine, ethylenediamine, procaine, morpholine, pyrroline, piperidine, N-ethylpiperidine, N-methylmorpholine, piperazine as organic base; or salts with basic amino acids, in particular lysine, arginine, ornithine and histidine.

Examples of cosmetically acceptable salts of the compound of formula (I) also include salts of inorganic acids such as hydrochlorides, hydrobromides, sulfates, phosphates or phosphonates; Salts of organic acids, in particular acetates, formates, propionates, lactates, citrates, fumarates, maleates, benzoates, tartrates, malates, methanesulfonates, ethanesulfonates, toluenesulfonates or benzenesulfonates; or salts with acidic amino acids, in particular aspartate or glutamate.

Solvates in the sense according to the invention refer to those forms of the compound of formula (I) according to the invention which form a complex in the solid or liquid state by coordination with solvent molecules. Hydrates are a special form of solvates in which coordination occurs with water. The compound of formula (I) according to the invention may also be complexed, for example with iron, calcium, etc., in which case the compound of formula (I) may act as a ligand, so that corresponding complexes are also the subject of the present invention.

In a preferred embodiment of the cyclic compound of formula (I) according to the invention, the substituent X is selected from the group consisting of ethyl, n-propyl, 2-propenyl, 1-methylethyl, n-butyl, 2-methylpropyl, 1-methylpropyl, 1,1-dimethylethyl, n-pentyl, 3-methylbutyl, benzyl, propargyl, 1N-methyl-1H-indole-3-ylmethyl, 3-benzothienylmethyl, 1-naphthylmethyl, 9-anthracenylmethyl, and pyrenylmethyl (the pyrenylmethyl preferably selected being 1-pyrenylmethyl or 2-pyrenylmethyl, more preferably 1-pyrenylmethyl). In another preferred embodiment, X is selected from the group consisting of n-propyl, 1-methylethyl, n-butyl, 2-methylpropyl, 1-methylpropyl, 1,1-dimethylethyl, benzyl, propargyl, and pyrenylmethyl (preferably 1-pyrenylmethyl or 2-pyrenylmethyl, more preferably 1-pyrenylmethyl). In still another preferred embodiment, X is selected from the group consisting of 1-methylethyl, 2-methylpropyl, 1-methylpropyl, 1,1-dimethylethyl, benzyl, propargyl, and pyrenylmethyl (preferably 1-pyrenylmethyl or 2-pyrenylmethyl, more preferably 1-pyrenylmethyl). In an alternatively preferred embodiment, X is selected from the group consisting of n-propyl, 1-methylethyl, n-butyl, 2-methylpropyl, 1-methylpropyl, 1,1-dimethylethyl, n-pentyl, and 3-methylbutyl.

In a preferred embodiment of the present invention, substituents $Y_1$ to $Y_5$ are each selected from the group consisting of methyl, ethyl, n-propyl, 2-propenyl, 1-methylethyl, n-butyl, 2-methylpropyl, 1-methylpropyl, 1,1-dimethylethyl, benzyl, propargyl, 1H-indole-3-ylmethyl, 1N-methyl-1H-indole-3-ylmethyl, 3-benzothienylmethyl, 1-naphthylmethyl, 9-anthracenylmethyl, and pyrenylmethyl (preferably 1-pyrenylmethyl or 2-pyrenylmethyl, more preferably 1-pyrenylmethyl). In another preferred embodiment of the present invention, $Y_1$ to $Y_5$ are each selected from the group consisting of methyl, 1-methylethyl, 2-methylpropyl, 1-methylpropyl, benzyl, 1H-indol-3-yl-methyl, propargyl, and pyrenylmethyl (preferably 1-pyrenylmethyl or 2-pyrenylmethyl, more preferably 1-pyrenylmethyl).

For example, for $Y_2$ preferred residues are 1H-indole-3-ylmethyl, 1N-methyl-1H-indole-3-ylmethyl, 3-benzothienylmethyl, 1-naphthylmethyl, 9-anthracenylmethyl, and pyrenylmethyl (preferably 1-pyrenylmethyl or 2-pyrenylmethyl, more preferably 1-pyrenylmethyl), more preferably 1H-indole-3-ylmethyl or pyrenylmethyl (preferably 1-pyrenylmethyl or 2-pyrenylmethyl, more preferably 1-pyrenylmethyl), in which case $Y_5$ is then preferably not an aromatic residue (in particular is not 1H-indole-3-ylmethyl or pyrenylmethyl). For $Y_3$, for example, preferred residues are n-propyl, 1-methylethyl, n-butyl, 2-methylpropyl, 1-methylpropyl and 1,1-dimethylethyl, and 2-methylpropyl is particularly preferred. For $Y_4$, for example, preferred residues are methyl, ethyl, n-propyl, 1-methylethyl, n-butyl, 2-methylpropyl, 1-methylpropyl, 1,1-dimethylethyl, in particular preferred is 1-methylethyl. For example, for $Y_5$ preferred residues are 1H-indole-3-ylmethyl, 1N-methyl-1H-indole-3-ylmethyl, 3-benzothienylmethyl, 1-naphthylmethyl, 9-anthracenylmethyl, and pyrenylmethyl (preferably 1-pyrenylmethyl or 2-pyrenylmethyl, more preferably 1-pyrenylmethyl), more preferably 1H-indole-3-ylmethyl or pyrenylmethyl (preferably 1-pyrenylmethyl or 2-pyrenylmethyl, more preferably 1-pyrenylmethyl), e.g. more preferably 1H-indole-3-ylmethyl, in which case $Y_2$ is then preferably not an aromatic radical (in particular is not 1H-indole-3-ylmethyl or pyrenylmethyl).

In another preferred embodiment of the present invention, $Y_2$ is equal to 1H-indole-3-ylmethyl or pyrenylmethyl (preferably 1-pyrenylmethyl or 2-pyrenylmethyl, more preferably 1-pyrenylmethyl), if $Y_5$ is 1-methylethyl, or $Y_2$ is 1-methylethyl, if $Y_5$ is 1H-indole-3-ylmethyl or pyrenylmethyl (preferably 1-pyrenylmethyl or 2-pyrenylmethyl, more preferably 1-pyrenylmethyl). In still another preferred embodiment of the present invention, $Y_2$ is equal to 1H-indole-3-ylmethyl or pyrenylmethyl (preferably 1-pyrenylmethyl or 2-pyrenylmethyl, more preferably 1-pyrenylmethyl), and $Y_5$ is equal to 1-methylethyl, or $Y_2$ is equal to 1-methylethyl, and $Y_5$ is equal to 1H-indole-3-ylmethyl or pyrenylmethyl (preferably 1-pyrenylmethyl or 2-pyrenylmethyl, more preferably 1-pyrenylmethyl).

In a particularly preferred embodiment of the cyclic compound of formula (I) according to the invention, Z is equal to S. In an alternative preferred embodiment of the cyclic compound of formula (I) according to the invention, Z is equal to O.

In a preferred embodiment of the cyclic compound of formula (I) according to the invention, R and R' are each selected from the group consisting of H, methyl, ethyl, n-propyl, 1-methylethyl, benzyl, and propargyl. In another preferred embodiment of the cyclic compound of formula (I) according to the invention, R and R' are each selected from the group consisting of H, methyl, ethyl, and propargyl. In another preferred embodiment of the cyclic compound of formula (I), R and R' are both methyl. In another preferred embodiment of the cyclic compound of formula (I), R is H; and R' is methyl, ethyl, n-propyl, 1-methylethyl, benzyl, or propargyl.

In a specific preferred embodiment of the cyclic compound of formula (I) according to the invention, X is selected from the group consisting of 1-methylethyl, 2-methylpropyl, 1-methylpropyl, benzyl, propargyl, pyrenylmethyl (preferably 1-pyrenylmethyl or 2-pyrenylmethyl, more preferably 1-pyrenylmethyl); $Y_1$ to $Y_5$ are each selected from the group consisting of methyl, ethyl, n-propyl, 1-methylethyl, 2-methylpropyl, 1-methylpropyl, benzyl, 1H-indole-3-ylmethyl, propargyl, pyrenylmethyl (preferably 1-pyrenylmethyl or 2-pyrenylmethyl, more preferably 1-pyrenylmethyl); Z is equal to O or S; and/or R and R' are each selected from the group consisting of H, methyl, ethyl, and propargyl, with the proviso that when R is H, R' is not H.

Surprisingly, it was found that the cyclic compound of formula (I), wherein either the substituent $Y_2$ or the substituent $Y_5$, but preferably not in positions $Y_2$ and $Y_5$ simultaneously, is a pyrenylmethyl, exhbits a high non-selective antimicrobial, in particular non-selective antibacterial, activity compared to a cyclic compound of formula (I) wherein the substituent $Y_2$ or the substituent $Y_5$ is a 1H-indole-3-ylmethyl. In a preferred embodiment of the cyclic compound of formula (I), the substituent $Y_2$ or substituent $Y_5$ is a pyrenylmethyl (preferably 1-pyrenylmethyl or 2-pyrenylmethyl, more preferably 1-pyrenylmethyl). In another preferred embodiment of the cyclic compound of formula (I), either the substituent $Y_2$ or the substituent $Y_5$ is pyrenylmethyl (preferably 1-pyrenylmethyl or 2-pyrenylmethyl, more preferably 1-pyrenylmethyl), and preferably no other substituent X and $Y_1$ to $Y_5$, is pyrenylmethyl.

In another preferred embodiment of the cyclic compound of formula (I), R and R' both are methyl; $Y_2$ is equal to 1H-indole-3-ylmethyl or pyrenylmethyl if $Y_5$ is equal to 1-methylethyl, or $Y_2$ is equal to 1-methylethyl if $Y_5$ is equal to 1H-indole-3-ylmethyl or pyrenylmethyl; and X is equal to 1-methylethyl. In another preferred embodiment of the cyclic compound of formula (I), R and R' both are methyl; $Y_2$ is equal to 1H-indole-3-ylmethyl or pyrenylmethyl, and $Y_5$ is equal to 1-methylethyl, or $Y_2$ is equal to 1-methylethyl, and $Y_5$ is equal to 1H-indole-3-ylmethyl or pyrenylmethyl; X is equal to 1-methylethyl; and Z is preferably S. In this context, the pyrenylmethyl is preferably 1-pyrenylmethyl or 2-pyrenylmethyl, more preferably 1-pyrenylmethyl.

In another preferred embodiment of the cyclic compound of formula (I), R is equal to H; R' is equal to methyl, ethyl, n-propyl, 1-methylethyl, benzyl or propargyl; $Y_2$ is equal to 1H-indole-3-ylmethyl or pyrenylmethyl if $Y_5$ is equal to 1-methylethyl, or $Y_2$ is equal to 1-methylethyl if $Y_5$ is equal to 1H-indole-3-ylmethyl or pyrenylmethyl; X is equal to 1-methylethyl; and Z is preferably S. In still another preferred embodiment of the cyclic compound of formula (I), R is equal to H; R' is methyl, ethyl, n-propyl, 1-methylethyl, benzyl or propargyl; $Y_2$ is equal to 1H-indole-3-ylmethyl or pyrenylmethyl, and $Y_5$ is equal to 1-methylethyl, or $Y_2$ is equal to 1-methylethyl, and $Y_5$ is equal to 1H-indole-3-ylmethyl or pyrenylmethyl; X is 1 equal to methylethyl; and Z is preferably S. In this context, the pyrenylmethyl is preferably 1-pyrenylmethyl or 2-pyrenylmethyl, in particular 1-pyrenylmethyl.

In still another preferred embodiment of the cyclic compound of formula (I), R is equal to H; R' is equal to methyl, n-propyl, 1-methylethyl, benzyl or propargyl; $Y_2$ is equal to 1H-indole-3-ylmethyl or pyrenylmethyl if $Y_5$ is equal to 1-methylethyl, or $Y_2$ is 1-methylethyl if $Y_5$ is equal to 1H-indole-3-ylmethyl or pyrenylmethyl; X is equal to 1-methylethyl or 2-methylpropyl. In still another preferred embodiment of the cyclic compound of formula (I), R is equal to H; R' is equal to methyl, n-propyl, 1-methylethyl, benzyl or propargyl; $Y_2$ is equal to 1H-indole-3-ylmethyl or pyrenylmethyl, and $Y_5$ is equal to 1-methylethyl, or $Y_2$ is equal to 1-methylethyl, and $Y_5$ is equal to 1H-indole-3-ylmethyl or pyrenylmethyl; X is equal to 1-methylethyl or 2-methylpropyl. In this context, the pyrenylmethyl is preferably 1-pyrenylmethyl or 2-pyrenylmethyl, more preferably 1-pyrenylmethyl.

In still another preferred embodiment of the cyclic compound of formula (I), R and R' are both 1-methylethyl; and $Y_2$ is equal to 1H-indole-3-ylmethyl. In still another preferred embodiment of the cyclic compound of formula (I), R and R' each are H or methyl; $Y_2$ is 1H-indol-3-yl; and X is equal to 1-methylethyl.

In an alternative preferred embodiment, in the cyclic compound (I) according to the invention, the C atom which is directly linked to the substituent $Y_5$ is present in an (absolute) S configuration (i.e. L configuration) if $Y_5$ is equal to pyrenylmethyl.

In specific preferred embodiments, the cyclic compound of formula (I) is characterized by any one of the following formulae I.1a to I.24a:

-continued
I.1a
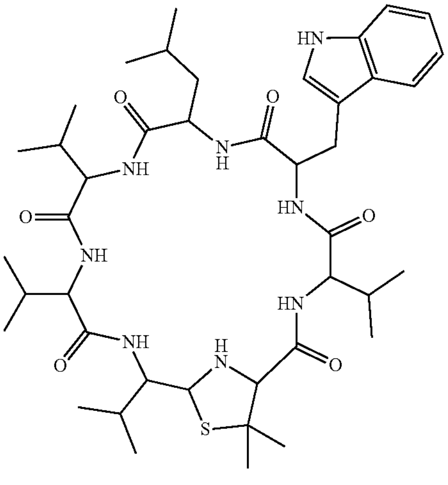
I.2a
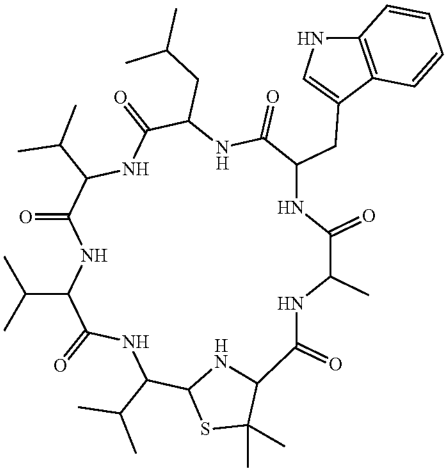
I.3a
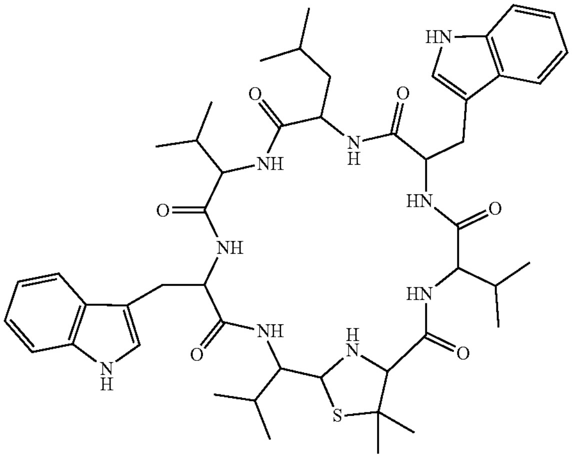
I.4a
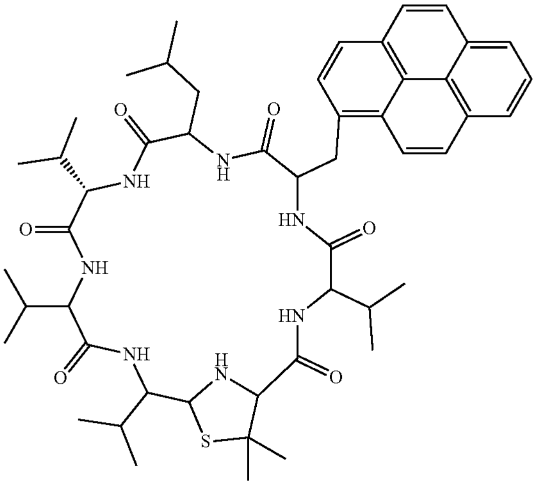
I.5a
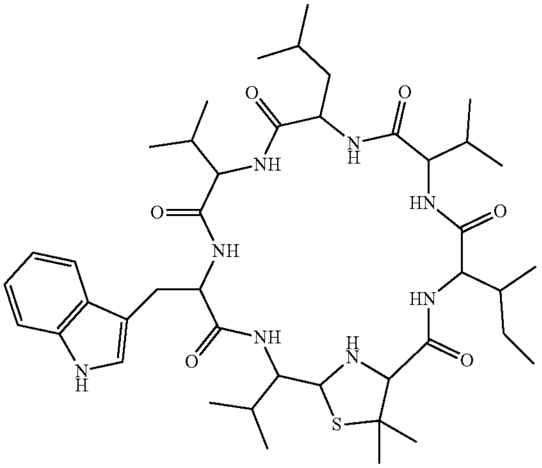
I.6a
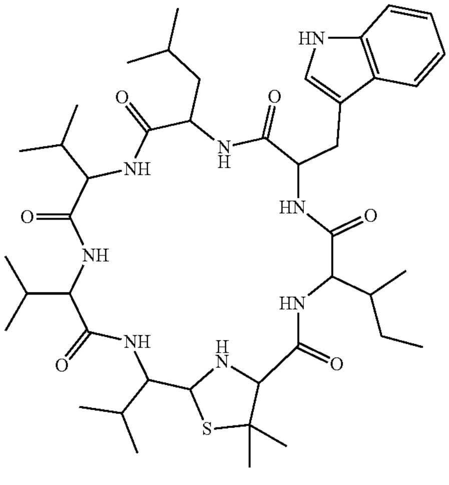

-continued
I.7a
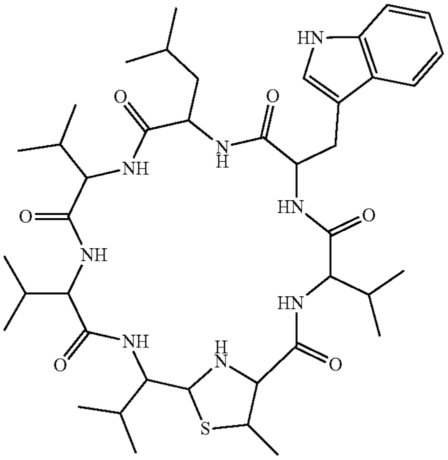
I.8a
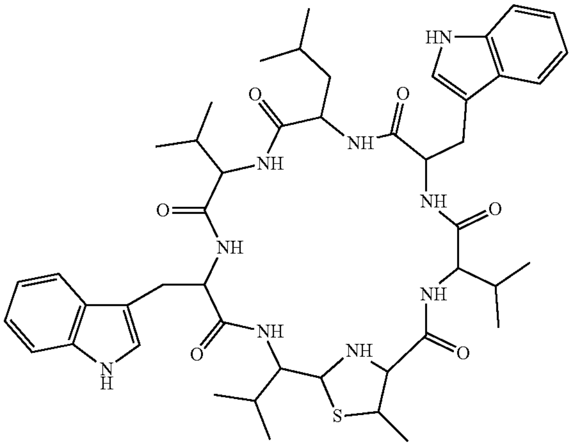
I.9a
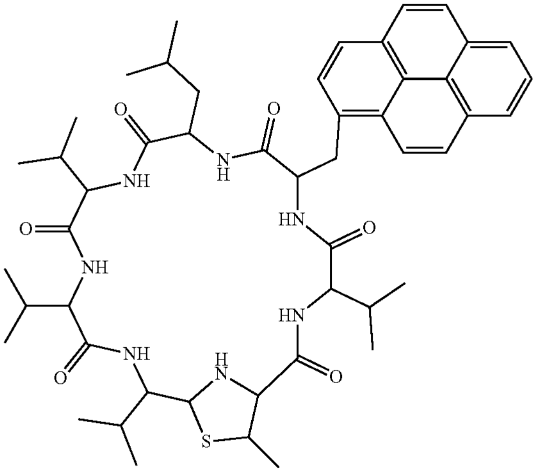
-continued
I.10a
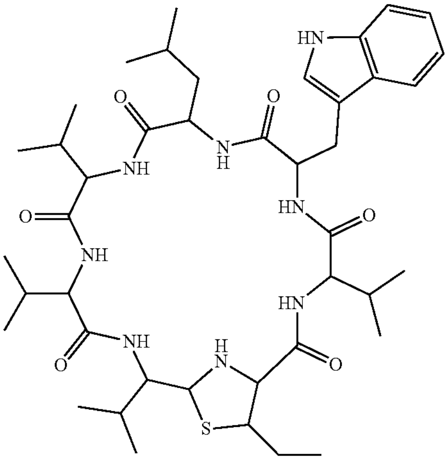
I.11a
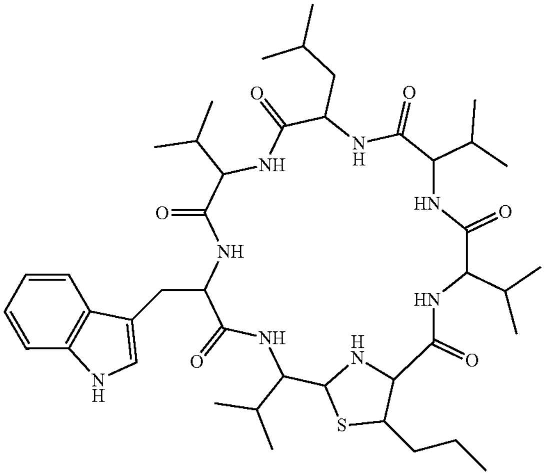
I.12a
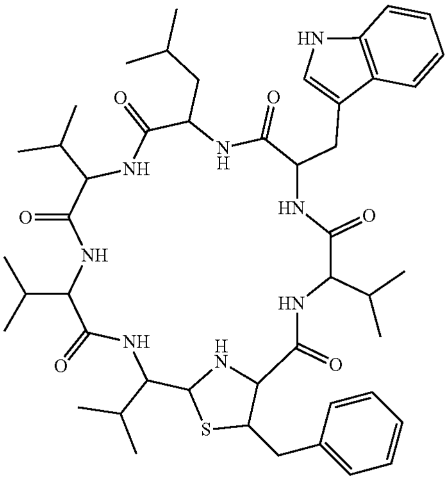

-continued
I.13a
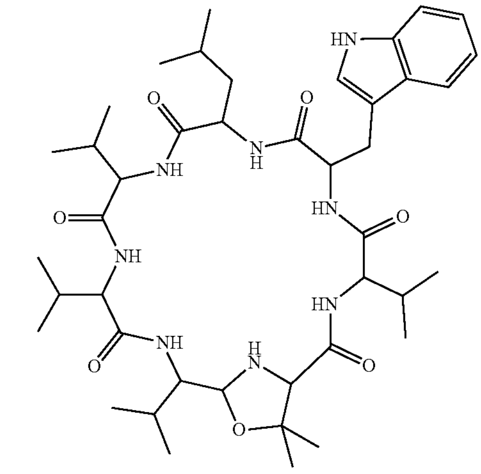
I.14a
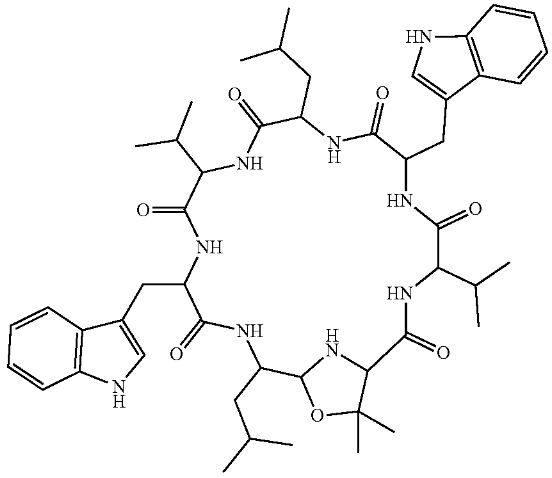
I.15a
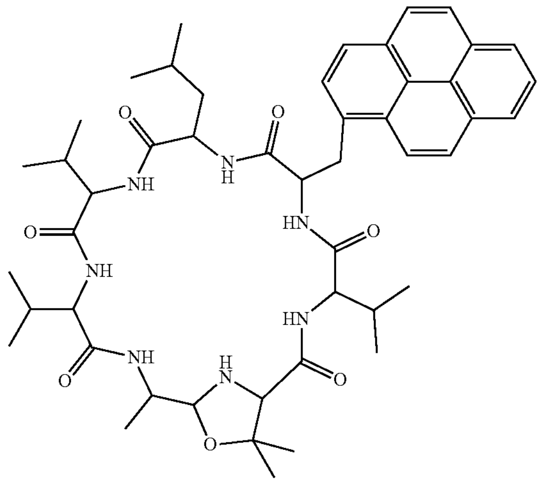
-continued
I.16a
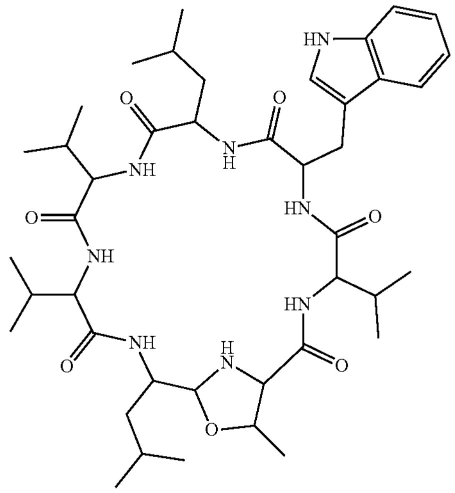
I.17a
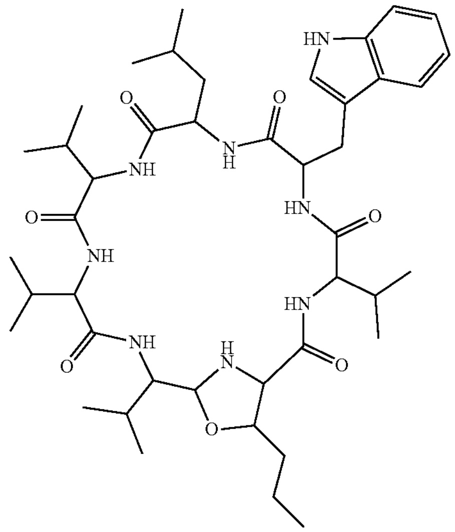
I.18a
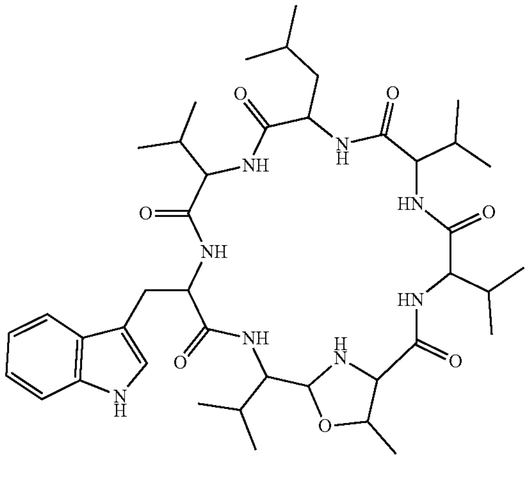

-continued
I.19a
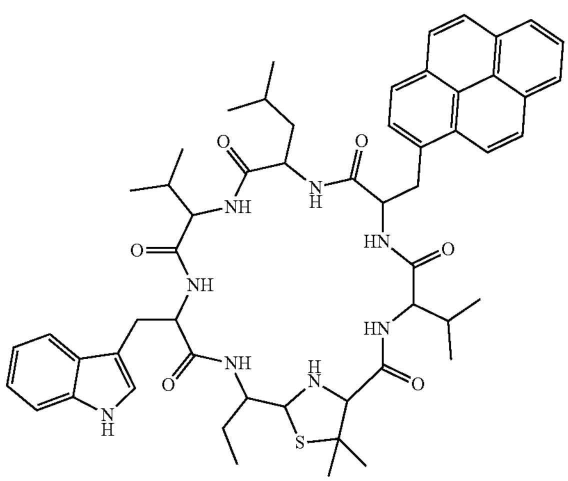
I.20a
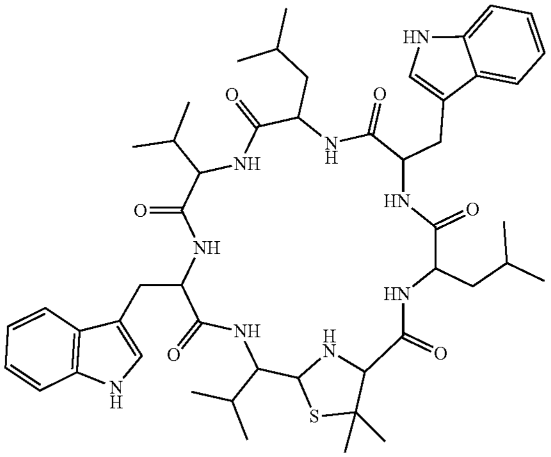
I.21a
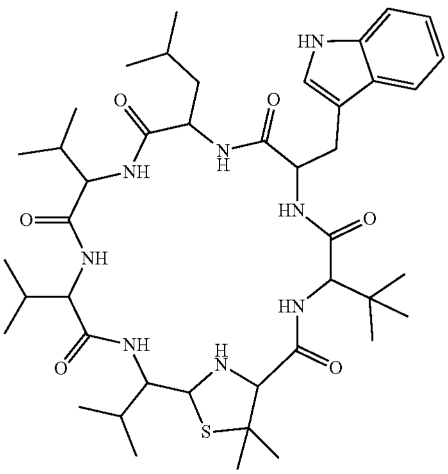
-continued
I.22a
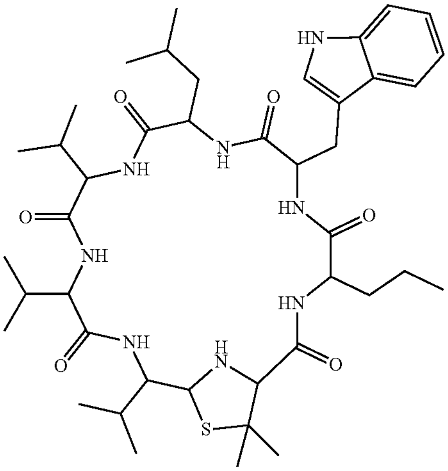
I.23a
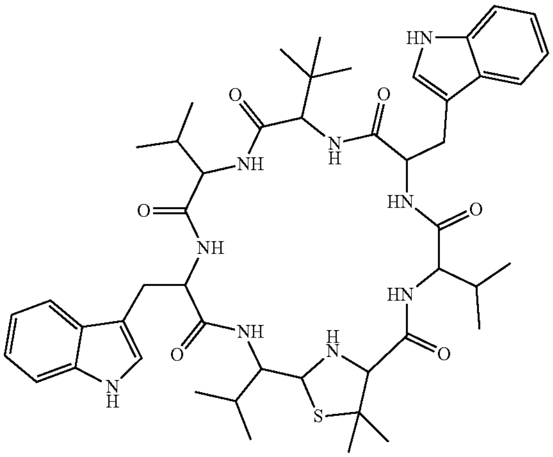
I.24a
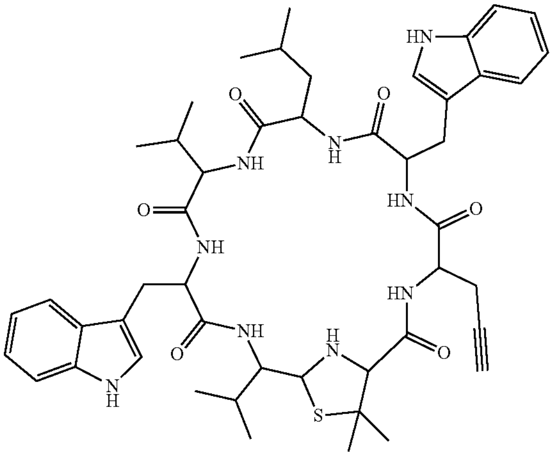
In further specific preferred embodiments, the cyclic compound of formula (I) is characterized by any one of the following formulae I.1 to I.24:

-continued
I.1
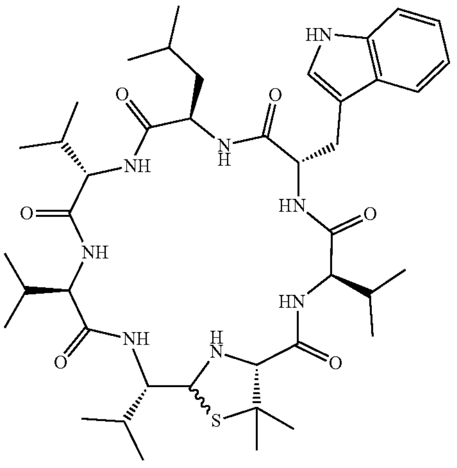
I.2
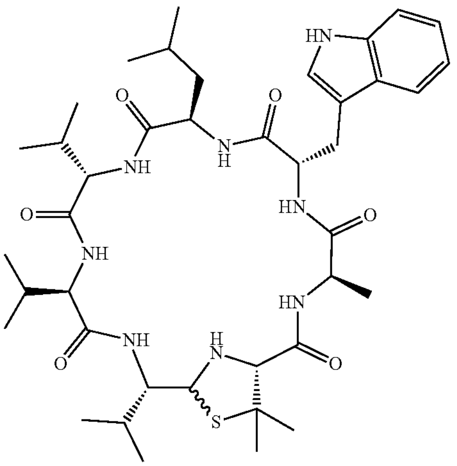
I.3
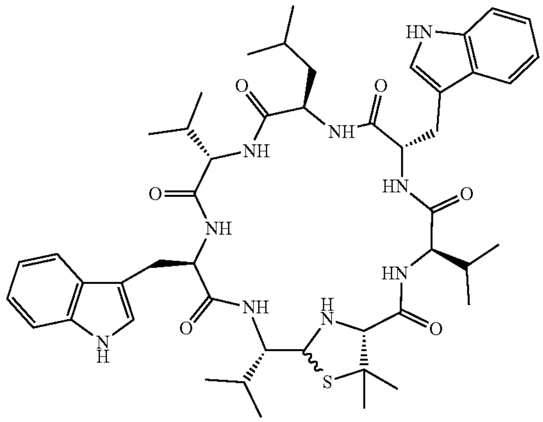
I.4
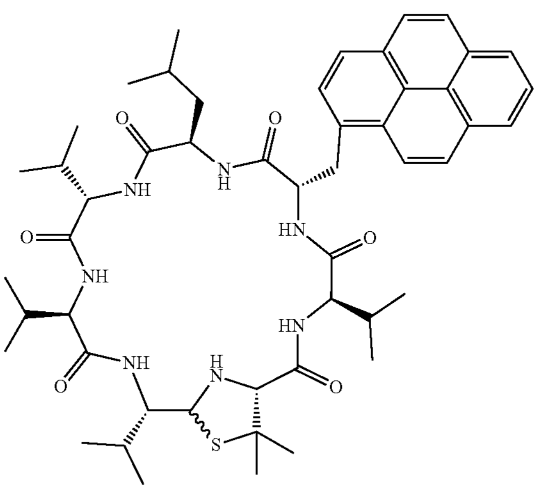
I.5
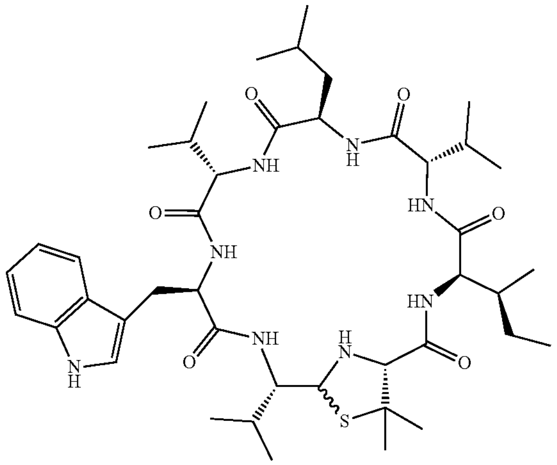
I.6
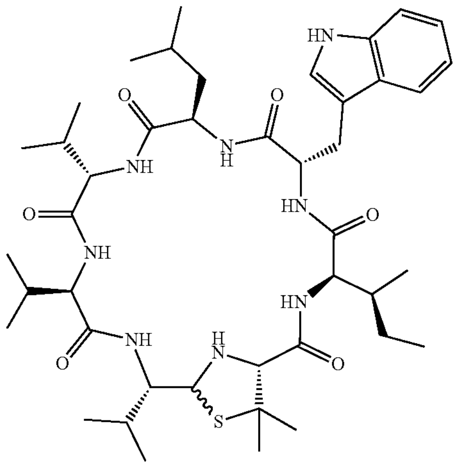

-continued
I.7
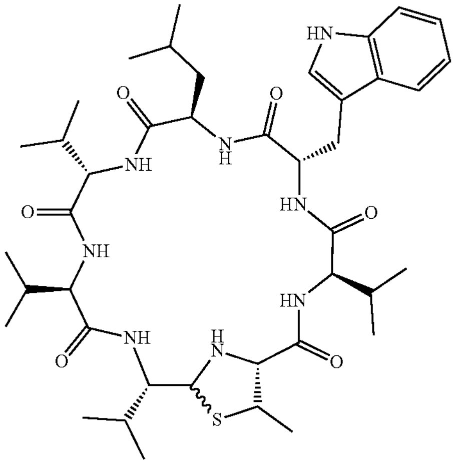
I.8
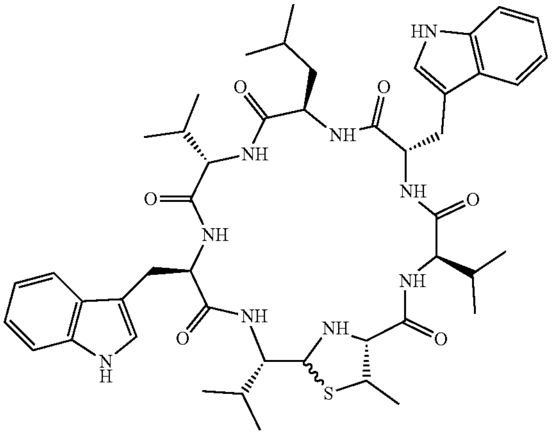
I.9
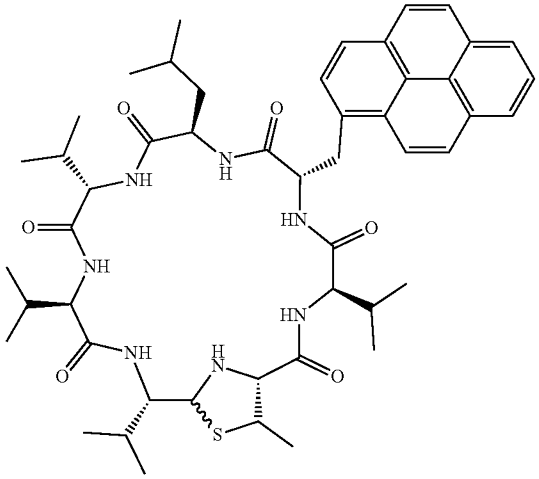
-continued
I.10
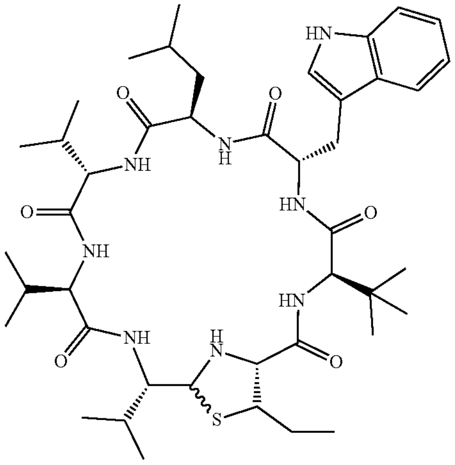
I.11
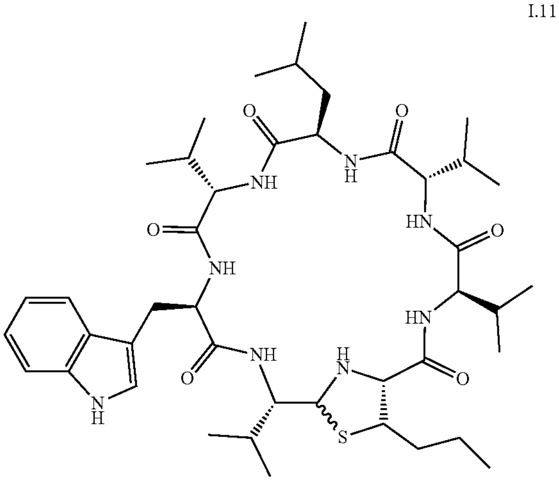
I.12
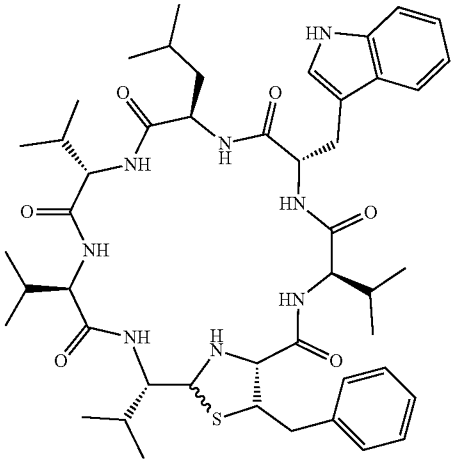

I.13
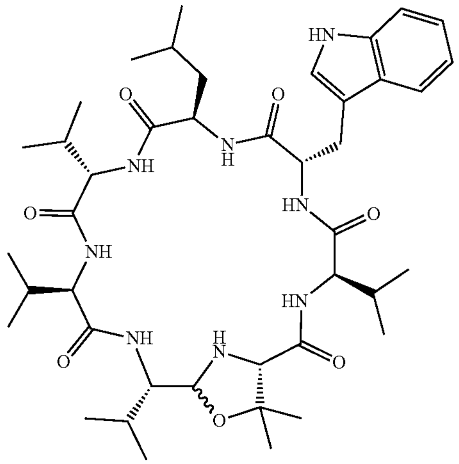
I.14
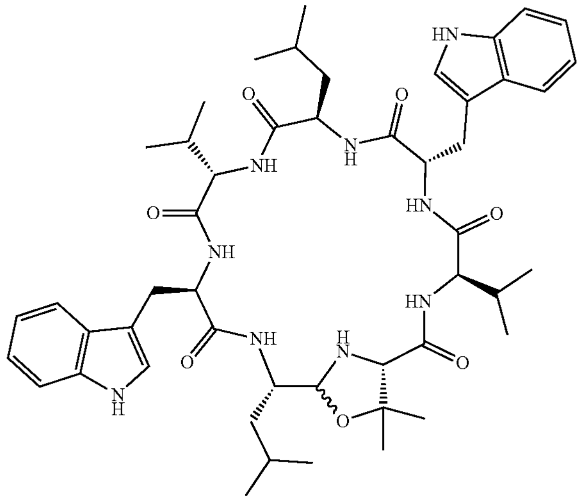
I.15
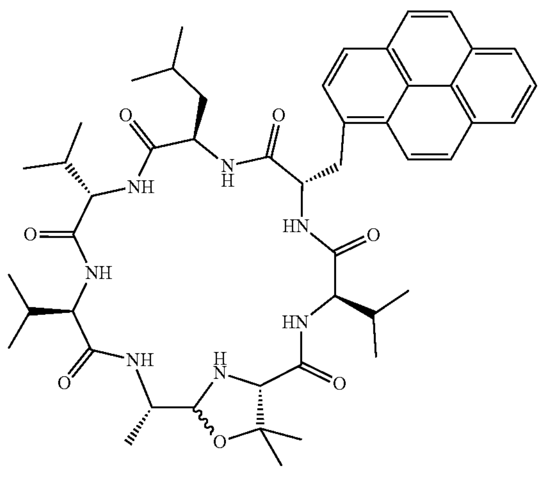
I.16
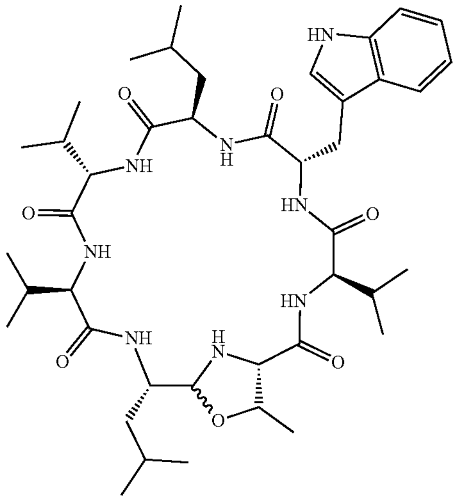
I.17
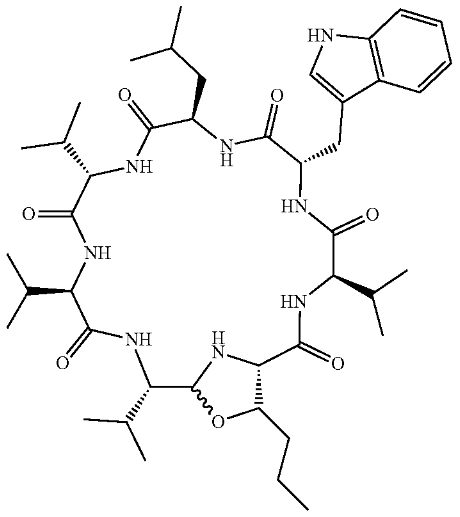
I.18
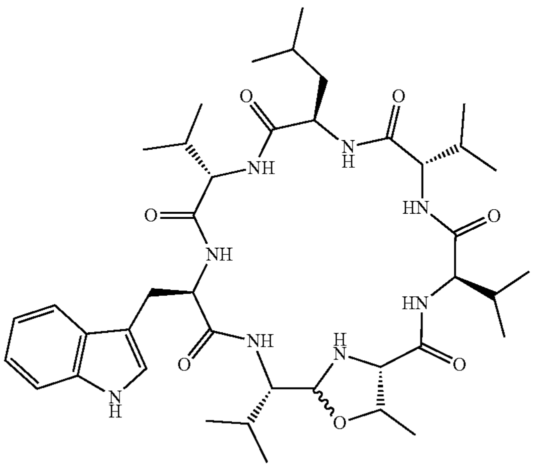

-continued

I.19

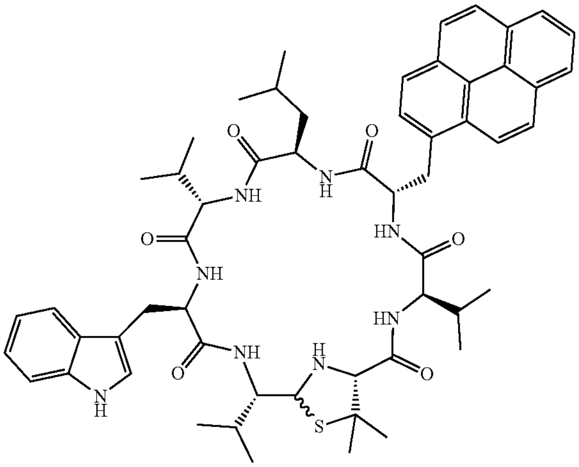

I.20

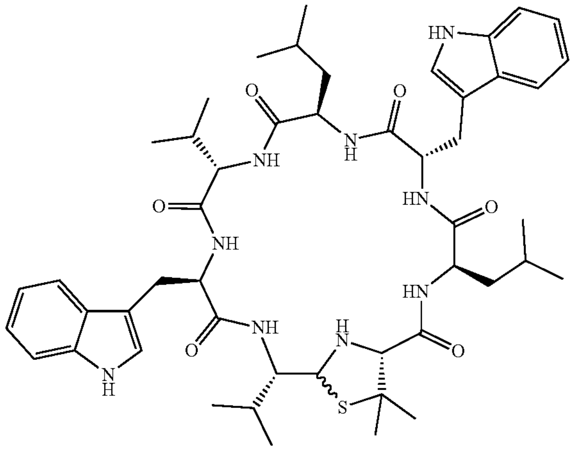

I.21

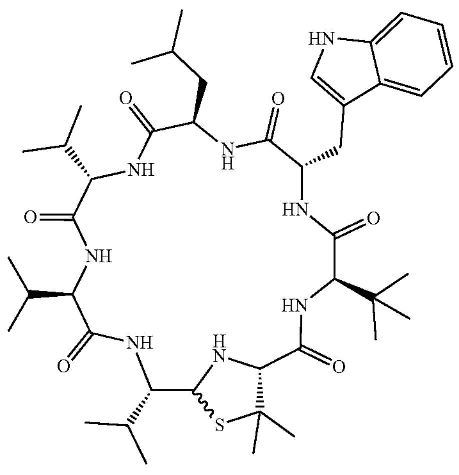

-continued

I.22

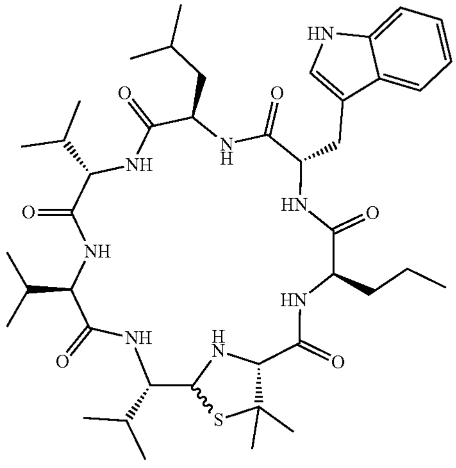

I.23

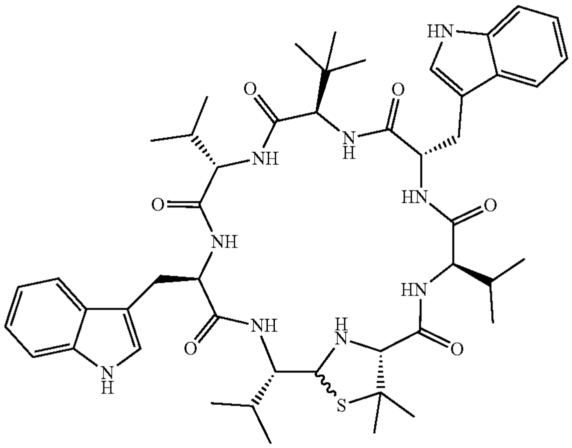

I.24

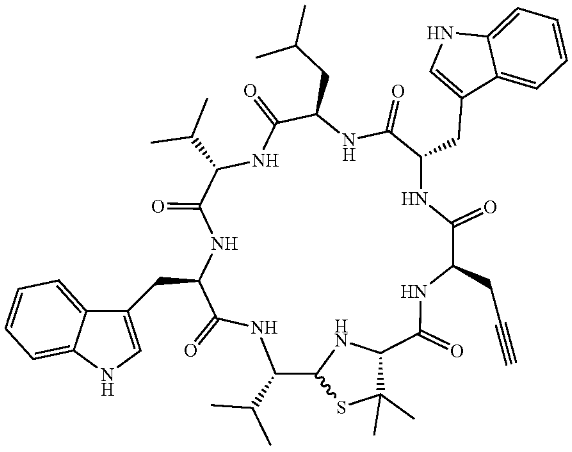

Particularly preferred are the cyclic compounds of formula I.1a to I.4a or I.1 to I.4. as well as the cyclic compounds of formula I.19a to I.24a or I.19 to I.24, respectively. In still further specific preferred embodiments, an oxazolidine ring is present in formulae I.14a to I.18a or I.14 to I.18 instead of a thiazolidine ring.

Surprisingly, the present inventors have found that the compound of formula (I) according to the invention has a number of advantageous properties, particularly for cosmetic use. For example, the cyclic compound of formula (I)

according to the invention exhibits excellent antimicrobial activity, in particular also antiviral and/or non-selective antibacterial activity. For this reason, the compound of formula (I) according to the invention is excellently suited, for example, for use as a cosmetic active ingredient in cosmetic preparations, in particular for topical application, where it can unfold its antimicrobial, in particular antiviral, (non-selective) antibacterial and/or antifungal, preferably antiviral and/or non-selective antibacterial, properties.

For example, it was surprisingly found that the cyclic compound of formula (I) according to the invention exhibits non-selective antimicrobial, in particular non-selective antibacterial activity, preferably specifically against Gram-positive bacteria. Preferably, on the other hand, the cyclic compounds according to the invention exhibit no or only minimal antibacterial activity against Gram-negative bacteria. By a "non-selective antimicrobial activity" it is preferably understood in the present context that the cyclic compound of formula (I) according to the invention has a broad antimicrobial effect on a wide variety of microbes (i.e., non-specific). By "non-selective antibacterial activity" it is preferably to be understood in the present context that the cyclic compound of formula (I) according to the invention has a broad antibacterial effect against a wide variety of bacteria (i.e. non-specific), but preferably specifically against Gram-positive bacteria, but preferably not or only minimally (i.e. not noteworthy) against Gram-negative bacteria.

Furthermore, the cyclic compound of formula (I) according to the invention has a supportive effect on the innate immune response.

In addition, it was surprisingly found that the non-selectively antibacterially active cyclic compound of formula (I) according to the invention, when used, does not lead to any, or only to an extremely small extent, to formation of resistance; the cyclic compound of formula (I) according to the invention in particular, for example, does not exhibit any relevant formation of resistance, whereas the compound lugdunin known from the prior art does, and thus there is a significant difference with regard to the formation of resistance. In this context, the term "formation of resistance" is to be understood in a manner known to the person skilled in the art and preferably with reference to antimicrobial, in particular antibacterial, activity. Surprisingly, it was found that the compound of formula (I) according to the invention differs from the known compound lugdunine, for example, with respect to the mode of action.

In a preferred embodiment of the present invention, the compound of formula (I) according to the invention exhibits antimicrobial, in particular antiviral, antibacterial and/or antifungal, preferably antiviral and/or non-selective antibacterial (preferably against Gram-positive bacteria, but preferably not or only minimally [i.e. not noteworthy, e.g. with an at least 10-fold, preferably at least 20-fold, more preferably at least 30-fold, etc., greater minimum inhibitory concentration (MIC) compared to Gram-positive bacteria] against Gram-negative bacteria), activity, and/or has a supportive effect on the innate immune response (e.g. of the skin).

In a particularly preferred embodiment, the compound of formula (I) according to the invention, for example in topic use in a cosmetic preparation on the skin, exhibits antiviral, antibacterial and/or antifungal, preferably antiviral and/or non-selective antibacterial (preferably only against Gram-positive bacteria, but preferably not or only minimally (i.e. not noteworthy) against Gram-negative bacteria), activity, and/or has a supportive effect on the innate immune response (e.g. of the skin).

Thiazolidine or Oxazolidine Building Block of Formula (H)

In a second aspect, the present invention is directed to a novel thiazolidine or oxazolidine building block of formula (II):

(II)

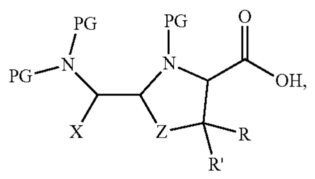

wherein:

Z is equal to O or S;

R and R' each are selected from the group consisting of H, methyl, ethyl, n-propyl, 1-methylethyl, n-butyl, 2-methylpropyl, 1-methylpropyl, benzyl and propargyl, with the proviso that when R is H, R' is not H;

PG each represents H or a protecting group, wherein individual PG may be the same or different, and wherein the protecting group is preferably selected from the group consisting of 9-fluorenylmethoxycarbonyl (Fmoc), tert-butyloxycarbonyl (Boc), benzyloxycarbonyl (Cbz), benzyl (Bn), trityl (Trt), acetyl (Ac) and tosyl (Ts);

X is selected from the group consisting of: Methyl, ethyl, n-propyl, 2-propenyl, 1-methylethyl, n-butyl, 2-methylpropyl, 1-methylpropyl, 1,1-dimethylethyl, n-pentyl, 3-methylbutyl, benzyl (Bn), propargyl, 1H-indole-3-ylmethyl, 1N-methyl-1H-indole-3-ylmethyl, 3-benzothienylmethyl, 1-naphthylmethyl, 9-anthracenylmethyl and pyrenylmethyl;

the C atom, which is bound to substituent X, and the C atom in position 4 of the thiazolidine or oxazolidine ring have the same absolute stereochemical configuration when Z is equal to O and an opposite absolute stereochemical configuration when Z is equal to S;

with the proviso that, when Z is equal to S and X is equal to methyl, benzyl or 1H-indole-3-ylmethyl, R is not methyl;

and the salts thereof, the solvates thereof, and the solvates of the salts thereof.

The thiazolidine or oxazolidine building block of formula (II) according to the invention is characterized in particular by excellent solubility and stability in organic solvents and, associated therewith, superior coupling properties when introduced as a building block in a solid-phase synthesis. This is particularly advantageous because it allows to prepare the cyclic compounds of formula (I) completely via solid-phase synthesis from amino acid derivatives and a thiazolidine or oxazolidine building block, except for the cyclization.

In a particularly preferred embodiment of the thiazolidine or oxazolidine building block according to the invention, Z is equal to S. In an alternative preferred embodiment of the cyclic compound of formula (I) according to the invention, Z is equal to O.

R and R' each are selected from the group consisting of H, methyl, ethyl, n-propyl, 1-methylethyl, n-butyl, 2-methylpropyl, 1-methylpropyl, benzyl and propargyl, with the proviso that when R is equal to H, R' is not H. This means that, for example, R can be equal to H and R' can be equal to methyl, or also, for example, R and R' can both be equal to methyl, but not, for example, R and R' can be equal to H, etc. In a preferred embodiment of the thiazolidine or oxazolidine building block according to the invention, R and R' are each selected from the group consisting of H, methyl, ethyl, n-propyl, 1-methylethyl, benzyl and propargyl. In another preferred embodiment of the cyclic compound of formula (I) according to the invention, R and R' each are selected from the group consisting of H, methyl, ethyl, and propargyl.

PG each represents H or a protecting group, wherein individual PGs may be the same or different, such that, for example, one or more PGs may represent H and one or more PGs may represent protecting groups, wherein the protecting groups may be the same or different. That is, in the thiazolidine or oxazolidine building block of formula (II), all three substituents PG may represent H, or two substituents PG may represent H, in which case one substituent PG represents a protecting group (preferably than a PG of the terminal amino group), or in that one substituent PG can stand for an H, in which case two substituents PG stand for protecting groups (preferably then the two PG of the terminal amino group), or in that all three substituents PG can stand for a protecting group, in which case the different protecting groups can be identical or different. Preferably, in the thiazolidine or oxazolidine building block of formula (II), two substituents PG represent H and one substituent PG (preferably in the terminal amino group) represents a protecting group.

Suitable protecting groups and their use for the (temporary) protection of certain functional groups are known to the skilled person. Protecting groups suitable for the purposes of the present invention are preferably common amino-protecting groups. Examples of protecting groups suitable for the present invention are 9-fluorenylmethoxycarbonyl (Fmoc), tert-butyloxycarbonyl (Boc), benzyloxycarbonyl (Cbz), tosyl (Ts, 4-methylphenylsulfonyl), benzyl (Bn), acetyl (Ac) and trityl (Trt).

According to the invention, the protecting group(s) is/are preferably selected from the group consisting of 9-fluorenylmethoxycarbonyl (Fmoc), tert-butyloxycarbonyl (Boc), benzyloxycarbonyl (Cbz), benzyl (Bn), trityl (Trt), acetyl (Ac) and tosyl (Ts). More preferably, the protecting group(s) is/are selected from 9-fluorenylmethoxycarbonyl (Fmoc), tert-butyloxycarbonyl (Boc), benzoyloxycarbonyl (Cbz), benzyl (Bn) and trityl (Trt), even more preferably from 9-fluorenylmethoxycarbonyl (Fmoc) and tert-butyloxycarbonyl (Boc). A particularly preferred protecting group is 9-fluorenylmethoxycarbonyl (Fmoc).

In a preferred embodiment of the thiazolidine or oxazolidine building block of formula (II) according to the invention, said substituent PG which is directly linked to the thiazolidine or oxazolidine ring is H, and the two substituents PG which are linked to the terminal amino group (i.e. not directly to the thiazolidine or oxazolidine ring) are H and a protecting group or two protecting groups, more preferably H and a protecting group. The protecting groups are thereby selected as set forth above.

In the thiazolidine or oxazolidine building block of formula (II) according to the invention, X is selected from the group consisting of methyl, ethyl, n-propyl, 2-propenyl, 1-methylethyl, n-butyl, 2-methylpropyl, 1-methylpropyl, 1,1-dimethylethyl, n-pentyl, 3-methylbutyl, benzyl (Bn), propargyl, 1H-indole-3-ylmethyl, 1N-methyl-1H-indole-3-ylmethyl, 3-benzothienylmethyl, 1-naphthylmethyl, 9-anthracenylmethyl, and pyrenylmethyl (wherein 1-pyrenylmethyl or 2-pyrenylmethyl, more preferably 1-pyrenylmethyl is selected as pyrenylmethyl). In a preferred embodiment of the thiazolidine or oxazolidine building block of formula (II) according to the invention, X is selected from the group consisting of ethyl, n-propyl, 2-propenyl, 1-methylethyl, n-butyl, 2-methylpropyl, 1-methylpropyl, 1,1-dimethylethyl, n-pentyl, 3-methylbutyl, benzyl, propargyl, 1N-methyl-1H-indole-3-ylmethyl, 3-benzothienylmethyl, 1-naphthylmethyl, 9-anthracenylmethyl and pyrenylmethyl (preferably 1-pyrenylmethyl or 2-pyrenylmethyl, in particular 1-pyrenylmethyl).

In another preferred embodiment, X is selected from the group consisting of n-propyl, 1-methylethyl, n-butyl, 2-methylpropyl, 1-methylpropyl, 1,1-dimethylethyl, benzyl, propargyl, and pyrenylmethyl (preferably 1-pyrenylmethyl or 2-pyrenylmethyl, in particular 1-pyrenylmethyl). In still another preferred embodiment, X is selected from the group consisting of 1-methylethyl, 2-methylpropyl, 1-methylpropyl, 1,1-dimethylethyl, benzyl, propargyl, and pyrenylmethyl (preferably 1-pyrenylmethyl or 2-pyrenylmethyl, in particular 1-pyrenylmethyl). In an alternatively preferred embodiment, X is selected from the group consisting of n-propyl, 1-methylethyl, n-butyl, 2-methylpropyl, 1-methylpropyl, 1,1-dimethylethyl, n-pentyl, and 3-methylbutyl.

With regard to suitable salts, solvates and solvates of the salts for the thiazolidine or oxazolidine building block of formula (II), the above statements with respect to compound of formula (I) according to the invention apply analogously.

In the thiazolidine or oxazolidine building block of formula (II) according to the invention, the C atom linked to substituent X and the C atom in position 4 of the thiazolidine or oxazolidine ring have the same absolute stereochemical configuration when Z is equal to O (i.e. if it is an oxazolidine ring) and an opposite absolute stereochemical configuration when Z is equal to S (i.e. if it is a thiazolidine ring). In this regard, the terms "opposite absolute stereochemical configuration" and "same absolute stereochemical configuration" are to be understood as defined above in the first aspect. That is, for example, if a thiazolidine or oxazolidine building block according to the invention has an oxazolidine ring and this has an R-configuration in position 4, also the C-atom linked to substituent X has an R-configuration, or, respectively if a thiazolidine or oxazolidine building block according to the invention has a thiazolidine ring and this has an R-configuration in position 4, the C-atom linked to substituent X has an S-configuration.

In specific preferred embodiments, the thiazolidine or oxazolidine building block of formula (II) according to the invention is characterized by one of formulae II.1 to II.39:

(II.1)

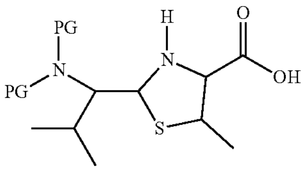

(II.2)

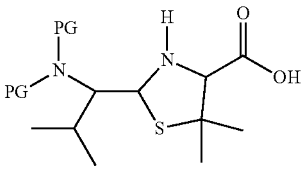

-continued
(II.3)
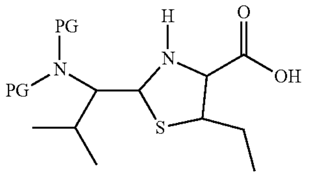
(II.4)
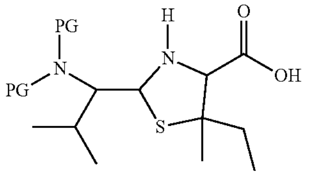
(II.5)
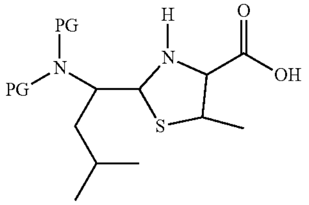
(II.6)
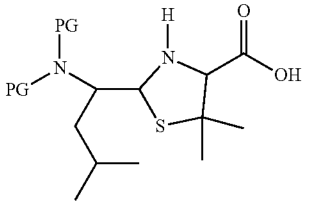
(II.7)
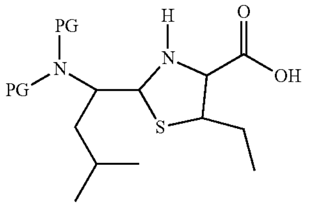
(II.8)
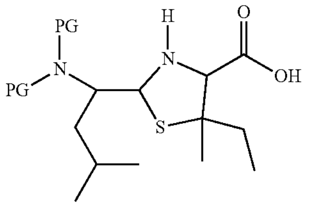
(II.9)
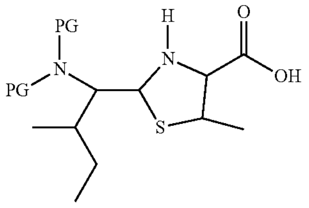
-continued
(II.10)
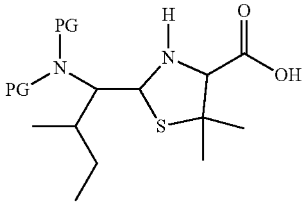
(II.11)
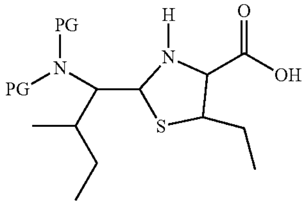
(II.12)
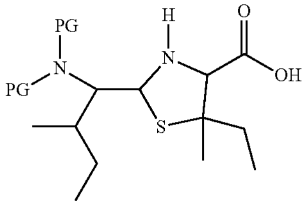
(II.13)
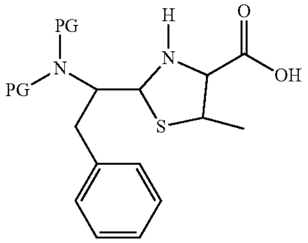
(II.14)
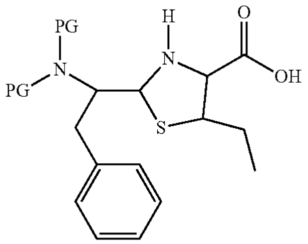
(II.15)
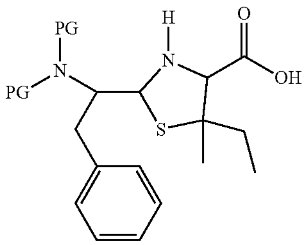

-continued
(II.16)
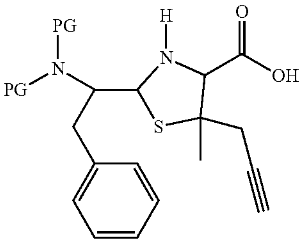
(II.17)
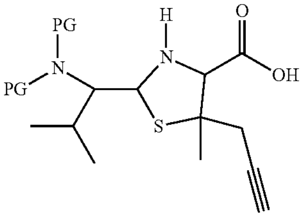
(II.18)
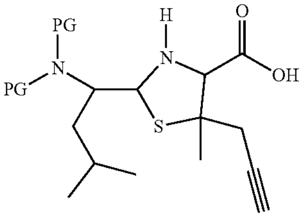
(II.19)
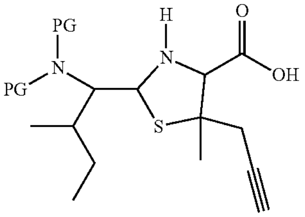
(II.20)
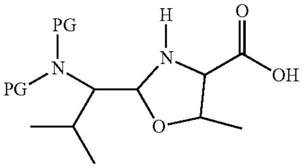
(II.21)
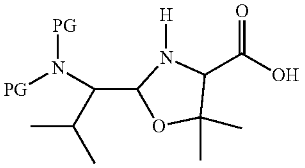
(II.22)
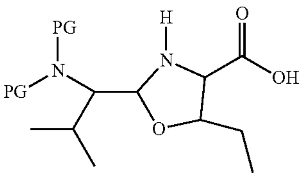
-continued
(II.23)
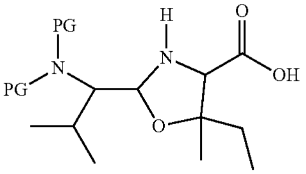
(II.24)
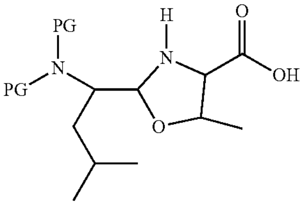
(II.25)
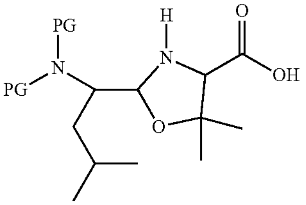
(II.26)
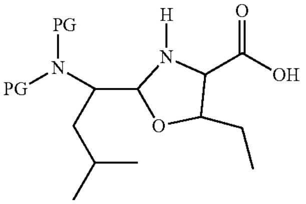
(II.27)
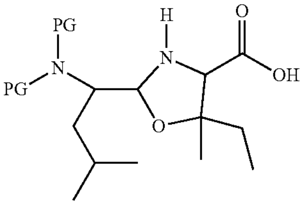
(II.28)
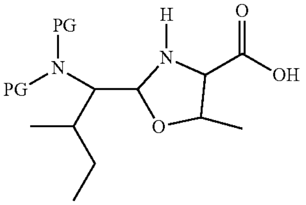
(II.29)
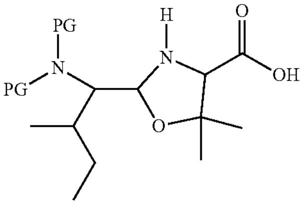

-continued (II.30)

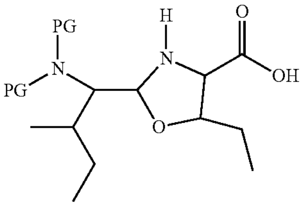

(II.31)

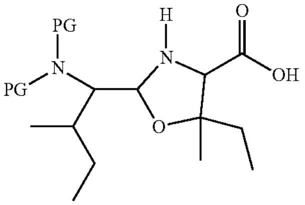

(II.32)

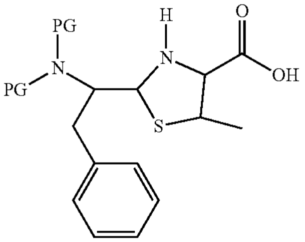

(II.33)

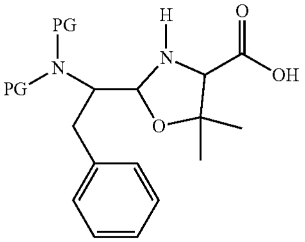

(II.34)

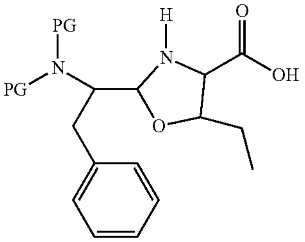

(II.35)

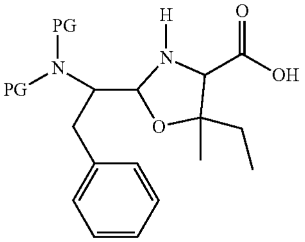

-continued (II.36)

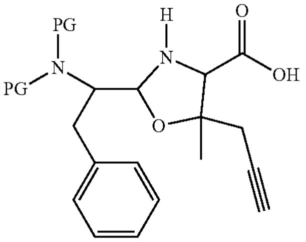

(II.37)

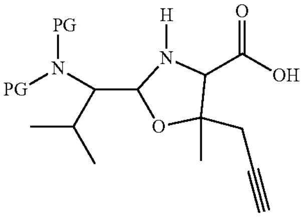

(II.38)

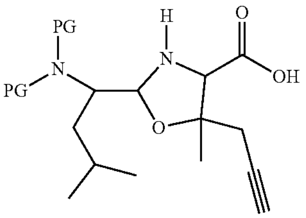

(II.39)

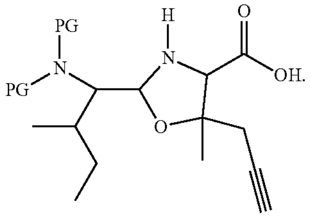

Method for the Synthesis of a Thiazolidine or Oxazolidine Building Block of Formula (II)

In a third aspect, the present invention is directed to a method for the synthesis of a thiazolidine or oxazolidine building block of formula (II) according to the invention, comprising the following steps (a) to (d):

(a) Providing a protected amino acid derivative of formula (III):

(III)

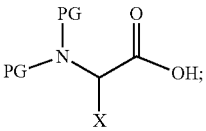

(b) Reducing the amino acid derivative (III) of step (a) to the alcohol of formula (IV) by (b1) in a first activation step, activating the amino acid derivative of formula (III), with an activating reagent, preferably selected from the group consisting of ethylene dimethylamino propyl carbodiimide (EDC), dieethylamino sulfur trifluoride (DAST), N-hydroxysuccinimide (NHS), propane phosphoric anhydride (T3P), thionyl chloride, ethylene chloroformate, oxalyl chloride, N,O-dimethylhydroxylamine (Weinreb amide), or 1,1'-carbonyldiimidazole (CDI), in an inert solvent; and (b2) in a second step, reducing the activation product of step (b1) to a compound of formula (IV):

(IV)

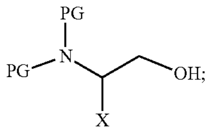

(c) Oxidizing the compound (IV) of step (b), with an oxidizing agent, in one or more aprotic solvents, and optionally an addition of water, to give the corresponding aldehyde of formula (V):

(V)

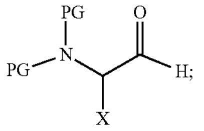

(d) Reacting (condensation) the compound (V) of step (c), preferably in a solvent mixture of water and a polar-protic solvent, preferably in a water:polar-protic solvent ratio of at most 1:1 (v/v) and at a reaction temperature of at least 30° C., with a compound of formula (VI):

(VI)

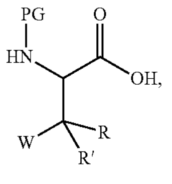

to obtain a thiazolidine or oxazolidine building block of formula (I) according to the invention;

wherein:

W is equal to SH or OH;

R and R' each are selected from the group consisting of H, methyl, ethyl, n-propyl, 1-methylethyl, n-butyl, 2-methylpropyl, 1-methylpropyl, benzyl and propargyl, with the proviso that when R is equal to H, R' is not H;

PG each represents H or a protecting group, wherein individual PG may be the same or different, and wherein the protecting group is preferably selected from the group consisting of 9-fluorenylmethoxycarbonyl (Fmoc), tert-butyloxycarbonyl (Boc), benzyloxycarbonyl (Cbz), benzyl (Bn), trityl (Trt), acetyl (Ac) and tosyl (Ts);

X is selected from the group consisting of: methyl, ethyl, n-propyl, 2-propenyl, 1-methylethyl, n-butyl, 2-methylpropyl, 1-methylpropyl, 1,1-dimethylethyl, n-pentyl, 3-methylbutyl, benzyl, propargyl, 1H-indole-3-ylmethyl, 1N-methyl-1H-indole-3-ylmethyl, 3-benzothienylmethyl, 1-naphthylmethyl, 9-anthracenylmethyl and pyrenylmethyl;

with the proviso that when Z is equal to S and X is equal to methyl, benzyl or 1H-indole-3-ylmethyl, R is not methyl.

In step (a) of the method, a protected amino acid derivative of formula (III) is provided as the starting substance. Here, PG each represents H or a protecting group, wherein individual PGs may be the same or different, and wherein the protecting group is preferably selected from the group of common amino protecting groups, such as 9-fluorenylmethoxycarbonyl (Fmoc), tert-butyloxycarbonyl (Boc), benzyloxycarbonyl (Cbz), benzyl (Bn), trityl (Trt), acetyl (Ac) and tosyl (Ts).

In a preferred embodiment, in the protected amino acid derivative of formula (III), a substituent PG represents H and a substituent PG represents a protecting group, preferably selected from the group consisting of 9-fluorenylmethoxycarbonyl (Fmoc), tert-butyloxycarbonyl (Boc), benzyloxycarbonyl (Cbz), benzyl (Bn), trityl (Trt), acetyl (Ac), and tosyl (Ts), more preferably selected from 9-fluorenylmethoxycarbonyl (Fmoc), tert-butyloxycarbonyl (Boc), benzyloxycarbonyl (Cbz), benzyl (Bn), and trityl (Trt), even more preferably selected from 9-fluorenylmethoxycarbonyl (Fmoc), tert-butyloxycarbonyl (Boc), most preferably 9-fluorenylmethoxycarbonyl (Fmoc). In an alternative preferred embodiment, in the protected amino acid derivative of formula (III), both substituents PG represent protecting groups, wherein the protecting groups are preferably selected from the above group and wherein the two protecting groups may be the same or different, and are preferably the same.

The substituent X of the protected amino acid derivative of formula (III) is selected from the group consisting of methyl, ethyl, n-propyl, 2-propenyl, 1-methylethyl, n-butyl, 2-methylpropyl, 1-methylpropyl, 1,1-dimethylethyl, n-pentyl, 3-methylbutyl, benzyl (Bn), propargyl, 1H-indole-3-ylmethyl, 1N-methyl-1H-indole-3-ylmethyl, 3-benzothienylmethyl, 1-naphthylmethyl, 9-anthracenylmethyl, and pyrenylmethyl (wherein the pyrenylmethyl preferably is 1-pyrenylmethyl or 2-pyrenylmethyl, in particular 1-pyrenylmethyl).

In a preferred embodiment of the method, X is selected from the group consisting of ethyl, n-propyl, 2-propenyl, 1-methylethyl, n-butyl, 2-methylpropyl, 1-methylpropyl, 1,1-dimethylethyl, n-pentyl, 3-methylbutyl, benzyl, propargyl, 1N-methyl-1H-indole-3-ylmethyl, 3-benzothienylmethyl, 1-naphthylmethyl, 9-anthracenylmethyl, and pyrenylmethyl (preferably 1-pyrenylmethyl or 2-pyrenylmethyl, in particular 1-pyrenylmethyl). In another preferred embodiment, X is selected from the group consisting of n-propyl, 1-methylethyl, n-butyl, 2-methylpropyl, 1-methylpropyl, 1,1-dimethylethyl, benzyl, propargyl, and pyrenylmethyl (preferably 1-pyrenylmethyl or 2-pyrenylmethyl, in particular 1-pyrenylmethyl). In still another preferred embodiment, X is selected from the group consisting of 1-methylethyl, 2-methylpropyl, 1-methylpropyl, 1,1-dimethylethyl, benzyl, propargyl, and pyrenylmethyl (preferably 1-pyrenylmethyl or 2-pyrenylmethyl, in particular 1-pyrenylmethyl). In an alternatively preferred embodiment, X is selected from the group consisting of n-propyl, 1-methylethyl, n-butyl, 2-methylpropyl, 1-methylpropyl, 1,1-dimethylethyl, n-pentyl, and 3-methylbutyl.

The substituents R and R' of the protected amino acid derivative of formula (III) of step (a) each are selected from the group consisting of H, methyl, ethyl, n-propyl, 1-methylethyl, n-butyl, 2-methylpropyl, 1-methylpropyl, benzyl and propargyl, with the proviso that when R is equal to H, R' is not H. In a preferred embodiment of this method, R and R' each are selected from the group consisting of H, methyl, ethyl, n-propyl, 1-methylethyl, benzyl and propargyl. In another preferred embodiment of this method, R and R' each are selected from the group consisting of H, methyl, ethyl, and propargyl.

The substituent W is equal to SH or OH. In a particularly preferred embodiment of this method, W is equal to SH. In an alternative preferred embodiment of this method, W is equal to OH.

In step (b) of the method, the amino acid derivative of formula (III) of step (a) is reduced to the alcohol of formula (IV). Suitable reaction conditions for step (b) are known to the skilled person. In this method, in an initial activation step (b1), the amino acid derivative of formula (III) is initially activated using an activating reagent which is preferably selected from the group consisting of ethylenedimethylamino-propylcarbodiimide (EDC), diethylaminosulfur trifluoride (DAST), N-hydroxysuccinimide (NHS), propane phosphoric anhydride (T3P), thionyl chloride, ethylene chloroformate, oxalyl chloride, N,O-dimethylhydroxylamine (Weinreb-amide), and 1,1'-carbonyldiimidazole (CDI), more preferably thionyl chloride, ethylene chloroformate, oxalyl chloride, and 1,1'-carbonyldiimidazole (CDI), more preferably 1,1'-carbonyldiimidazole (CDI), in an inert solvent.

As inert solvent preferably an inert ether solvent, more preferably an inert cyclic ether solvent is used. Preferably, the inert solvent used is diethyl ether, diisopropyl ether, methyl tert-butyl ether (MTBE), 1,4-dioxane, cyclopentyl methyl ether, 2-methyltetrahydrofuran (2-MHF), or tetrahydrofuran (THF), more preferably 1,4-dioxane, cyclopentyl methyl ether, 2-methyltetrahydrofuran (2-Me-THF), or tetrahydrofuran (THF), even more preferably THF. Mixtures of more than one inert solvent may also be used.

The initial activation step (b1) is preferably carried out at 15 to 25° C. for at least 5 min, more preferably for 10 to 30 min, even more preferably for 15 min. The activating reagent is added at least at 1 equiv, more preferably between 1.0 and 2.0 equiv, more preferably between 1.0 and 1.5 equiv, even more preferably at 1.3 equiv.

In a second step (b2), the activation product of step (b1), is reduced to a compound of formula (IV):

(IV)

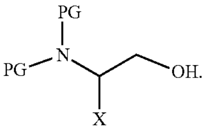

The term "activation product of step (b1)" is to be understood the product of the initial activation step (b1).

Suitable reducing agents for step (b2) are known to the skilled person. For example, $Pd/C/H_2$, Pd/C/triethylsilane, $NiCl_2/NaBH_4$, lithium aluminum hydride ($LiAlH_4$), diisobutyl aluminum hydride (DIBAL-H), sodium cyanoborohydride ($NaBH_3CN$) or sodium borohydride ($NaBH_4$), preferably $NaBH_3CN$ or $NaBH_4$, more preferably $NaBH_4$, can be used as reducing agents. Step (b2) is preferably carried out at a reaction temperature of 0° C. and for at least 15 min, more preferably 15-30 min, even more preferably 25 min.

In a preferred embodiment, in step (b2), the activation product of step (b1) is reduced using $NaBH_3CN$ or $NaBH_4$, preferably $NaBH_4$, at 0° C. for at least 15 min, more preferably 15 to 30 min, even more preferably for 25 min.

In step (c) of the method, compound (IV) of step (b) is oxidized with an oxidizing agent, in an aprotic solvent, and optionally an addition of water, to the corresponding aldehyde of formula (V):

(V)

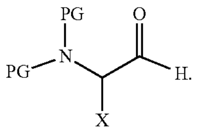

Suitable oxidizing agents and reaction conditions are known to the skilled person. Suitable oxidizing agents are, for example, pyridinium chlorochromate (PCC, $CrO_3$/pyridine), tetrapropylammonium perruthenate/N-methylmorpholine-N-oxide (TPAP/NMO), tetramethyl-piperidinyloxyl/sodium hypochlorite (TEMPO/NaOCl or Oxone), oxalyl chloride/DMSO/$NEt_3$ (Swern oxidation) and Dess-Martin-periodinane (DMP). Preferably, the oxidizing agent is selected to be oxalyl chloride/DMSO/$NEt_3$ or DMP, more preferably DMP.

Aprotic solvents are known to the skilled person. Mixtures of more than one aprotic solvent may also be used for step (c). For example, ethyl acetate, acetone, toluene, THF, chloroform, and/or dichloromethane (DCM) may be selected as the aprotic solvent. Preferred aprotic solvents are toluene, THF, chloroform, and DCM. Particularly preferred is DCM.

The oxidizing agent may be used at, for example, between 1.0 to 2.0 equiv., preferably between 1.0 to 1.5 equiv., more preferably between 1.4 to 1.5 equiv. To the reaction an addition of water can be added, preferably between 1.0 to 1.5 equiv., more preferably 1.1 equiv. As described in *Tetrahedron Lett.,* 2000, 41, 1359-1362 and *J. Org. Chem.,* 1994, 59, 7549-7552, an addition of water, for example, at 1 equiv. $H_2O$ favors and accelerates the reaction.

Preferably, the oxidizing agent and the optional addition of water are added over the first 15 to 90 min of the reaction, more preferably over the first 30 to 60 min, wherein the reaction time preferably is 1 to 40 hours, more preferably 2 to 24 hours, even more preferably 5 to 16 hours. Step (c) is preferably carried out at a reaction temperature of at least 10° C., more preferably 15 to 30° C., even more preferably 15 to 25° C.

The oxidizing agent is preferably used between 1.0 to 2.0 equiv., more preferably between 1.0 to 1.5 equiv., more preferably between 1.4 to 1.5 equiv. and is added to the reaction mixture for example over the first 30 min, preferably the first 15 min, more preferably the first 10 min of the reaction. To the reaction, preferably water is added, preferably at between 1.0 to 1.5 equiv., more preferably 1.1 equiv., over the first 15 to 90 min of the reaction, more preferably over the first 30 to 60 min, wherein the reaction time is 1 to 40 hours, more preferably 2 to 24 hours, more preferably 5 to 16 hours. The oxidation is preferably carried out at a reaction temperature of at least 10° C., more preferably 15 to 30° C., more preferably 15 to 25° C.

In the final step (d), compound (V) of step (c) is finally reacted (condensation), preferably in a solvent mixture of water and a polar-protic solvent, with a compound of formula (VI):

(VI)

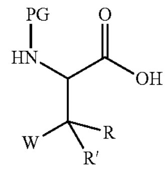

to obtain a thiazolidine or oxazolidine building block of formula (II) according to the invention.

Suitable polar-protic solvents for step (d) are for example formic acid, acetic acid, ethanol, isopropanol or methanol, preferably ethanol, isopropanol or methanol, more preferably methanol. If a solvent mixture of water and a polar-protic solvent is used, the ratio of water:polar-protic solvent in the solvent mixture is preferably ≤1:1 (v/v), more preferably 1:1 to 1:3 (v/v), even more preferably 1:2 (v/v).

The reaction temperature in step (d) is preferably at least 30° C., more preferably at least 50° C., even more preferably between 55° C. to 75° C., even more preferably between 55° C. to 65° C. The reaction time is preferably at least 6 hours, more preferably at least 15 hours, even more preferably between 15 to 30 hours, in particular preferably 24 hours.

In step (d), the reaction product from the reaction can be finally filtered, for example, preferably through a pore 4 frit, and then preferably be washed with at least 5-fold excess, more preferably 10-fold excess of water relative to the reaction solvent volume.

In a preferred embodiment, in step (d), a solvent mixture of water and a polar-protic solvent is used, wherein the ratio of water to polar-protic solvent is ≤1:1 (v/v); the polar-protic solvent is formic acid, acetic acid, ethanol, isopropanol or methanol, more preferably ethanol, isopropanol or methanol, more preferably methanol; and/or the reaction is carried out at at least 50° C., more preferably between 55° C. to 75° C., and/or for at least 6 hours, more preferably between 15 to 30 hours.

With respect to the substituents and further parameters of the thiazolidine or oxazolidine building blocks of formula (II) prepared this way and the synthesis precursors thereof, the above-described with redard to the second aspect according to the invention applies accordingly.

Method for the Solid-Phase Peptide Synthesis of the Cyclic Compound (I) According to the Invention.

In a fourth aspect, the present invention is directed to a method for solid-phase peptide synthesis of a cyclic compound of formula (I) according to the invention, comprising the following steps (i) to (iv):

(i) Providing, bound to a solid phase via its terminal carboxyl group, an amino acid derivative of formula (VII):

(VII)

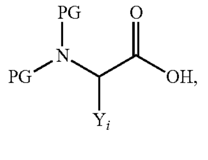

wherein i is equal to 1 to 5;

a linear peptide comprising/consisting of two, three, four or five amino acid derivatives of formula (VII); or a thiazolidine or oxazolidine building block of formula (II) as described in detail with respect to the second aspect of the present invention;

wherein the terminal amino group is protected by at least one protecting group;

(ii) Carrying out, starting from the amino acid derivative of formula (VII), the peptide, or the thiazolidine or oxazolidine building block of step (i), respectively, by carrying out one or more consecutive coupling reactions, adding in each case of one or more amino acid derivatives of formula (VII), one or more linear peptides comprising/consisting of two to five amino acid derivatives of formula (VII), or a thiazolidine or oxazolidine building block of formula (II) as described in detail with respect to the second aspect of the present invention, wherein the terminal amino group is protected by at least one protecting group, a stepwise solid phase synthesis of a linear compound, which is bound to the solid phase, comprising/consisting of five amino acid derivatives of formula (VII), wherein i is equal to 1 to 5, and a thiazolidine or oxazolidine building block of formula (II), as already described in detail with respect to the second aspect of the present invention;

(iii) Removing the protecting groups ("deprotecting") of the linear product of step (ii), which is bound to the solid phase, and cleaving it off from the solid phase to form a linear compound not bound to the solid phase; and (iv) Macrocyclization of the linear compound of step (iii), not bound to the solid phase, preferably by macrolactamization, thereby obtaining the cyclic compound of formula (I) according to the invention;

wherein:

X and $Y_1$ to $Y_5$ each are selected from the group consisting of: methyl, ethyl, n-propyl, 2-propenyl, 1-methylethyl, n-butyl, 2-methylpropyl, 1-methylpropyl, 1,1-dimethylethyl, n-pentyl, 3-methylbutyl, benzyl (Bn), propargyl, 1H-indole-3-ylmethyl, 1N-methyl-1H-indole-3-ylmethyl, 3-benzothienylmethyl, 1-naphthylmethyl, 9-anthracenylmethyl and pyrenylmethyl;

Z is equal to O or S;

PG each represents H or a protecting group, wherein individual PG may be the same or different, and wherein the protecting group is preferably selected from the group consisting of 9-fluorenylmethoxycarbonyl (Fmoc), tert-butyloxycarbonyl (Boc), benzyloxycarbonyl (Cbz), benzyl (Bn), trityl (Trt), acetyl (Ac) and tosyl (Ts);

R and R' each are selected from the group consisting of H, methyl, ethyl, n-propyl, 1-methylethyl, n-butyl, 2-methylpropyl, 1-methylpropyl, benzyl and propargyl, with the proviso that when R is H, R' is not H;

with the proviso that when X, $Y_1$, $Y_4$ and $Y_5$ are equal to 1-methylethyl, $Y_2$ is equal to 1H-indole-3-ylmethyl, $Y_3$ is equal to 2-methylpropyl, R is equal to H and R' is equal to methyl, Z is not O.

The method according to the invention for the solid-phase peptide synthesis of a cyclic compound of formula (I) according to the invention, in comparison with other methods known from the prior art for the preparation of cyclic peptide derivatives comprising an amino acid derivative building block with a thiazolidine or oxazolidine ring, provides for the distinct advantage that by using the thiazolidine or oxazolidine building block of formula (II) according to the invention as a concrete building block in the stepwise solid-phase peptide synthesis, the synthesis of the cyclic compound can be carried out bound to a solid phase up to the macrocyclization.

The novel synthetic route is based on the preparation of previously unknown alkyl, aryl or alkynyl heterocyclic amino acid derivatives, which are necessary for the first or second step, the novel thiazolidine and oxazolidine building blocks of formula (II), which are characterized in particular by excellent solubility and stability in organic solvents and associated superior coupling properties in solid-phase synthesis.

The synthesis of such thiazolidine and oxazolidine building blocks can thus be advantageously introduced for the first time into the efficient method of solid-phase peptide synthesis. This allows a simple, controlled and extremely efficient synthesis of the novel cyclic compounds of formula (I), by solid-phase peptide synthesis via a linear precursor (i.e. via a linear peptide derivative bound to the solid phase), and a simpler upscaling. Following established principles, the linear precursor can finally be cyclized to the cyclic compound in the final step under optimized conditions and be isolated with high purity (>90% purity) and high yield in optimized washing steps.

Despite the many synthetic risk factors, such as racemization, tautomerization, cleavage or other side reactions in the deprotection of intermediates and the like, in the synthesis of a complex molecule with many possible isomers, such as the cyclic compound of formula (I) according to the invention, it has been possible to find a preparation method for solid phase synthesis that allows to prepare the cyclic compound of formula (I) in high yield, purity and/or the required stereoisomeric purity, preferably all three. Based on this novel synthetic route, the synthesis of large quantities is possible and the preparation of products on an industrial scale is enabled, respectively, which preferably reduces the amount of side products and improves the yield.

The method according to the invention for the solid-phase peptide synthesis of a cyclic compound of formula (I) according to the invention comprises, in step (i), initially providing, bound to a solid phase via its terminal carboxyl group, an amino acid derivative of formula (VII):

(VII)

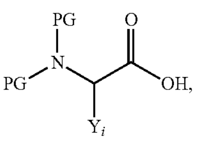

wherein i is equal to 1 to 5;

a linear peptide comprising/consisting of two, three, four or five amino acid derivatives of formula (VII); or of a thiazolidine or oxazolidine building block of formula (II), as already described in detail with respect to the second aspect of the present invention.

With respect to the amino acid derivative of formula (VII), $Y_1$ to $Y_5$ (i.e. $Y_i$ with i=1-5) each are selected from the group consisting methyl, ethyl, n-propyl, 2-propenyl, 1-methylethyl, n-butyl, 2-methylpropyl, 1-methylpropyl, 1,1-dimethylethyl, n-pentyl, 3-methylbutyl, benzyl (Bn), propargyl, 1H-indole-3-ylmethyl, 1N-methyl-1H-indole-3-ylmethyl, 3-benzothienylmethyl, 1-naphthylmethyl, 9-anthracenylmethyl and pyrenylmethyl (preferably 1-pyrenylmethyl or 2-pyrenylmethyl, in particular 1-pyrenylmethyl). With regard to the preferred embodiments of the substituents $Y_1$ to $Y_5$, the above-described with regard to the first aspect according to the invention applies accordingly.

With respect to the thiazolidine or oxazolidine building block of formula (II), the above-described with regard to the second aspect according to the invention applies accordingly.

With respect to the linear peptide consisting of two, three, four, or five amino acid derivatives of formula (VII), it goes without saying that the substituents $Y_1$ to $Y_5$ of the individual amino acid derivatives in the peptide are not the same among themselves (that is, only one amino acid derivative having substituent $Y_1$, only one amino acid derivative having $Y_2$, etc. is present in the linear peptide, wherein the individual substituents $Y_1$, $Y_2$, etc., but may represent the same or different residues as already described) and are also arranged in their sequence in such a way that, when carrying out the method according to the invention, with the aid of the peptide as a building block, a cyclic compound of formula (I) according to the invention (i.e. with the correct arrangement/sequence of the substituents X and $Y_1$-$Y_5$) can ultimately be synthesized. Preferably, the linear peptide consisting of two, three, four, or five amino acid derivatives of formula (VII) has also been prepared by solid-phase peptide synthesis.

The terminal amino group of the amino acid derivative of formula (VII), of the peptide or of the thiazolidine or oxazolidine building block in step (i) is protected by at least one protecting group, preferably protected by exactly one protecting group (i.e. the terminal amino group still has an N—H bond). Suitable protecting groups and their use for the (temporary) protection of certain functional groups, in particular in amino acid and peptide derivatives, are known to the skilled person.

The protecting groups suitable for the purposes of the present invention are preferably common amino protecting groups. According to the invention, the at least one protecting group is preferably selected from the group consisting of 9-fluorenylmethoxycarbonyl (Fmoc), tert-butyloxycarbonyl (Boc), benzyloxycarbonyl (Cbz), benzyl (Bn), trityl (Trt), acetyl (Ac) and tosyl (Ts). More preferably, the protecting group(s) is/are selected from 9-fluorenylmethoxycarbonyl (Fmoc), tert-butyloxycarbonyl (Boc), benzoyloxycarbonyl (Cbz), benzyl (Bn) and trityl (Trt), even more preferably 9-fluorenylmethoxycarbonyl (Fmoc) and tert-butyloxycarbonyl (Boc). A particularly preferred protecting group is 9-fluorenylmethoxycarbonyl (Fmoc).

Suitable solid phases are, for example, conventional solid phases known to the skilled person. The solid phase is preferably a resin. The solid phase is preferably selected from the group consisting of divinylbenzyl (DVB)-linked polystyrene resins and polyethylene glycol (PEG)/polystyrene-based blended resins, the polyethylene glycol (PEG)/polystyrene-based blended resins are particularly preferred. The acid-labile linking component (linker) between solid phase and amino acid derivative of formula (VII)/linear peptide/thiazolidine or oxazolidine building block is preferably selected from the group consisting of trityl-based linkers (TRT), Rink amide linkers (RAM), phenylhydroxybenzyl-based linkers (PHB), and hydroxymethylphenoxyacetate-based linkers, more preferably from the group consisting of Rink-Amide linkers (RAM), phenylhydroxybenzyl-based linkers (PHB), and hydroxymethylphenoxyacetate-based linkers, even more preferably from the group consisting of phenylhydroxybenzyl-based linkers (PHB), and hydroxymethylphenoxyacetate-based linkers. Hydroxymethylphenoxyacetate-based linkers are particularly preferred.

In a preferred embodiment, in step (i) there is provided a linear peptide consisting of two to five, more preferably three to five, even more preferably four to five, in particularly prefered five, amino acid derivatives of formula (VII), wherein the terminal amino group is protected by at least one (preferably two) protecting group(s).

In step (ii) of the method according to the invention for the solid-phase peptide synthesis of a cyclic compound of formula (I) according to the invention, starting from the amino acid derivative of formula (VII), the peptide, or the thiazolidine or oxazolidine building block of step (i), one or more consecutive coupling reactions are carried out, in each case adding one or more amino acid derivatives of formula (VII)

of one or more linear peptides comprising/consisting of from two to five amino acid derivatives of formula (VII) (but no other amino acid derivatives), or a thiazolidine or oxazolidine building block, as already described in detail with respect to the second aspect of the present invention, wherein the terminal amino group is protected by at least one protecting group (N-terminal protecting group, wherein preferably exactly one H in the terminal amino group is replaced by a protecting group but the second H is not), the stepwise solid phase synthesis of a linear, solid phase-bound, compound comprising five amino acid derivatives of formula (VII), wherein i is 1 to 5, and a thiazolidine or oxazolidine building block as already described in detail with respect to the second aspect of the present invention is carried out.

That is, as many coupling reactions (coupling steps) are carried out—in the case of more than one coupling reaction using the product of the previous coupling reaction—until the product is a linear compound, which is bound to the solid phase, comprising five amino acid derivatives of formula (VII), where i is equal to 1 to 5, and a thiazolidine or oxazolidine building block. With respect to the substituents (X, $Y_1$ to $Y_5$, PG, etc.), the same applies as described in step (i).

It goes without saying that the relative arrangement of the amino acid derivatives of formula (VII) and the thiazolidine or oxazolidine building block with respect to one another in the linear compound bound to the solid phase is chosen so that the substituents X, $Y_1$ to $Y_5$ of the cyclic compound, are not identical amongst each other, and, after completion of the method according to the invention, are arranged in their sequence in such a way that it corresponds to the arrangement in the cyclic compound of formula (I) according to the invention (i.e. with the correct arrangement of the substituents X and $Y_1$-$Y_5$).

It also goes without saying that the individual amino acid derivatives of formula (VII), the linear peptide(s) and the thiazolidine or oxazolidine building block are to be selected in such a way that the alternating absolute stereochemical configuration specified for the cyclic compound of formula (I) according to the invention is complied with. This is also easily possible for the person skilled in the art due to his general knowledge.

The term "coupling reaction" or "coupling step" in this context is known to the skilled person. A coupling reaction preferably comprises two partial steps, 1) the removal of at least one N-terminal protecting group of the amino acid derivative of formula (VII), linear peptide, or thiazolidine or oxazolidine building block bound to the solid phase ("deprotection"), and 2) the actual coupling reaction with an amino acid derivative of formula (VII), a linear peptide, or thiazolidine or oxazolidine building block which is itself also N-terminally protected by at least one protecting group but is not bound to the solid phase ("condensation").

The removal of the N-terminal protecting group ("deprotection") and the coupling reaction can thereby be carried out in a manner known to the skilled person. Preferably, the deprotection is carried out using known deprotection conditions, for example for an Fmoc protecting group preferably using DBU, morpholine and/or piperidine in DMF, more preferably using DBU, morpholine and piperidine in DMF.

The amide bond-forming coupling reaction is preferably carried out at 15 to 25° C., preferably over a period of 30 to 45 min. The coupling reaction is preferably carried out in one or more polar aprotic solvents such as dimethysulfoxide (DMSO), acentonitrile (ACN), dichloromethane (DCM), N-methylpyrrolidone (NMP), or dimethylformamide (DMF), more preferably N-methylpyrrolidone (NMP) or dimethylformamide (DMF), even more preferably DMF, using one or more coupling reagents.

Preferred coupling reagents include carbodiimide-based coupling reagents (EDC, DIC), uronium-based coupling reagents (HATU, HBTU, TBTU), phosphonium-based coupling reagents (BOP, PyBOP, PyBrOP), a combination of uronium- and phosphonium-based coupling reagents (HATU/PyBOP) and DIPEA (N-ethyl-N-(propan-2-yl)propan-2-amine), and NMM (4-methylmorpholine), more preferably uronium-based coupling reagents (HATU, HBTU, TBTU), phosphonium-based coupling reagents (BOP, PyBOP, PyBrOP), a combination of uronium- and phosphonium-based coupling reagents (HATU/PyBOP) and DIPEA, and NMM, more preferably phosphonium-based coupling reagents (BOP, PyBOP, PyBrOP), a combination of uronium- and phosphonium-based coupling reagents (HATU/PyBOP) and DIPEA, and NMM, even more preferably a combination of uronium- and phosphonium-based coupling reagents (HATU/PyBOP) and DIPEA, and NMM. NMM is particularly preferred. In a preferred embodiment, a coupling additive is used for the coupling reaction, wherein the coupling additive is preferably hydroxyiminocyanoacetic acid ethyl ester (Oxyma), or benzotriazole-1-ol (HOBt), more preferably benzotriazole-1-ol (HOBt).

Thus, through a series of alternating deprotection and coupling reactions, a linear, solid phase-bound compound with specific amino acid derivative sequence, and specific alternating absolute stereochemical configuration of the C atoms directly linked to substituents X and $Y_1$ to $Y_5$ can be synthesized.

In a preferred embodiment, in step (ii), the amino acid derivatives of formula (VII), the peptide or the thiazolidine or oxazolidine building block to be added (i.e. not the amino acid derivative of formula (VII), the peptide, or the thiazolidine or oxazolidine building block of step (i), but the ones to be novelly added), are, or, respectively, is, not bound to a solid phase. In a further preferred embodiment, in each of the one or more coupling reactions in step (ii), the at least one protecting group is initially removed from the amino acid derivative of formula (VII), the peptide, or the thiazolidine or oxazolidine building block of step (i), respectively, and then the coupling is carried out with the amino acid derivative of formula (VII), the peptide, or the thiazolidine or oxazolidine building block, respectively, which is not bound to a solid phase.

In a preferred embodiment, in step (ii), an amino acid derivative of formula (VII) or a thiazolidine or oxazolidine building block (but not a peptide) is used for each of the coupling reactions, i.e. for each coupling step only one amino acid derivative of formula (VII) or one thiazolidine or oxazolidine building block (if no thiazolidine or oxazolidine building block has been used up to this point) is incorporated into the growing linear compound bound to the solid phase.

In a preferred embodiment of the method for solid-phase peptide synthesis of the cyclic compounds according to the invention, if a peptide is provided in step (i), said peptide has been prepared by solid-phase peptide synthesis by consecutive insertion of amino acid derivatives of formula (VII), each having alternating absolute stereochemical configuration of the C atom directly linked to the substituent $Y_{1-5}$.

In the linear compound of step (ii) which is bound to the solid phase, among the C atoms directly linked to a substituent $Y_{1-5}$ or X, those along the chain backbone of the linear compound directly following each other (i.e. those closest along the chain backbone), have an alternating absolute stereochemical configuration; i.e. the linear compound of step (b), which is bound to the solid phase, has, an alternating absolute stereochemical configuration with respect to the C atoms directly linked to a substituent $Y_{1-5}$ or X along the chain backbone of the linear compound.

This means that in the linear solid phase-bound compound of step (ii), each C atom that is directly linked to a substituent $Y_{1-5}$ or X (and which is not the first or last substituent along the chain backbone of the linear compound) has an opposite absolute stereochemical configuration with respect to the C atoms closest on either side of that C atom along the chain backbone of the linear compound that are also directly linked to a substituent $Y_{1-5}$ and X.

In an exemplary preferred embodiment of the method, in step (ii), initially a first coupling reaction is carried out. This involves removing the terminal amino group of the amino acid derivative, the peptide or the thiazolidine or oxazolidine building block of step (i) ("deprotecting"); and then in a second step, "coupling" to another, not bound to a solid phase, amino acid derivative of formula (VII), peptide comprising (preferably consisting of) two to five amino acid derivatives of formula (VII) and no other amino acid derivatives, or to a, not bound to a solid phase, thiazolidine or oxazolidine building block of formula (II) as described in detail with regard to the second aspect of the present invention (provided that no thiazolidine or oxazolidine building block of formula (II) was used in step (i)). In this method, the terminal amino group of the further amino acid derivative or peptide, or of the thiazolidine or oxazolidine building block of formula (II) is preferably protected by at least one, more preferably by exactly one, protecting group.

In this exemplary preferred embodiment, this first coupling reaction is repeated one, two, three or four times, using the respective solid phase-bound product of the previous coupling reaction; wherein stepwise further amino acid derivatives of formula (VII), peptides comprising exclusively amino acid derivatives of formula (VII), or, respectively, a thiazolidine or oxazolidine building block of formula (II) as described in detail with respect to the second aspect of the present invention, provided that no thiazolidine or oxazolidine building block of formula (II) has yet been used in the preceding steps, each containing in the terminal amino group at least (a PG which is) a protecting group, are inserted into the growing linear solid phase-bound compound; to finally obtain a linear solid phase-bound compound comprising five amino acid derivatives of formula (VII), wherein i is 1 to 5, and a thiazolidine or oxazolidine building block of formula (II).

It goes without saying that in each case the further amino acid derivative of formula (IV) which is not bound to a solid phase, the C-terminal amino acid derivative in the further peptide which is not bound to a solid phase, or, respectively, the thiazolidine or oxazolidine building block which is not bound to a solid phase, has, at the C atom which is directly linked to the substituent $Y_{1-5}$ or X, respectively, an absolute stereochemical configuration which is opposite to the absolute stereochemical configuration of the C atom which is directly linked to the substituent $Y_{1-5}$, or X, in the solid phase-bound amino acid derivative, in the N-terminal amino acid derivative of the solid phase-bound peptide, or, respectively, in the solid phase-bound thiazolidine or oxazolidine building block bound. Of course, this is also true for any further coupling reaction.

In step (iii) of the method according to the invention for solid phase peptide synthesis of a cyclic compound of formula (I) according to the invention, removing the protecting group from the linear solid phase-bound product of step (ii) ("deprotecting") and cleaving off from the solid phase to form a linear compound, which is not bound to the solid phase, is carried out. Preferably, said linear solid phase-bound product of step (ii) has only at the N-terminus one or two protecting groups (preferably a protecting group and an N—H bond), which is, respectively, are then removed in step (iii). Removing the protecting groups and cleaving off from the solid phase can be carried out, for example, with reaction conditions and reagents known in the prior art, for example simultaneously but also sequentially.

In a preferred embodiment of step (iii), deprotecting and cleaving off from the solid phase is carried out with 0.5 to 4% (v/v) DBU (1,8-diazabicyclo[5.4.0]undec-7-ene) and 5 to 15% (v/v) morpholine in DMF, and subsequently with a mixture of TFA (trifluoroacetic acid), triisopropylsilane (TIPS) and water, in a preferred ratio of 90-92.5:2.5-5:5 (v/v/v).

Finally, in step (iv) of the method according to the invention for the solid-phase peptide synthesis of a cyclic compound of formula (I) according to the invention, the macrocyclization of the linear compound of step (iii), which is not bound to the solid phase, is carried out, preferably by macrolactamization, whereby the cyclic compound of formula (I) according to the invention is obtained. The macrocyclization or preferably macrolactamization can be carried out, for example, using reaction conditions and reagents known from the prior art.

Surprisingly, it was found that via macrocyclization the formation of the novel cyclic compounds (without the usual pattern of [NH—CH(H or organic residues)-C═O-]$_n$) can be achieved, wherein each of said cyclic compounds contains a fully intact, for example, alkyl-aryl- or alkynyl-substituted thiazolidine or oxazolidine ring with different substitution patterns. The alkyl-, aryl-, or alkynyl-bearing (for example R=H and R'=methyl, ethyl, propyl, benzyl, propargyl; or R=CH3 and R'=methyl, ethyl, propyl, benzyl, propargyl) thiazolidine and oxazolidine rings thereby interrupt the usual peptide backbone pattern.

The macrocyclization of the linear compound of step (iii), which is not bound to the solid phase, is preferably carried out at 15 to 25° C., for example with EDC/NMM/HOBt, HATU/DIPEA/HOBt, or HATU/DIPEA/HOAt, preferably HATU/DIPEA/HOBt, or HATU/DIPEA/HOAt, more preferably HATU/DIPEA/HOAt, in a polar-aprotic solvent (see above). The cyclization is preferably carried out in DMF, acetonitrile and/or NMP, more preferably in DMF, as polar-aprotic solvent. The cyclization is preferably carried out for at least 15 hours, more preferably 15 to 30 hours, even more preferably 24 hours. The reaction mixture is preferably diluted with water in a ratio of ≥1:1 (v/v), more preferably ≥2:1 (v/v), more preferably by 3:1 (v/v) and extracted with a, preferably binary, mixture of a halogenated, e.g. chlorinated, solvent (for example DCM or chloroform) or a solvent of the carboxylic ester group, and an alcohol (e.g. n-butanol), preferably in a ratio ≥3:1 (v/v), more preferably ≥5:1 (v/v), more preferably 6:1 (v/v), or preferably with higher alcohols (e.g. n-butanol) and/or ethers (preferably cyclic ether solvents such as THE and 2-Me-THF), i.e. alone or as a solvent mixture.

the C atom directly linked to residue $Y_1$ in the N-terminal amino acid derivative of the pentapeptide of step (i).

(iii) Removing the protecting groups (deprotecting) the side chains of compound (VIII) of step (ii) and cleaving compound (VIII) off from the solid phase to form a linear compound of formula (IX):

(IX)

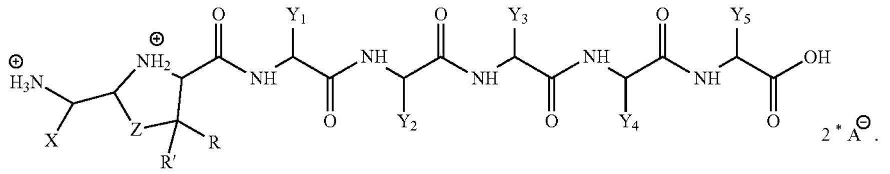

With respect to the substituents and the other parameters of the cyclic compound of formula (I) and synthesis precursors according to the invention prepared by the solid-phase peptide synthesis method according to the invention, what is described in the first to third aspects of the present invention applies accordingly.

An exemplary preferred embodiment of the method for solid-phase peptide synthesis of the cyclic compound of formula (I) according to the invention comprises the following steps (i) to (iv):

(i) Providing a protected pentapeptide of formula (VII):

(VII)

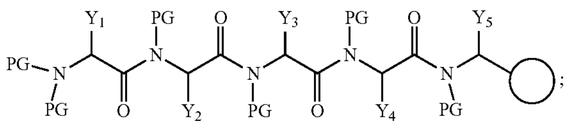

which is bound to a solid phase via its C-terminus; wherein the pentapeptide was prepared by solid-phase peptide synthesis, preferably by consecutive insertion of amino acid derivatives each having an alternating absolute stereochemical configuration of the α-carbon (Ca).

(ii) Carrying out a coupling reaction, by removing the protecting group from the N-terminus of the protected pentapeptide of step (i) and coupling the resulting deprotected pentapeptide to a thiazolidine or oxazolidine building block of formula (II) as already described in the second aspect of the present invention, and forming a compound of formula (VIII):

(VIII)

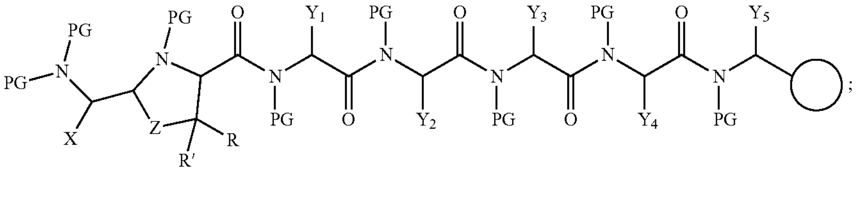

wherein the absolute stereochemical configuration of the C atom directly linked to substituent X in the thiazolidine or oxazolidine building block is opposite to the absolute stereochemical configuration of (iv) Macrocyclization of the linear compound (IX) of step (iii), preferably by macrolactamization, to obtain the cyclic compound of formula (I) according to the invention (the filled dark gray circle represents the solid phase, and A is an anion).

In a further preferred embodiment of the present method for solid-phase peptide synthesis of the cyclic compound of formula (I) according to the invention, in each case only the N-terminal amino groups are protected by protecting groups, preferably only by one protecting group molecule (secondary amino group).

According to a preferred embodiment of the present method for solid-phase peptide synthesis of the cyclic compounds of formula (I) according to the invention, the thiazolidine or oxazolidine building block used in step (i) or step (ii) is prepared according to the method for synthesis of a thiazolidine or oxazolidine building block of formula (II) according to the invention, as already described with respect to the third aspect of the present invention.

Cosmetic Preparation Containing Cyclic Compounds of Formula (I)

In a fifth aspect, the present invention is directed to a cosmetic preparation containing (a) one or more cyclic compounds of formula (I) according to the invention; and (b) one or more cosmetically acceptable carriers.

The one or more cyclic compounds of formula (I) are those as defined in the above sections. Advantageously, these cyclic compounds of formula (I) according to the invention can be prepared by the novel method according to the invention for solid-phase peptide synthesis of a cyclic compound of formula (I). In the cosmetic preparation according to the invention, one or more different cyclic compounds of formula (I) may be present. In a preferred embodiment, the cosmetic preparation according to the invention contains one cyclic compound of formula (I)

according to the invention, i.e. only one specific molecular embodiment of formula (I) according to the invention. In an alternatively preferred embodiment, the cosmetic preparation according to the invention contains at least two different cyclic compounds of formula (I) according to the invention.

In a preferred embodiment of the cosmetic preparation, the cyclic compound of formula (I) is compound I.3. Thus, in a particularly preferred embodiment, the present invention is directed to a cosmetic preparation comprising (a) a cyclic compound characterized by the following formula:

I.3

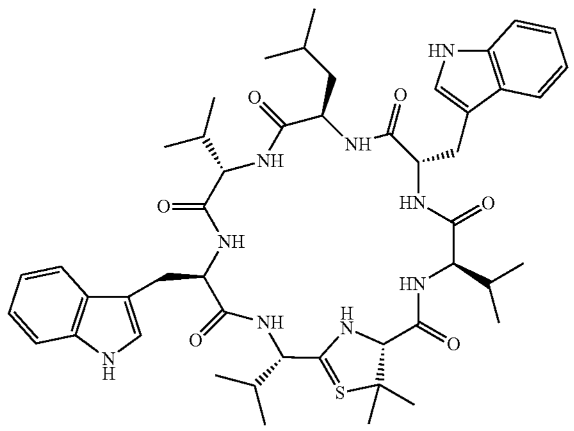

and (b) one or more cosmetically acceptable carriers.

The one or more cosmetically acceptable carriers are not further limited. Suitable cosmetically acceptable carriers are known to the skilled person. Suitable cosmetically acceptable carriers include, for example, cosmetic excipients, diluents, carriers, binders, anti-adhesive agents, dispersants and other cosmetic additives, such as preservatives, bactericides, deodorizing substances, antiperspirants, vitamins, anti-foaming agents, colorants, pigments, thickeners, emollient substances, moisturizing and/or humectant substances, fats, oils, waxes, water, alcohols, polyols, polymers, foam stabilizers, electrolytes, UV radiation absorbing substances, organic solvents or silicone derivatives. The cosmetic preparation may optionally also contain other cosmetic active ingredients which can be advantageously combined with the cyclic compounds of formula (I) according to the invention.

In a preferred embodiment of the cosmetic preparation, for example for topical use, the cyclic compounds of formula (I) contained therein preferably exhibit an antimicrobial, in particular an antiviral, antibacterial (bactericidal, in particular a non-selective antimicrobial activity preferably specifically against gram-positive bacteria, but preferably not or only minimally against gram-negative bacteria) and/or antifungal (fungicidal), more preferably an antiviral and/or non-selective antimicrobial activity. Furthermore, the cyclic compounds of formula (I) according to the invention contained in the cosmetic preparation, preferably exhibit a supportive effect on the innate immune response, e.g. of the skin, preferably against non-commensal, microorganisms, for example non-commensal bacteria, for example in topic use on the skin.

The cosmetic preparations of the present invention, in particular those containing compound I.3, are also particularly suitable for use in atopic skin, a condition in which the barrier function of the skin is lost, so that allergenic substances can penetrate the skin and moisture is lost at the same time. Unless this loss of function is not counteracted, an atopic skin condition can develop into atopic dermatitis. In a further aspect, the invention thus also relates to one or more cyclic compounds of formula (I), in particular compound I.3, or cosmetic compositions containing these compounds, for use in a method of treating atopic dermatitis.

In this context, the cosmetic preparation is preferably in the form of a dermatological preparation for topical application. The cyclic compounds of formula (I) according to the invention used in this context preferably have an antimicrobial, in particular an antiviral, antibacterial (bactericidal, in particular a non-selective antimicrobial activity preferably against Gram-positive bacteria, but preferably not against Gram-negative bacteria) and/or antifungal (fungicidal), more preferably an antiviral and/or a non-selective antibacterial, activity.

Furthermore, the cyclic compounds of formula (I) used in this method preferably have a supporting effect on the innate immune response, e.g. of the skin, preferably against non-commensal microorganisms, e.g. non-commensal bacteria.

EXAMPLES

The following examples illustrate the invention.

Abbreviations Used:

$Ac_2O$, acetic anhydride; CDI, 1,1'-carbonyldiimidazole; DBU, 2,3,4,6,7,8,9,10-octahydropyrimido[1,2-a]azepine; DIPEA, N-ethyl-N-(propan-2-yl)propan-2-amine; DMP, dess-martin-periodinan; $Et_2O$, diethyl ether; HATU, 1-[bis(dimethylamino)methylene]-1H-1,2,3-triazolo[4,5-b]pyridinium-3-oxide hexafluorophosphate; HOAt, 3-hydroxytriazolo[4,5-b]pyridine; HOBt, benzotriazol-1-ol; IPA, isopropyl alcohol; MHMPA, 3-methoxy-4-(hydroxymethyl)phenoxyacetic acid; MIC, minimum inhibitory concentration; n-BuOH, n-butanol; NMM, 4-methylmorpholine; Pra, propargylglycine; PyBOP, (benzotriazol-1-yloxy)tripyrrolidino-phosphonium hexafluorophosphate; Pyr, pyridine; SPPS, solid-phase peptide synthesis; TFA, trifluoroacetic acid; Thz, thiazolidine; TIPS, triisopropylsilane.

Example 1: Synthesis of Novel Thiazolidine or Oxazolidine Building Blocks

A) Synthesis Thiazolidine Building Block

In brief, the synthesis was implemented in three steps. First, the carboxylic acid in Fmoc-protected L-valine was activated by carbonyldiimidazole (CDI) and subsequently reduced with sodium borohydrate ($NaBH_4$) to the corresponding alcohol Fmoc-L-valinol. Fmoc-L-valinol was subsequently reoxidized by des-martin-parodinane (DMP) to the corresponding aldehyde.

Finally, condensation with

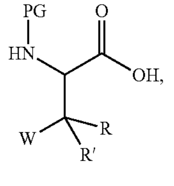

where W=SH, gave the desired thiazolidine building block, which advantageously precipitated during the reaction and was filtered off, ready for use in convenient Fmoc-SPPS protocols by solubilization in DMF.

In detail, N-alpha-(9-fluorenylmethyloxycarbonyl)-L-valine (5.00 g, 14.75 mmol) was dissolved in THE (50 mL) and 1,1'-carbonyldiimidazole (3.1 g, 19.1 mmol, 1.3 equiv.) was added in one portion. The solution was stirred at room temperature (RT) for 15 min and cooled to 0° C. for 10 min. To this solution, $NaBH_4$ (945 mg, 25.0 mmol, 1.7 equiv.) in water (15 mL) was rapidly and uniformly injected and stirred at 0° C. for 25 min. The reaction was quenched by adding 1 N HCl (10 mL) and 50 mL of water. The reaction mixture was extracted with EtOAc (3×60 mL). The combined organic extracts were washed with saturated $NaHCO_3$ (3×100 mL), and brine (3×100 mL) and dried over $Na_2SO_4$. The solution was filtered through a thin Celite pad, the solvent was evaporated and vacuum dried to give the corresponding alcohol N-alpha-(9-fluorenylmethyloxycarbonyl)-L-valinol as a white solid.

N-alpha-(9-fluorenylmethyloxycarbonyl)-L-valinol was dissolved in DCM (100 mL) and cooled to 0° C. in an ice-water bath. Dess-martin-periodinan (DMP, 9.3 g, 22 mmol, 1.5 equiv.) was added in portions over 10 min at 0° C. After DMP addition was complete, the ice water bath was removed and the reaction mixture was warmed to room temperature. During the first hour, water (250 μL, 1.1 equiv.) was added in four portions. The reaction mixture was stirred overnight at room temperature. The reaction mixture was quenched by adding $Na_2S_2O_3$ (4.5 g) and $NaHCO_3$ (1.5 g) to water (300 mL) and stirred for 30 minutes. The resulting suspension was centrifuged and the remaining solids were filtered off. The phases were separated and the organic phase was washed with 1N $Na_2S_2O_3$ (5×75 mL), $KHSO_4$ 10% (v/v, 3×75 mL), saturated $NaHCO_3$ (3×75 mL), saturated NaCl (3×75 mL), dried over $Na_2SO_4$ dried and evaporated to dryness to give the corresponding aldehyde N-alpha-(9-fluorenylmethyloxycarbonyl)-L-valinal as a beige-colored solid.

The N-alpha-(9-fluorenylmethyloxycarbonyl)-L-valinal and 3 equiv. of the compound of formula

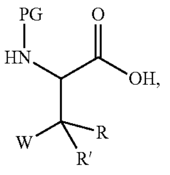

wherein W=SH, were suspended in MeOH/$H_2O$ (2:1, 100 mL+50 mL). The resulting suspension was heated to 65° C. and stirred for 20 hours. A white precipitate formed during the reaction. The methanol was removed in vacuo, water (100 mL) was added, and the suspension was stored overnight at 4° C. The white precipitate was filtered and washed with an excess of water (1 L). Residual water in the wet solid was evaporated and vacuum dried for 48 hours. The resulting solid was slurried in toluene/pentane (3:1; 45 mL+15 mL), $CHCl_3$/THF (1:1; 30 mL+30 mL), IPA/acetone/pentane (1:1:1; 20 mL+20 mL+20 mL) and dried under vacuum to give the thiazolidine building block as a white solid.

Example 2: Solid-Phase Peptide Synthesis (SPPS) of Novel Cyclic Compounds

A preactivated solution of protected amino acid derivative (6 equiv.), HATU (6 equiv.), HOBt (6 equiv.), and N-methylmorpholine (NMM, 8 equiv.) in DMF was added to the resin and reacted for 30-45 min. The procedure was repeated using PyBOP instead of HATU as coupling reagent. Washing after coupling was performed with DMF (3×2 mL), DCM (3×2 mL), and DMF (3×2 mL). Note: The first D-Val→L-Val coupling was carried out in DMF/DCM (1:1.2 mL) due to the better resin swelling properties of DCM and HOAt instead of HOBt to achieve higher yields. Capping: pyridine/$Ac_2O$/DMF (1:3:6 v/v/v, 2 mL) was added to the resin and reacted for 30 min.

Deprotecting: Fmoc-D-Val AC TG resin was swollen in DMF (2 mL) for 30 min. The Fmoc group was removed by treatment with a solution of 2% DBU/10% morpholine (v/v) in DMF (2 mL) for 3 min and another 12 min. The resin was washed with DMF (3×2 mL), DCM (3×2 mL), and DMF (3×2 mL).

Coupling reactions: For the first consecutive Val→Val coupling, a solution of Fmoc-L-Val-OH (6 equiv.), HATU (6 equiv.), HOAt (6 equiv.), and NMM (8 equiv.) in DMF/DCM (2 mL) was added to the resin and stirred for 30-45 min. Double coupling was performed with PyBOP (6 equiv.) for 30-45 min. The resin was washed with DMF (3×2 mL), DCM (3×2 mL), DMF (3×2 mL), and unreacted resin-bound amino groups were capped by treatment with pyridine/Ac2O/DMF (1:3:6 v/v/v, 2 mL) for 30 min. The resin was washed with DMF (3×2 mL), DCM (3×2 mL), IPA (3×2 mL), and DMF (3×2 mL). The resin-bound residue was subjected to iterative peptide assembly (Fmoc-SPPS) using 2% DBU/10% morpholine (v/v) in DMF (2 mL, 3 and 12 min) for Fmoc deprotection and Fmoc-D/L-AA-OH (6 equiv.), HATU+PyBOP (6 equiv.), HOBt (6 equiv.), and NMM (8 equiv.) in DMF (2 mL) for 2×30-45 min to double-couple each amino acid. Amino acid coupling equivalence: Fmoc-D-Leu-OH, Fmoc-L-Trp(Boc)-OH, Fmoc-D-Val-OH, and finally a thiazolidine building block.

Cleavage: After complete synthesis of the linear compound on the solid phase, the last Fmoc protecting group was removed and the resin was washed with DMF (3×2 mL), DCM (3×2 mL), toluene (3×2 mL), IPA (3×2 mL), $Et_2O$ (3×2 mL) and dried for 3 h under reduced pressure. The peptide was cleaved by treatment with TFA/TIPS/$H_2O$ (90:5:5 v/v/v, 2 mL) for 3×1 h and a washing step with TFA (2 mL) for 10 min. The solvent was removed under reduced pressure and the linear peptides were lyophilized with tBuOH/$H_2O$ (1:1 v/v, 10 mL). The lyophilized linear compound was then used for macrolactamization without further purification.

Macrolactamization: To a stirred solution of the linear compound in DMF (10 mL) HOAt (21.0 mg, 0.156 mmol, 6 equiv.) and DIPEA (34 μL, 0.2 mmol, 8 equiv.) was added at room temperature. HATU (38 mg, 0.1 mmol, 4 equiv.) was dissolved in DMF (3 mL) and added over 1 h to the solution containing the linear peptide. The final concentration of the linear peptide was 2 mM. The yellow solution was stirred for 24 h at room temperature. To the reaction mixture, the binary solvent mixtures of n-butanol (5 mL) and chloroform (20 mL) or preferably n-butanol (5 mL) and other alcohols or ethers were added, and then water (30 mL) and saturated NaCl (5 mL) were added. After phase separation, the aqueous phase was extracted with chloroform (2×20 mL) or preferably higher alcohols or ethers. The combined organic extracts were washed with $KHSO_4$ (10% v/v, 4×35 mL), saturated $NaHCO_3$ (3×35 mL), ACN/$H_2O$ (10% v/v, 2×35 mL), and saturated NaCl (3×35 mL). The solvent was removed under reduced pressure and lyophilized with tert-butanol/water (1:1 v/v, 10 mL).

Example 3: Bioassay, MS and NMR with Cyclic Compounds I.1, I.2, I.3 and I.4

A) Bioassay with Cyclic Compounds I.1, I.2, I.3 and I.4

The bactericidal activity of cyclic compounds I.1 (ISW 1-0), I.2 (ISW 1-1), I.3 (ISW 1-2), and I.4 (ISW 1-4) (see FIG. 1 A) were determined using a serial dilution method as previously described, for example, in Schilling et al. *Angew. Chem. Int. Ed.* 2019, 58 (27), 9234-9238 described. For this purpose, a twofold dilution series was prepared in microtiter plates (stock solution: 10 mg/mL or 10 mM dissolved in DMSO, respectively) with different concentrations of cyclic compounds I.1, I.2, I.3, and I.4 in Müller-Hinton broth (NMB; 0.2% meat extract, 1.75% acid hydrolysate of casein, 0.15% starch; Carl Roth GmbH+Co. KG). In each case, the dilution series was started with a concentration of 100 μg/mL and 100 μM, respectively, and continued with two-fold dilutions (i.e., 1:1 in each case) through a serial dilution to the final concentration of 0.2 μg/mL and 0.2 μM, respectively.

Microtiter plates were inoculated with *S. aureus* USA300 LAC from an overnight culture to a final density of $1 \times 10^6$ colony forming units (cfu) per mL (100 μL culture, OD600Start=0.00125). The inoculated microtiter plates (including the cyclic compounds at various concentrations or DMSO as a negative control) were incubated at 37° C. for 22 h with constant shaking at 160 rpm.

The OD600 value of each well was measured using a microplate reader and the minimum inhibitory concentration (MIC) was determined for the cyclic compounds. The values were already adjusted from the blank samples. The results are shown in FIG. 2 A. Color coding: minimal inhibitory concentration (MIC); red: growth; white: no growth. For example, the MIC value can be defined as the concentration of an antimicrobial compound to be tested at which the optical density (OD600) is less than 75% of the control without the antimicrobial compound to be tested (MIC75). Alternatively, the MIC value can be defined, for example, as the lowest concentration of the antimicrobial compound to be tested at which the OD600 is <0.1 (a.u.).

Performing the bioassay with the cyclic compounds using *Streptococcus pneumoniae* ATCC49619 and *Staphylococcus epidermidis*, as examples of other Gram-positive bacteria, leads to comparable results in terms of antibacterial activity as for *S. aureus* USA300 LAC. Gram-negative bacteria such as *Pseudomonas aeruginosa* PAO1 and *Escherichia coli* DH5a, on the other hand, show no or only minimal (e.g. an MIC up to more than 30-fold greater compared to the Gram-positive bacteria) antibacterial activity.

B) Coupled HPLC-Mass Spectrometry (MS) Analysis of Cyclic Compounds

Cyclic compounds I.1, I.2, I.3, and I.4 were dissolved in methanol (MeOH, HPLC-MS grade, 0.1 mgmL−1), and the analyte was subjected to high-performance liquid chromatography (HPLC) using the Dionex Ultimate 3000 HPLC system (Thermo Fisher Scientific) with a diode array detector for the UV spectrum.

Stationary phase, column: Nucleoshell EC RP-C18 (2.7 μm, 3 Å, 150×3 mm, Macherey-Nagel GmbH & Co. KG). Mobile phase, solvent: gradient with 0 min (90% solvent A and 10% solvent B) up to 20 min (100% solvent B) with a flow rate of 0.3 mL/min. Solvent A=MeOH with 0.06% formic acid; solvent B=$H_2O$ with 0.1% formic acid.

Figure 3:
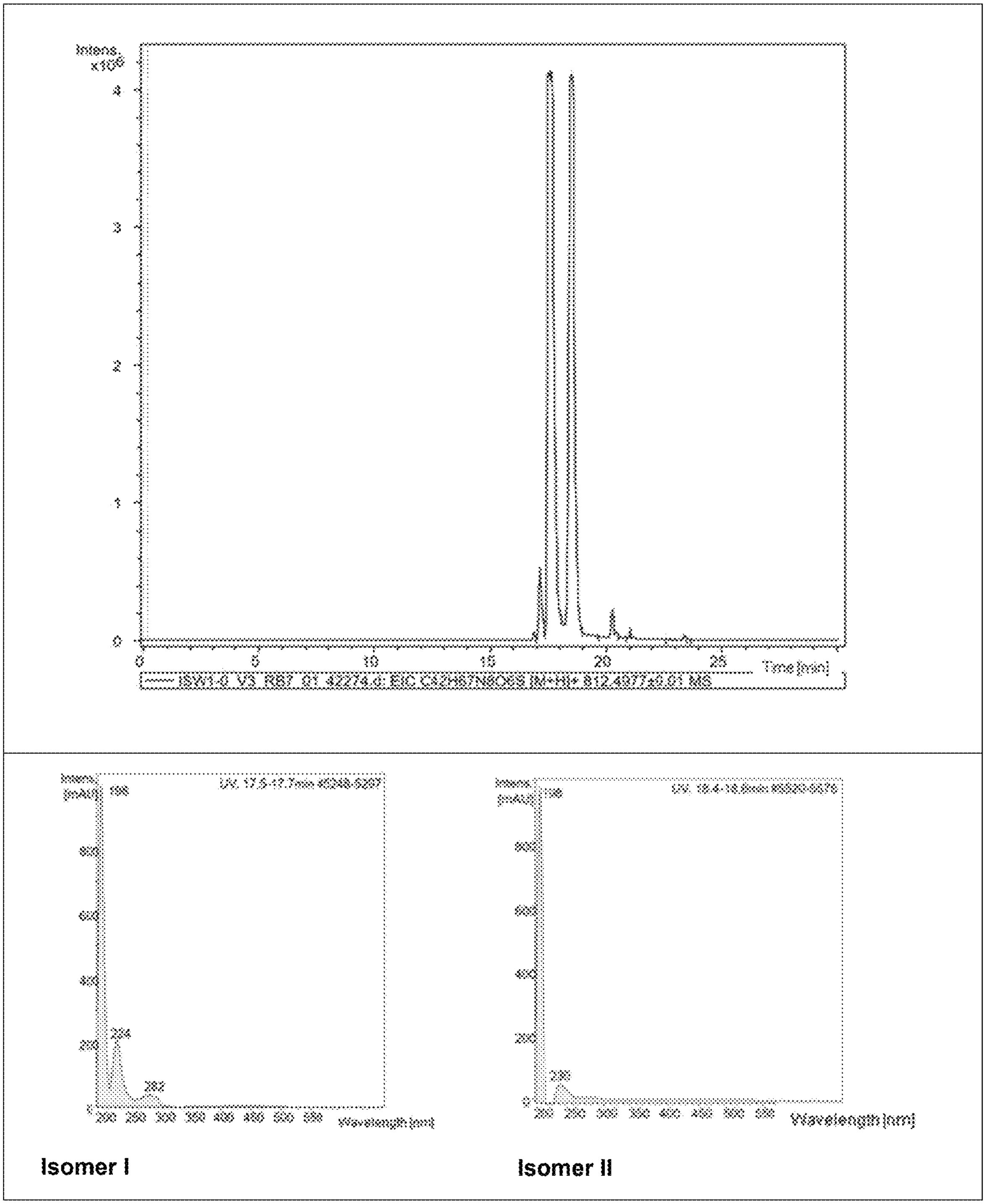
FIG. 3: Spectra of HPLC mass spectrometry (HPLC-MS) analysis of the cyclic compounds: (A) & (B) MS spectra of compound I.1, (C) & (D) MS spectra of compound I.2, (E) & (F) MS spectra of compound I.3, and (G) & (H) MS spectra of compound I.4; (I) & (J) MS spectra of compound I.19; (K) & (L) MS spectra of compound I.20; (M) & (N) MS spectra of compound 0.21; (O) & (P) MS spectra of compound I.22; (Q) & (R) MS spectra of compound I.23; (S) & (T) MS spectra of compound I.24; recorded with an ESI-QTOF mass spectrometer (MaXis 4G, Bruker Daltonics GmbH).
Figure 3:
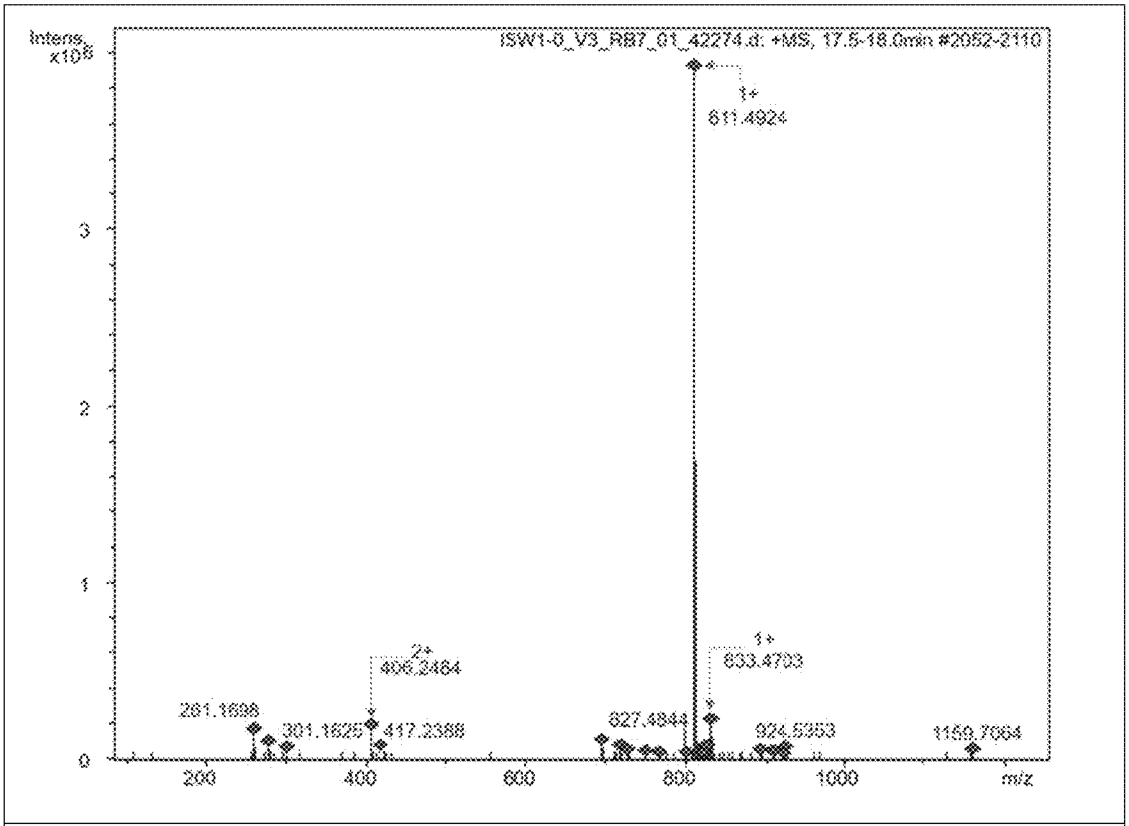
Figure 3:
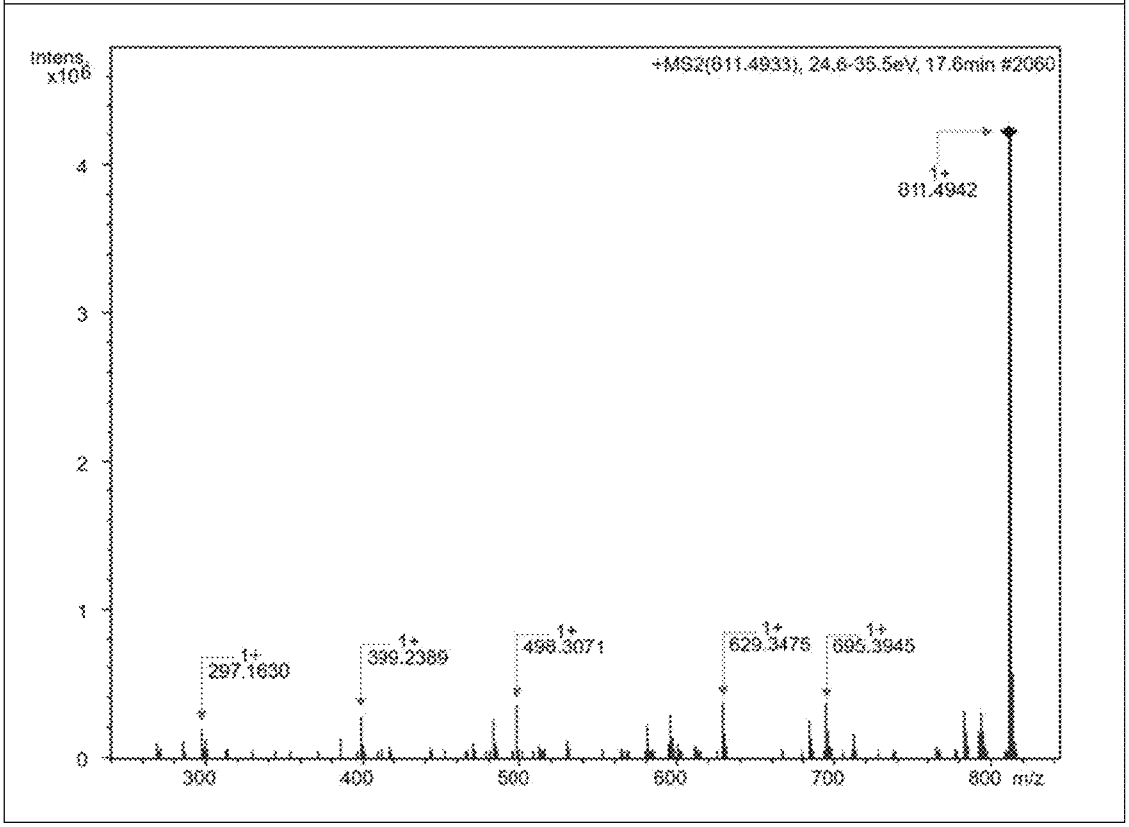
Figure 3:
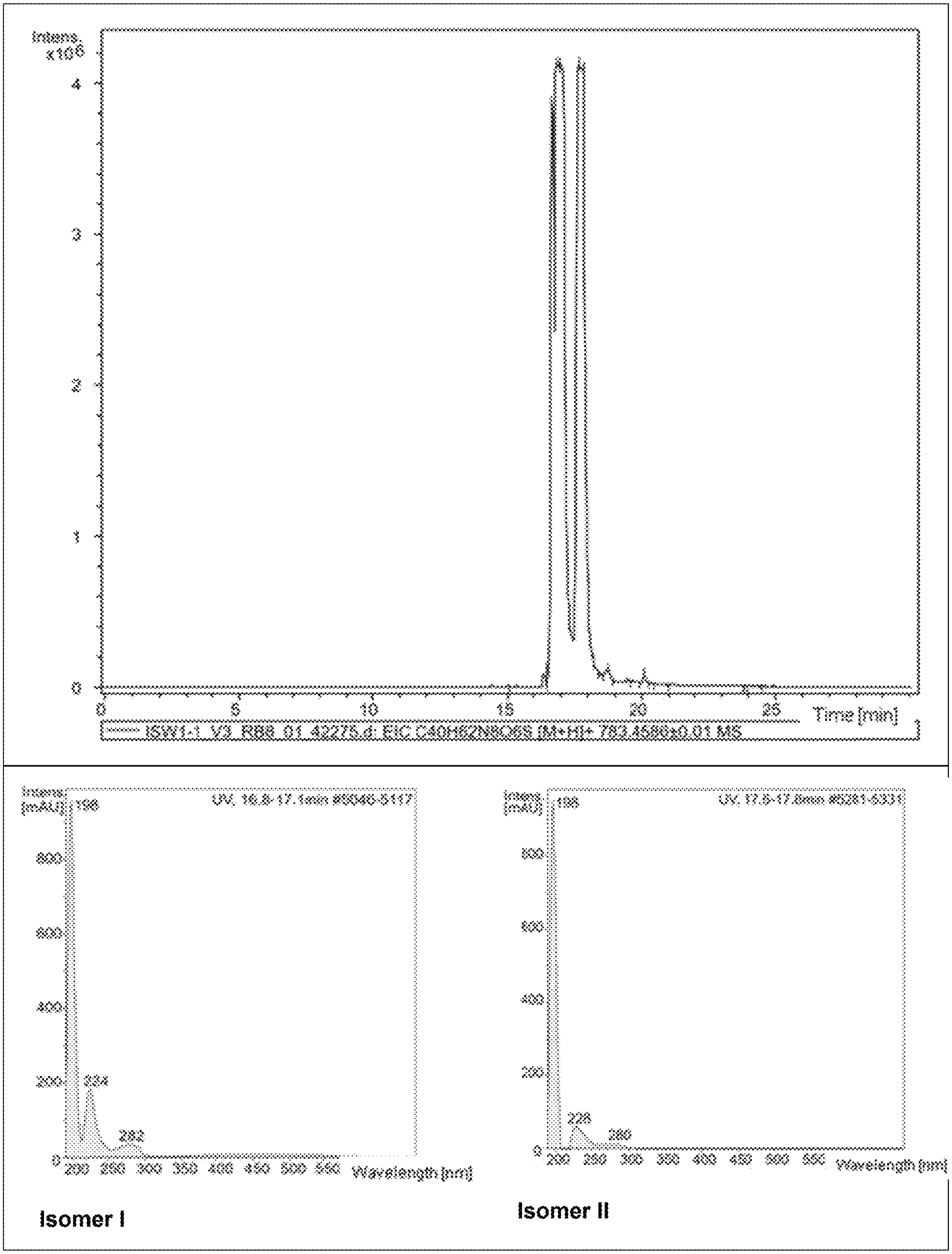
Figure 3:
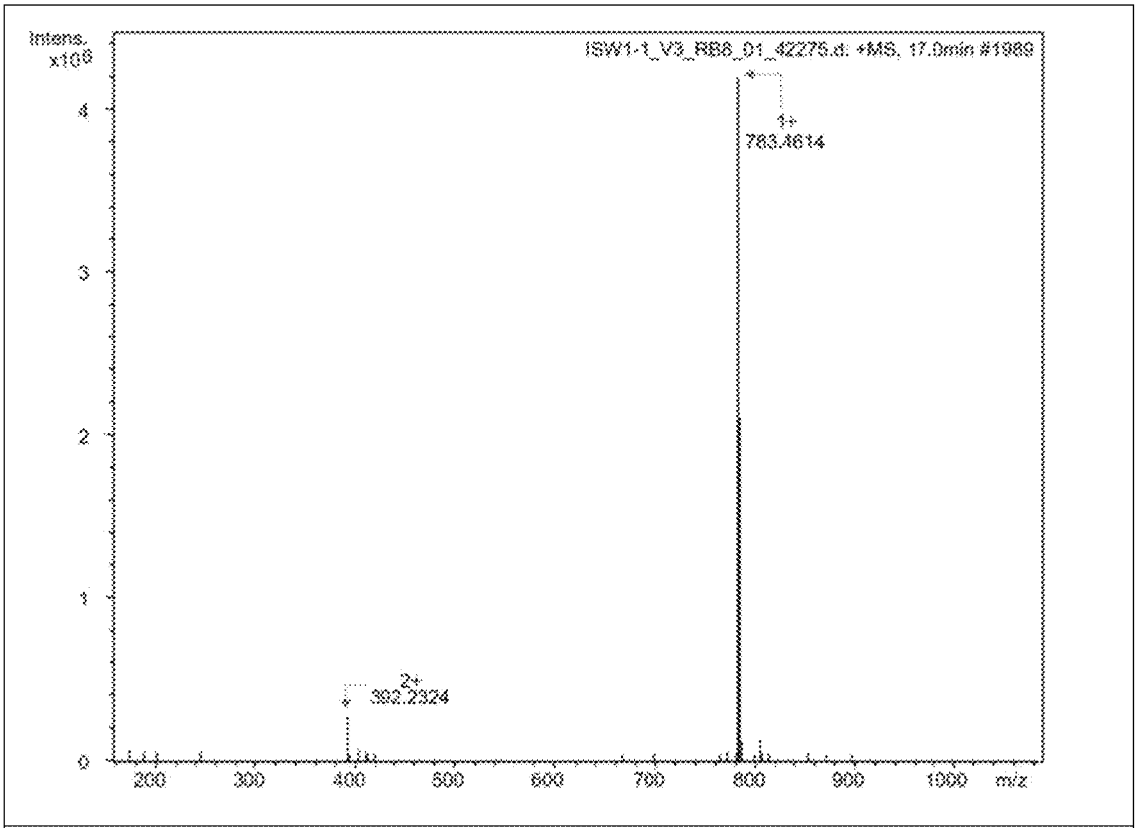
Figure 3:
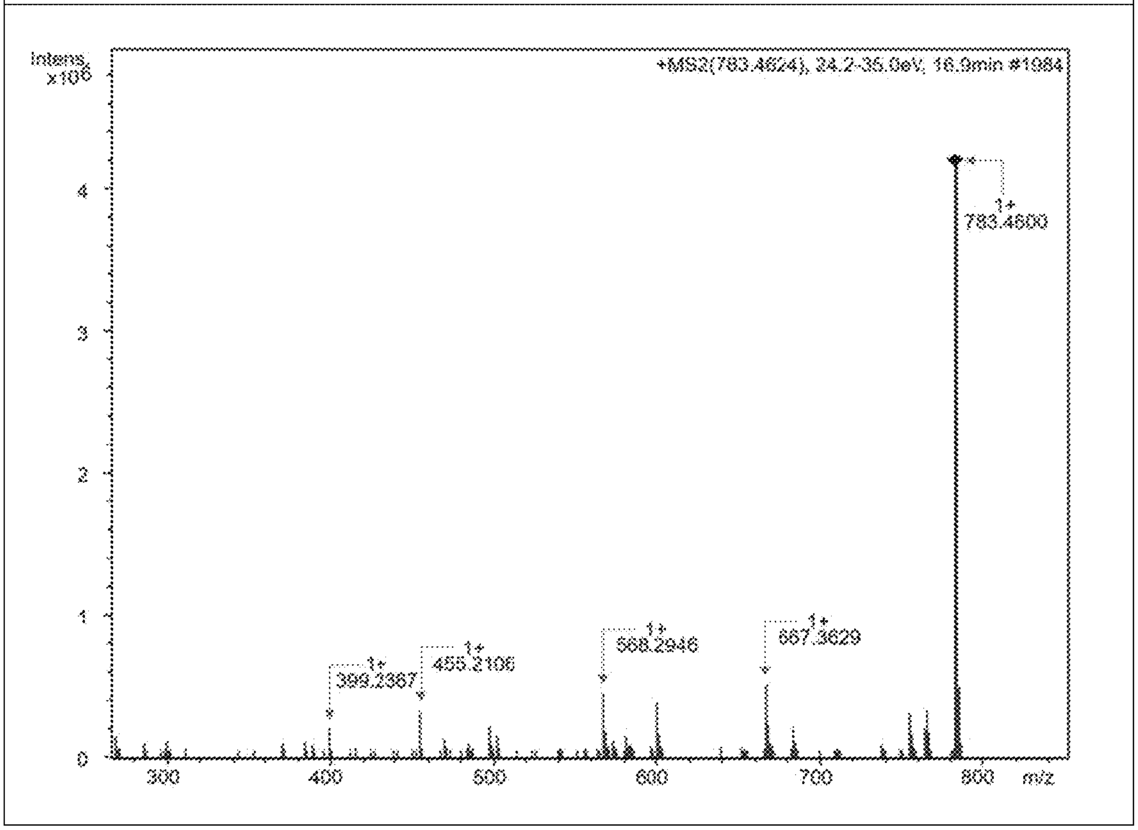
Figure 3:
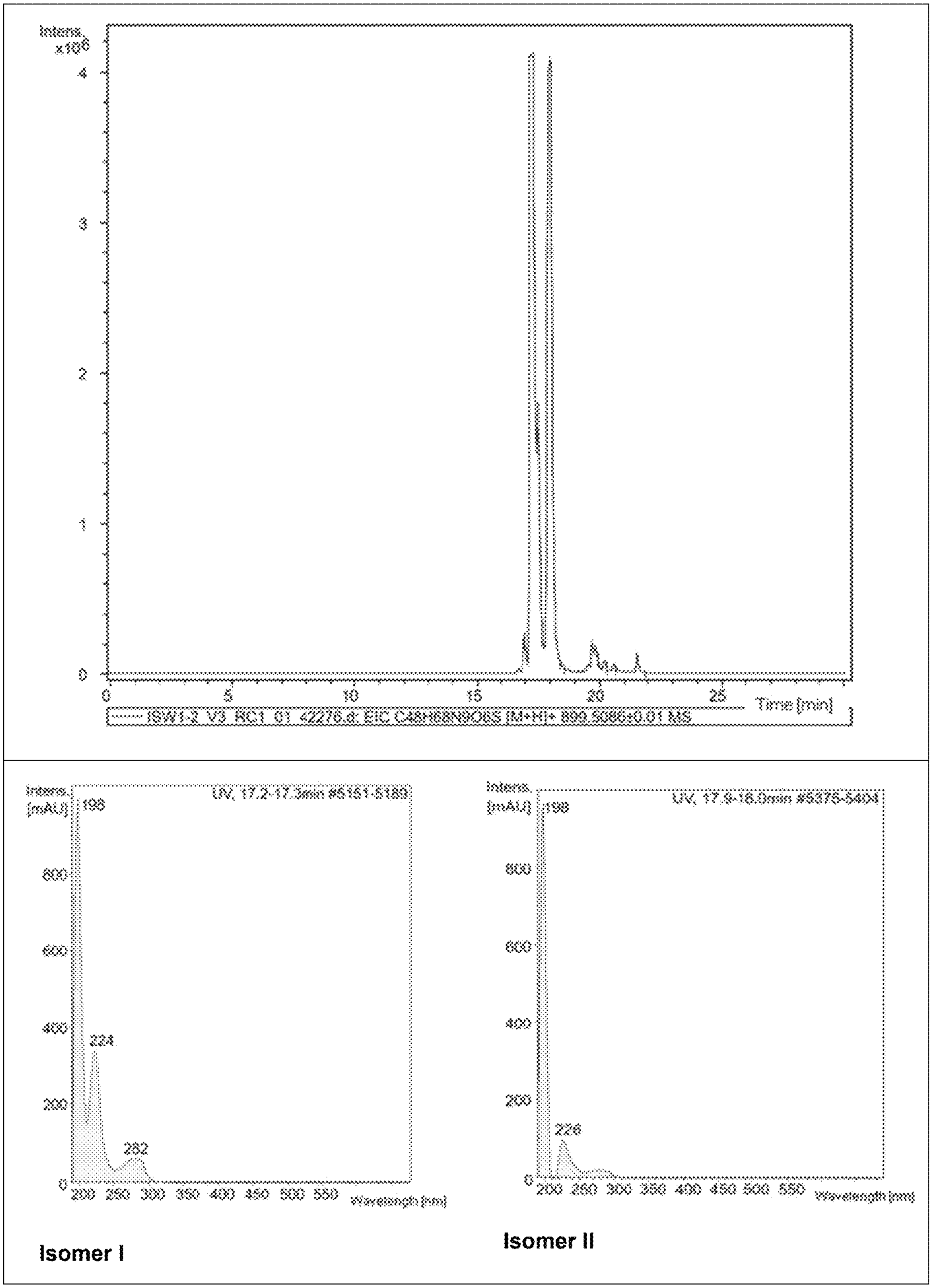
Figure 3:
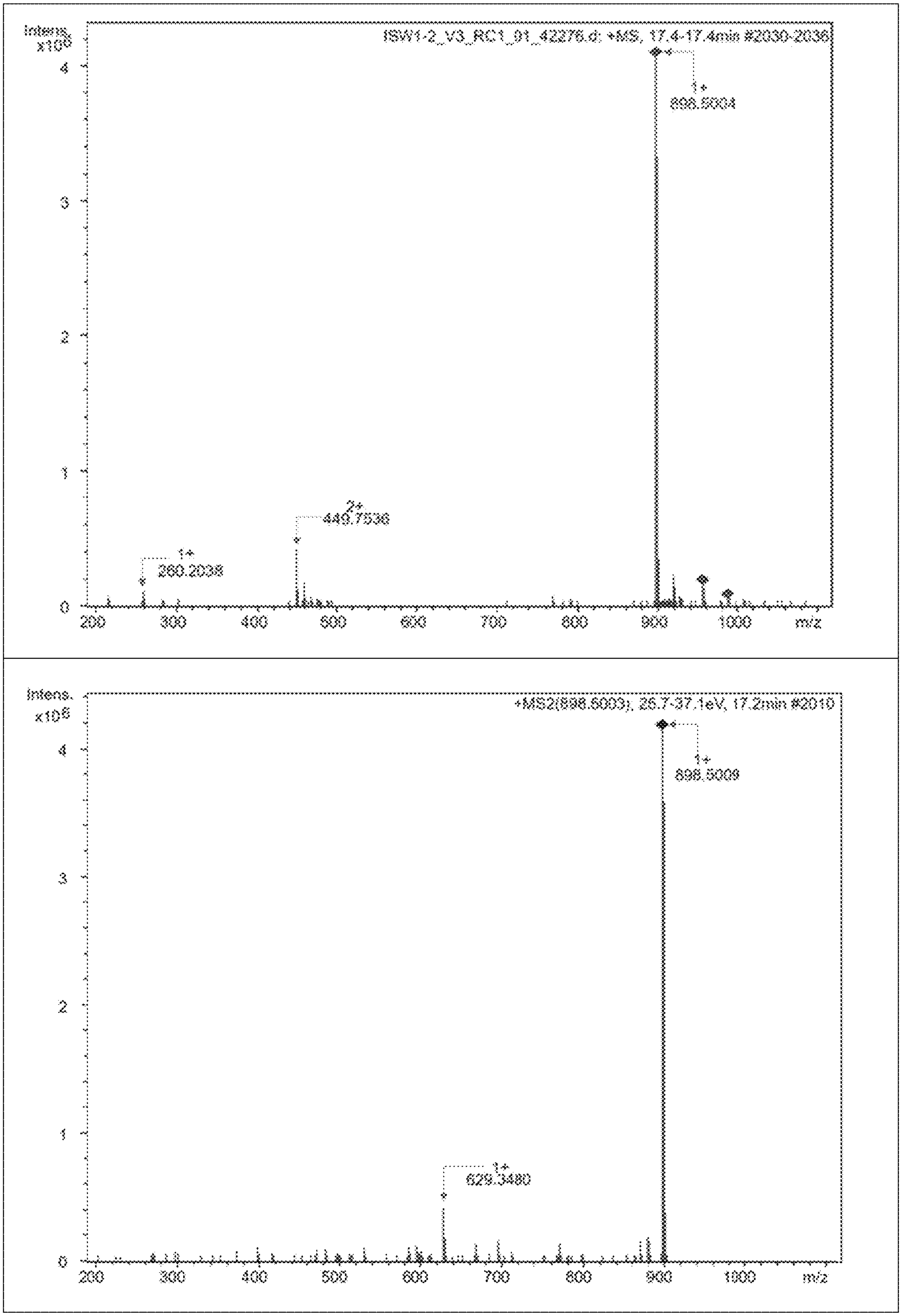
Figure 3:
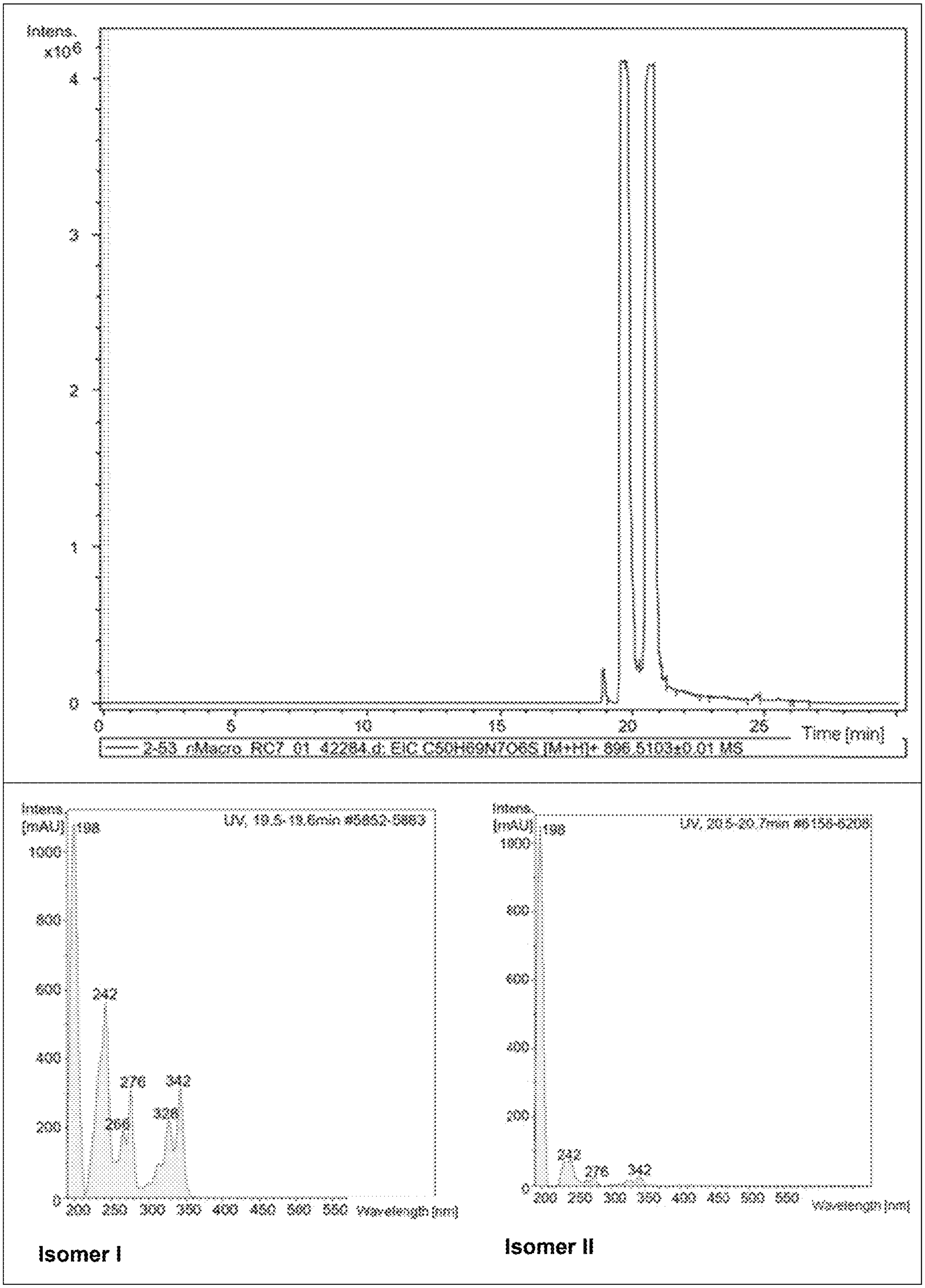
Figure 3:
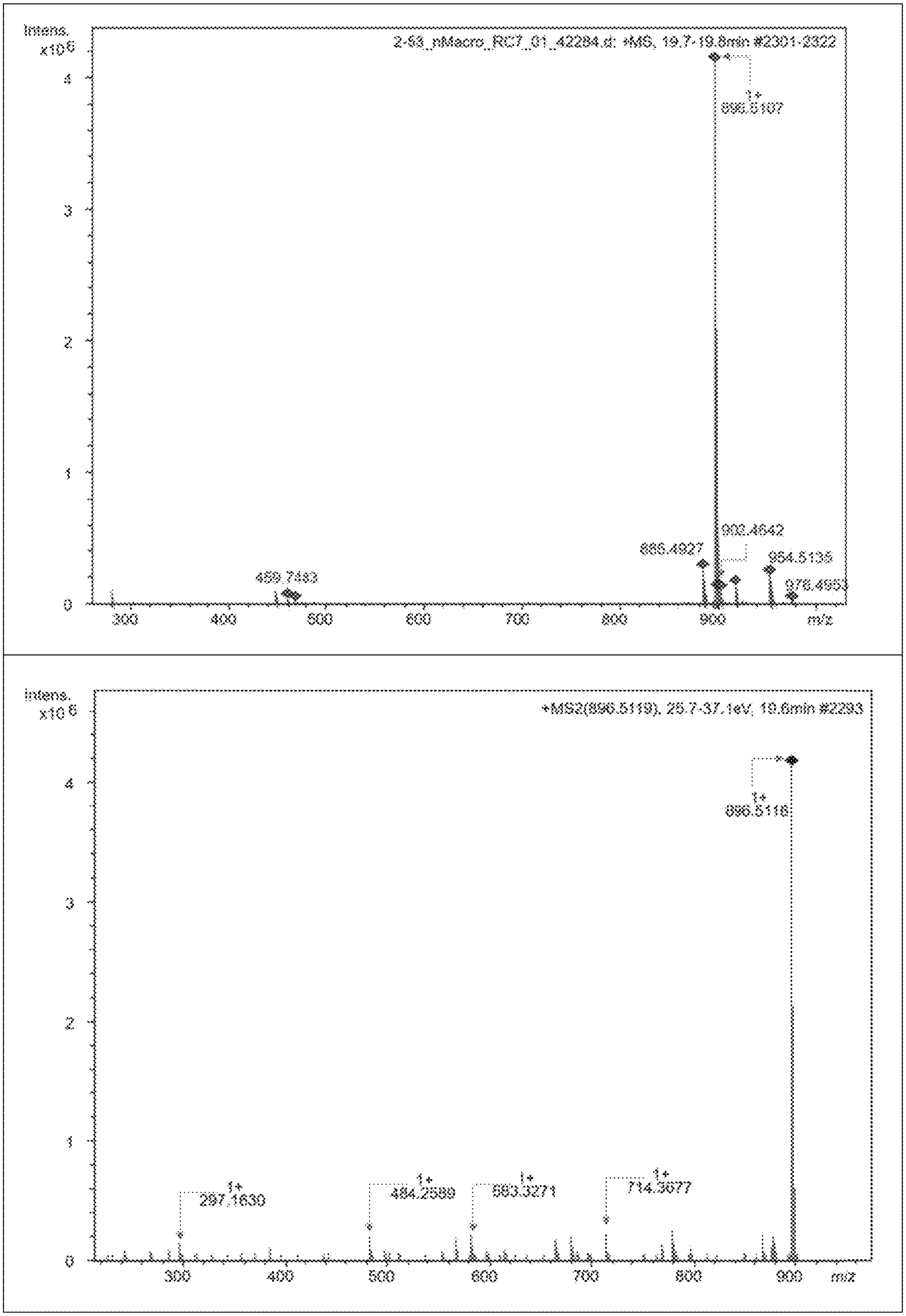
Figure 3:
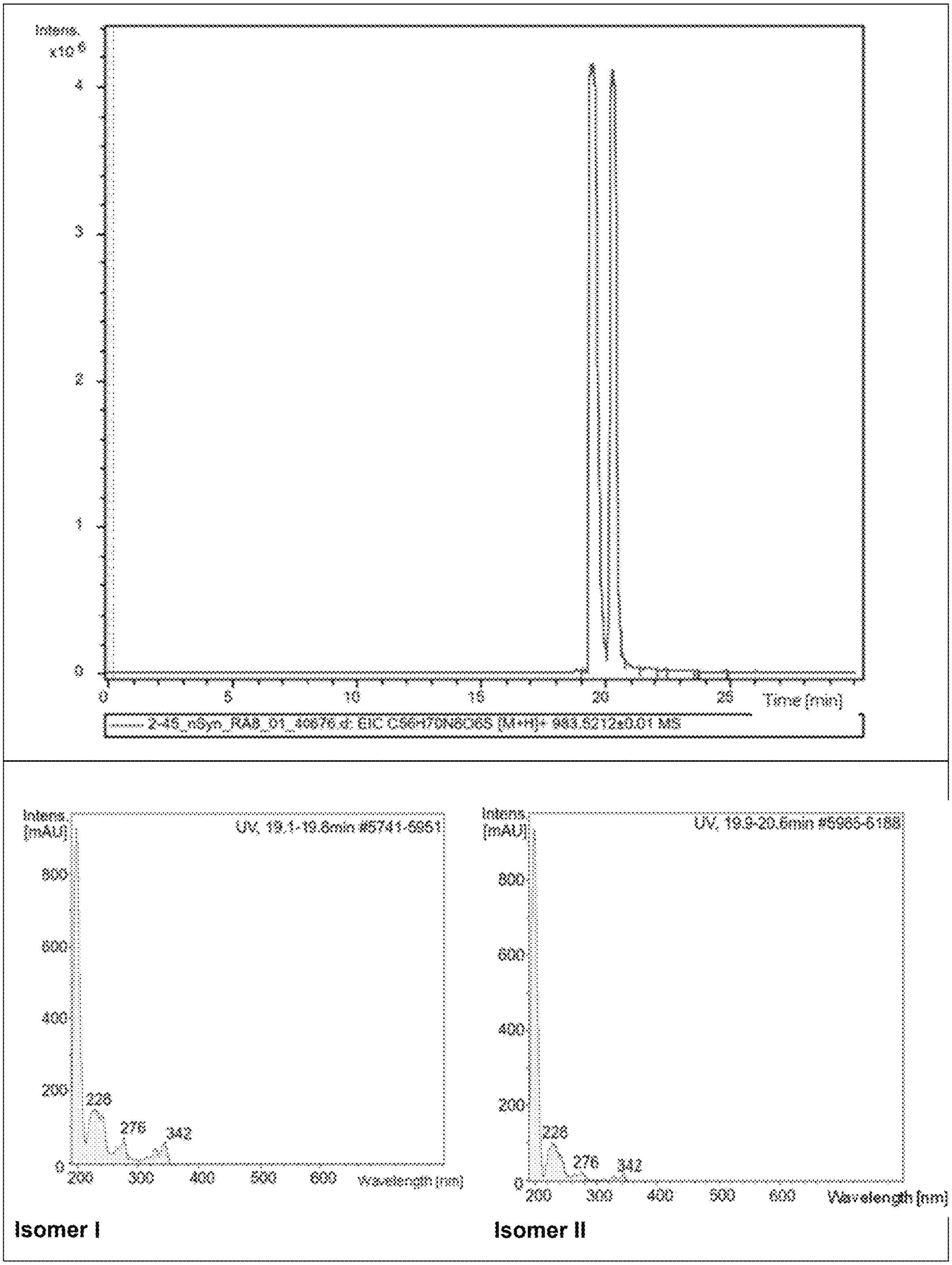
Figure 3:
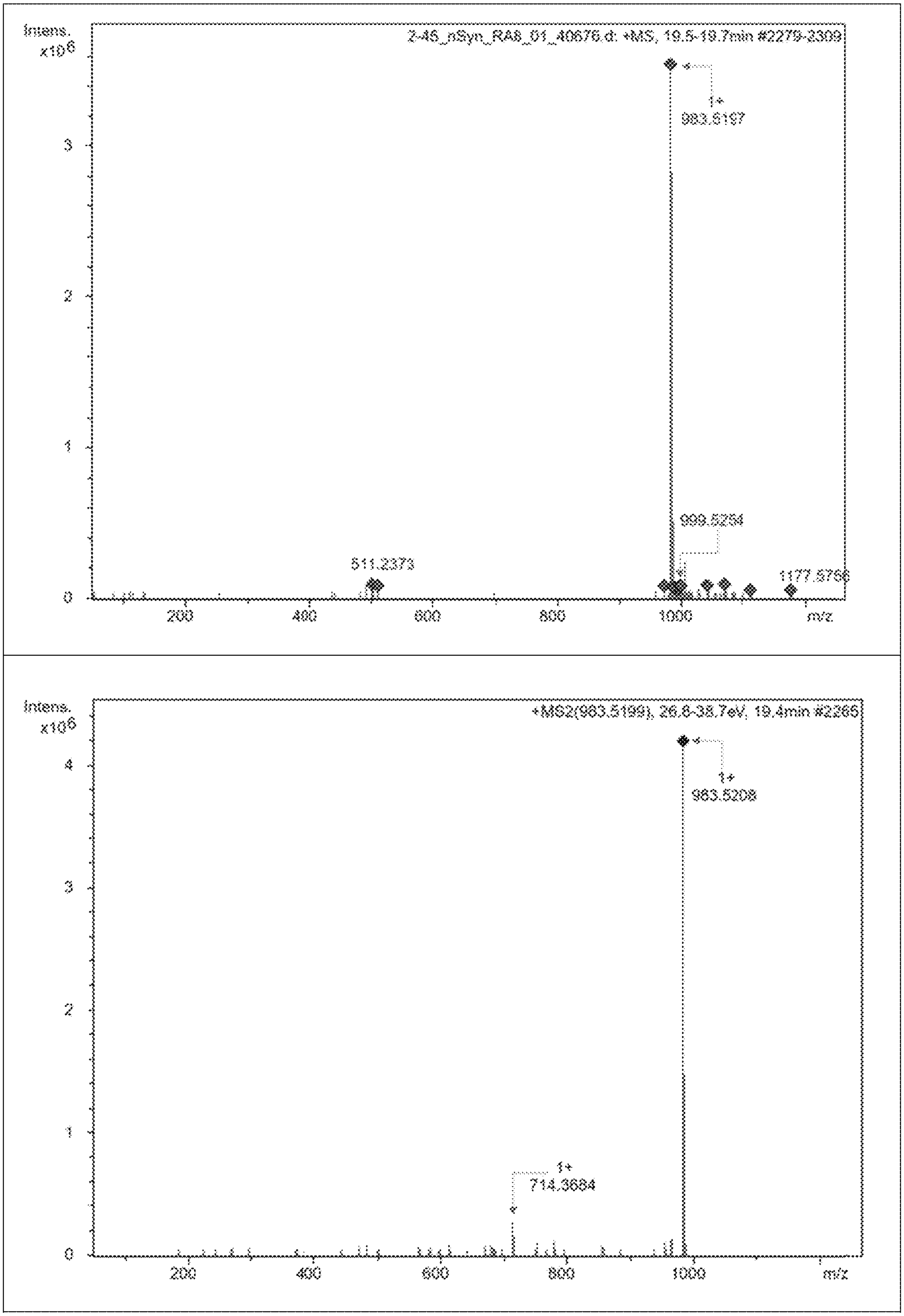
Figure 3:
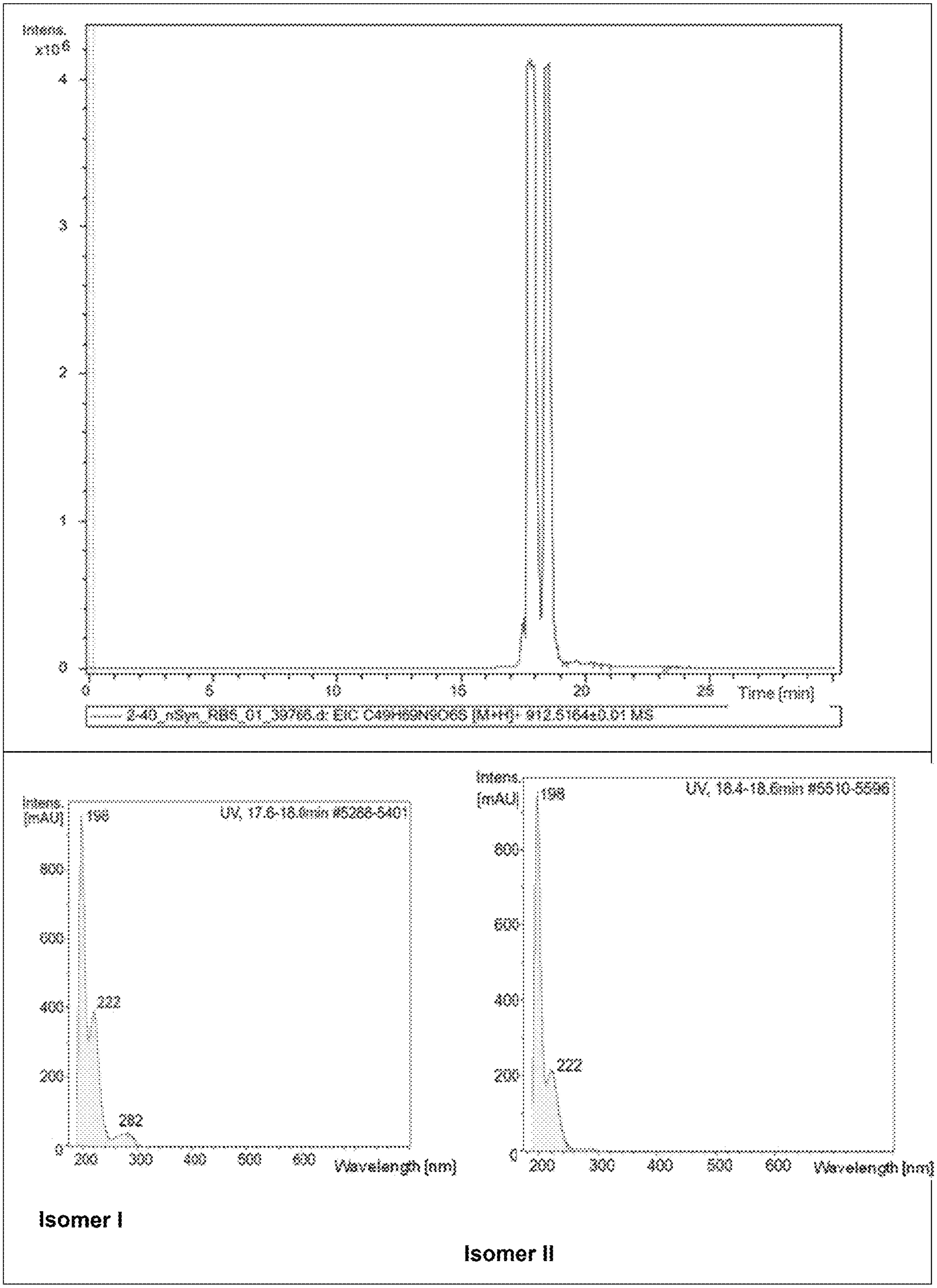
Figure 3:
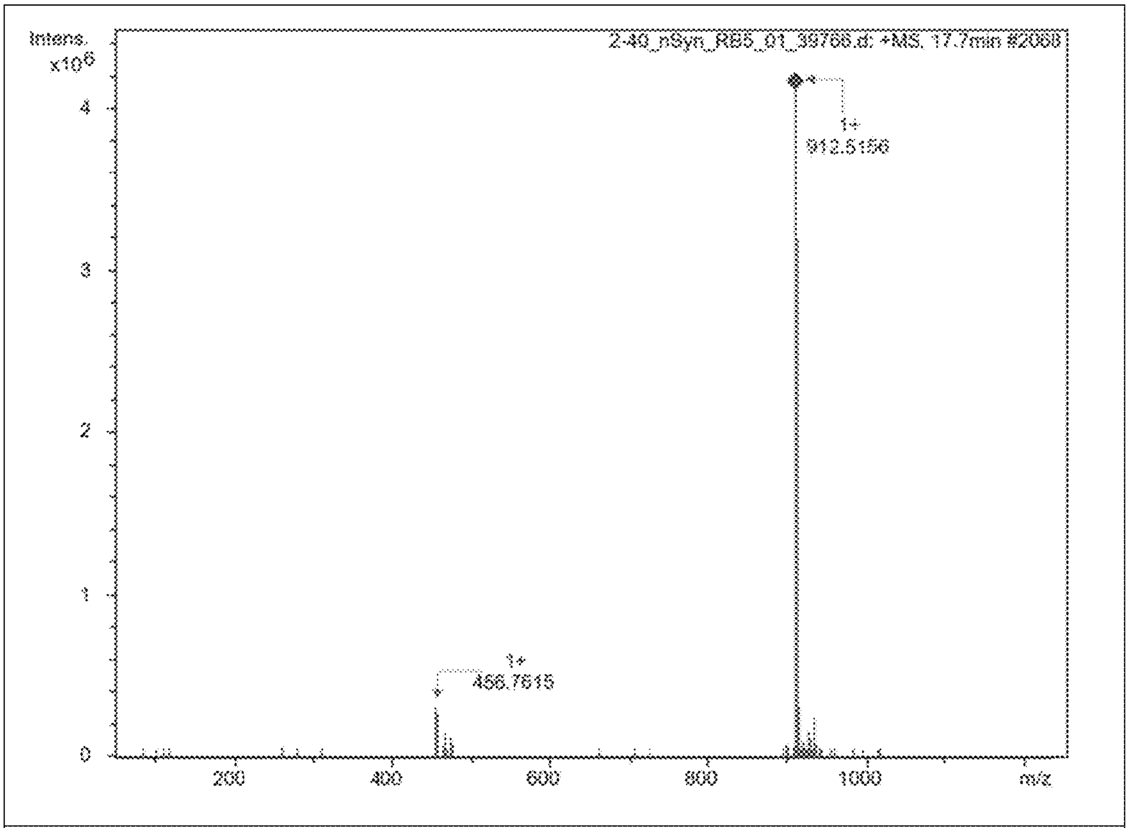
Figure 3:
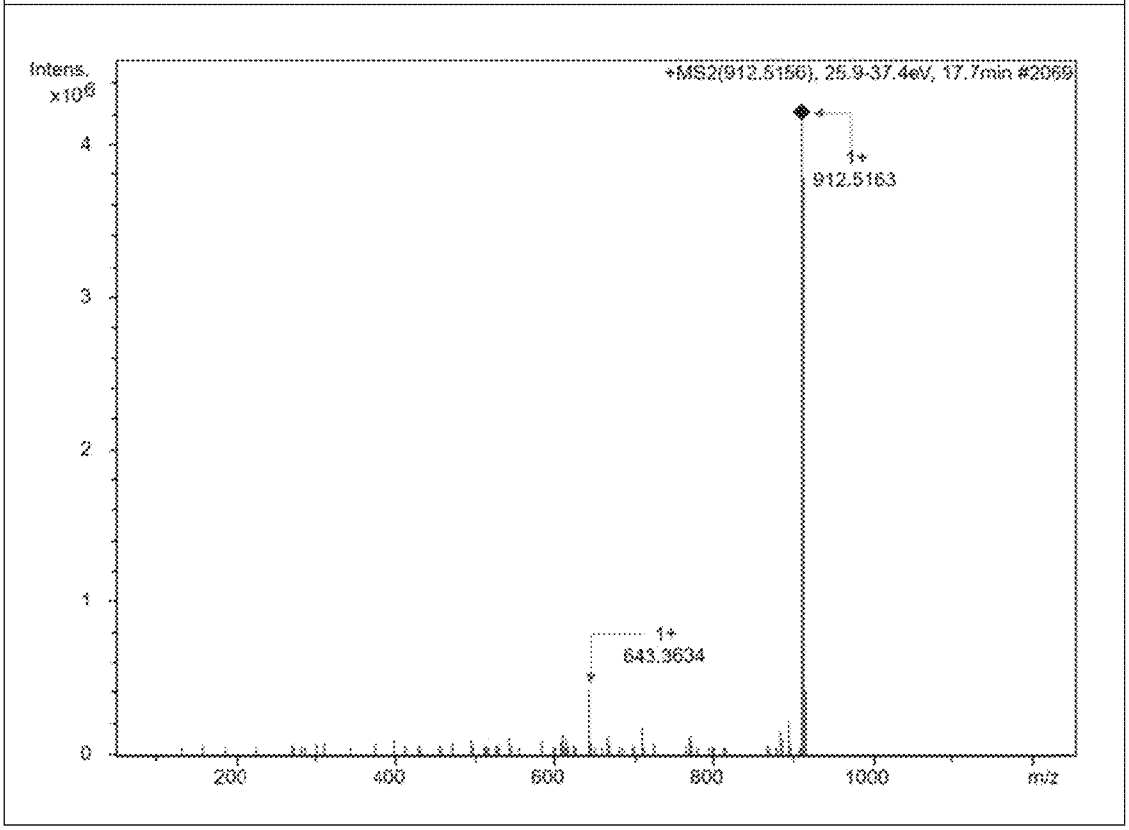
Figure 3:
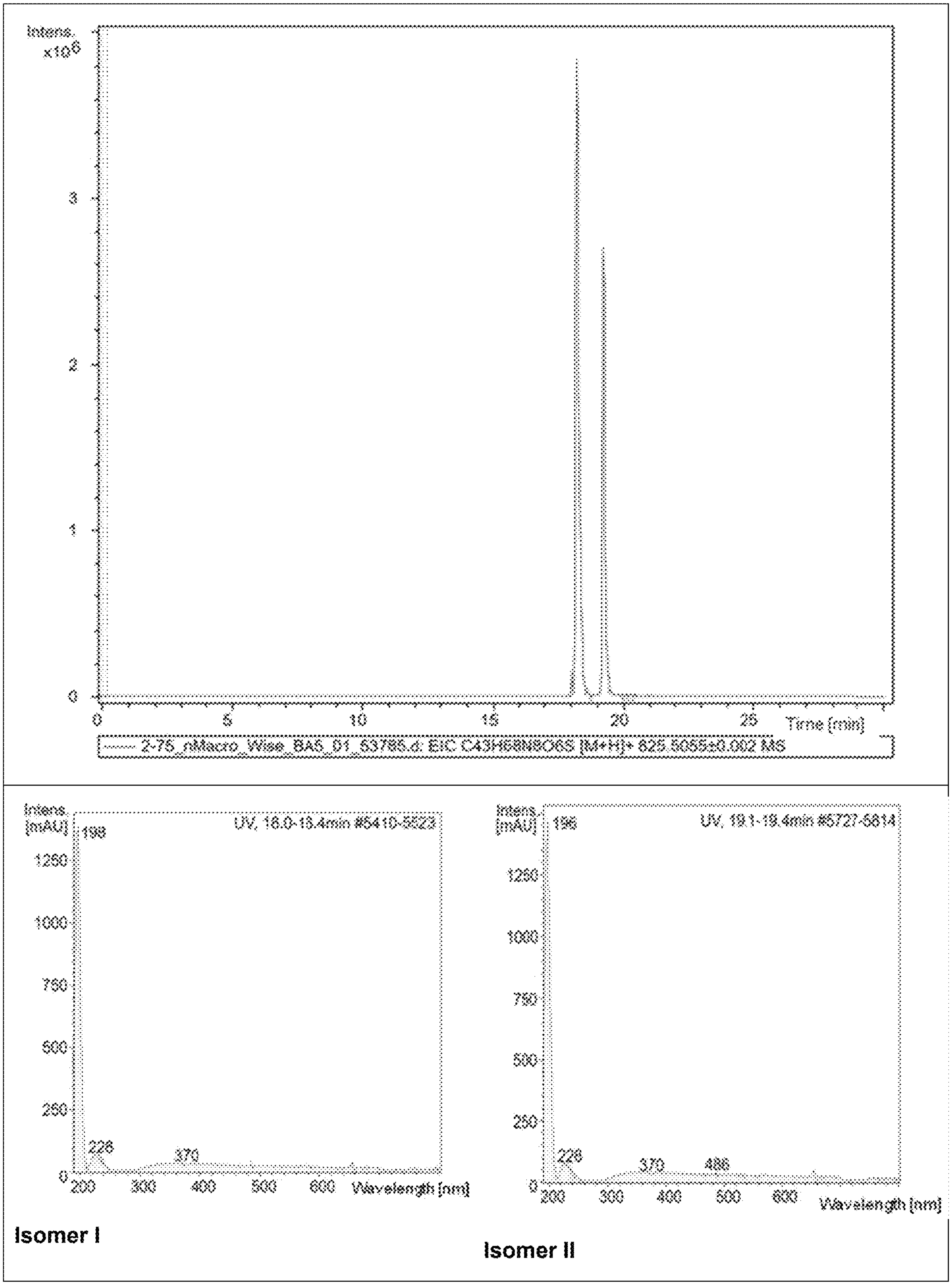
Figure 3:
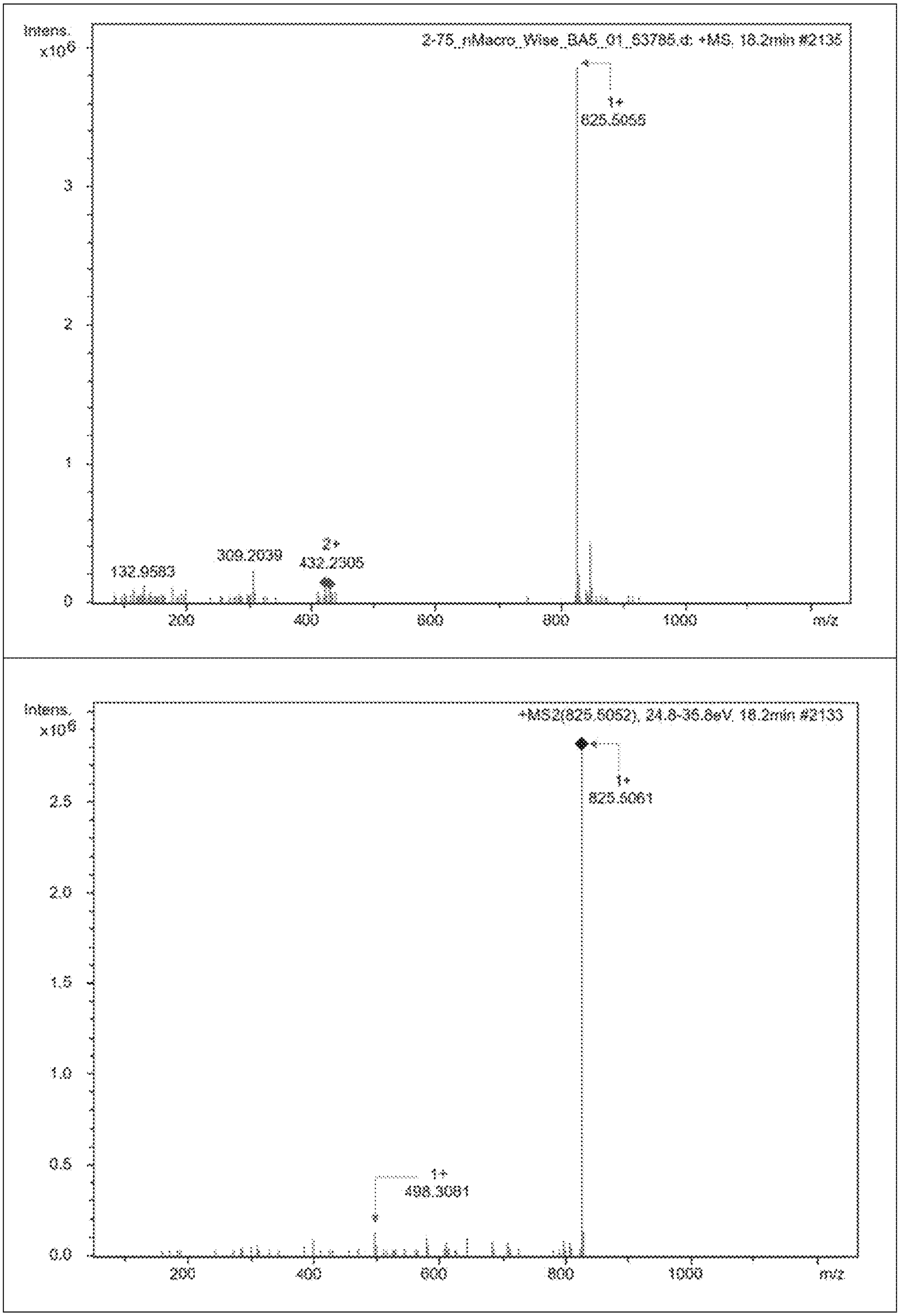
Figure 3:
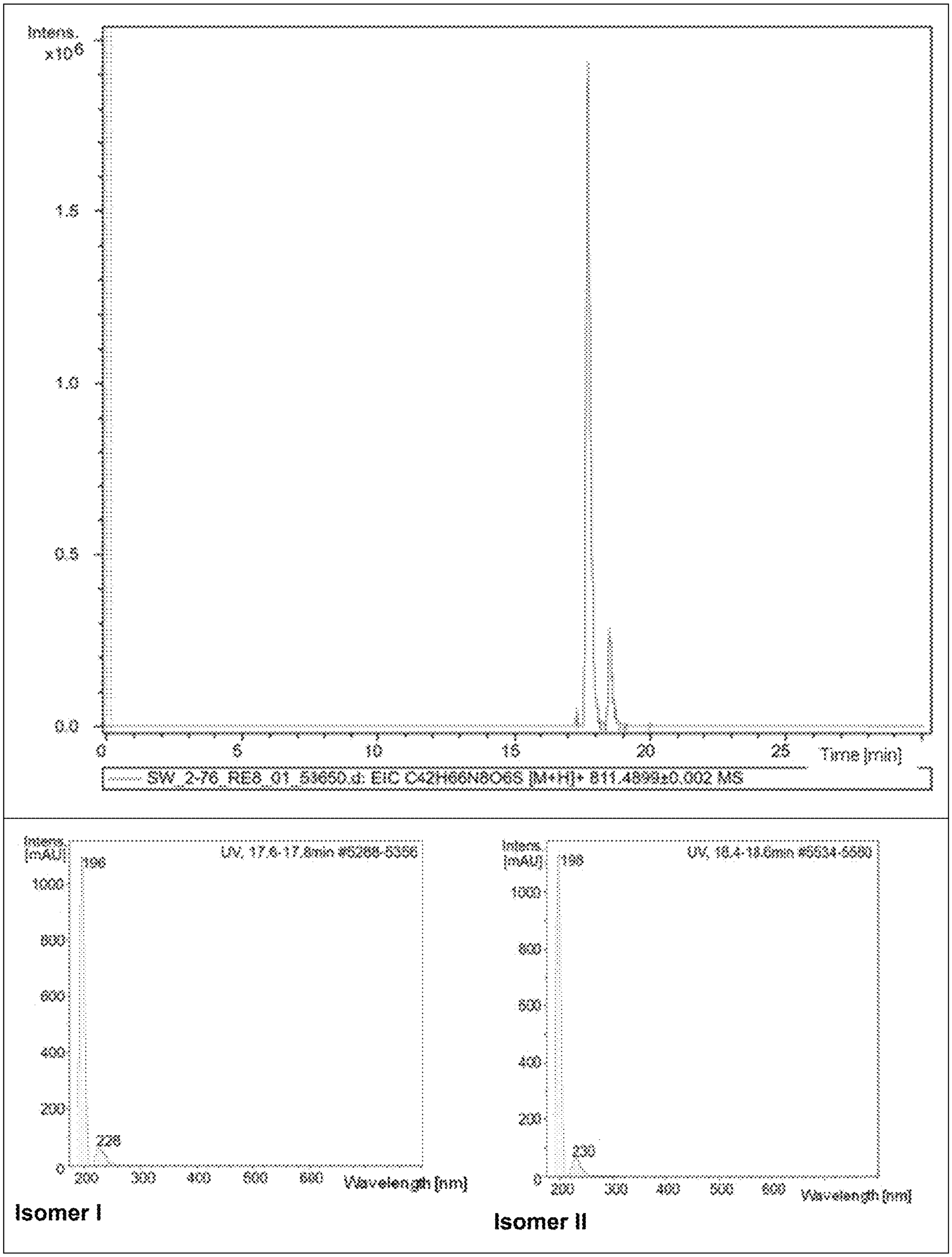
Figure 3:
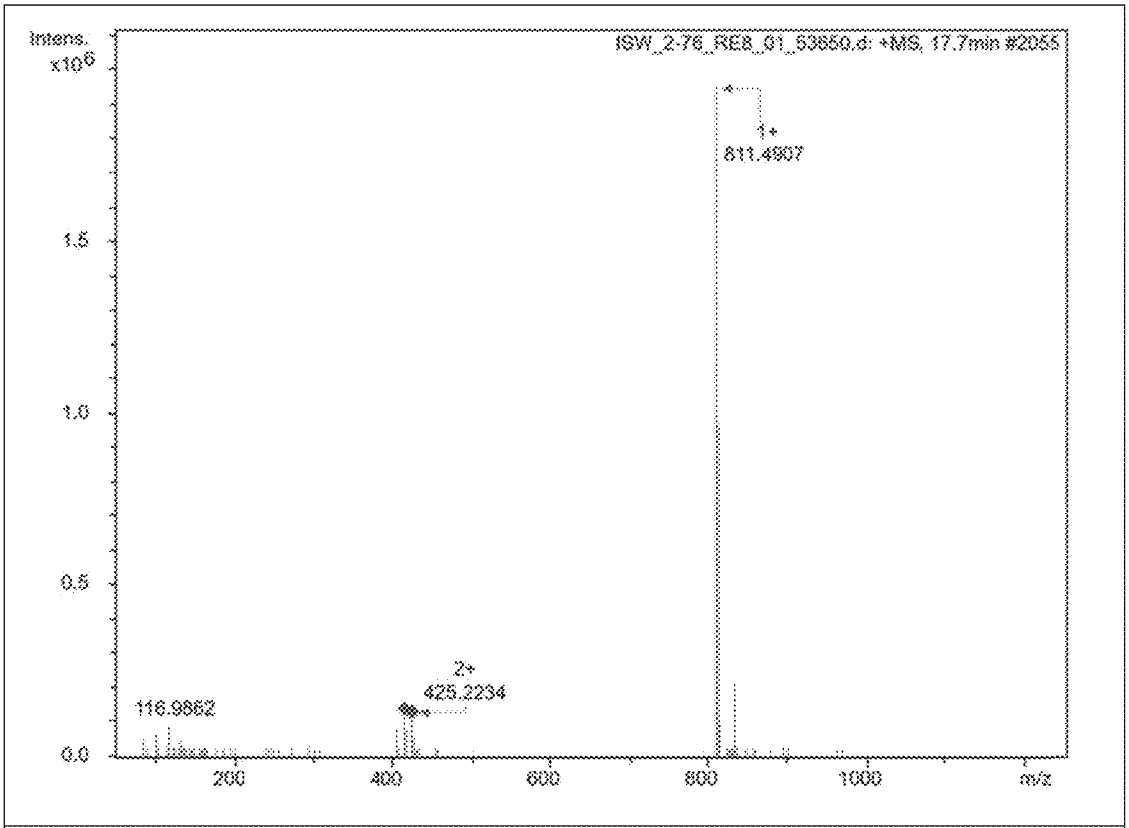
Figure 3:
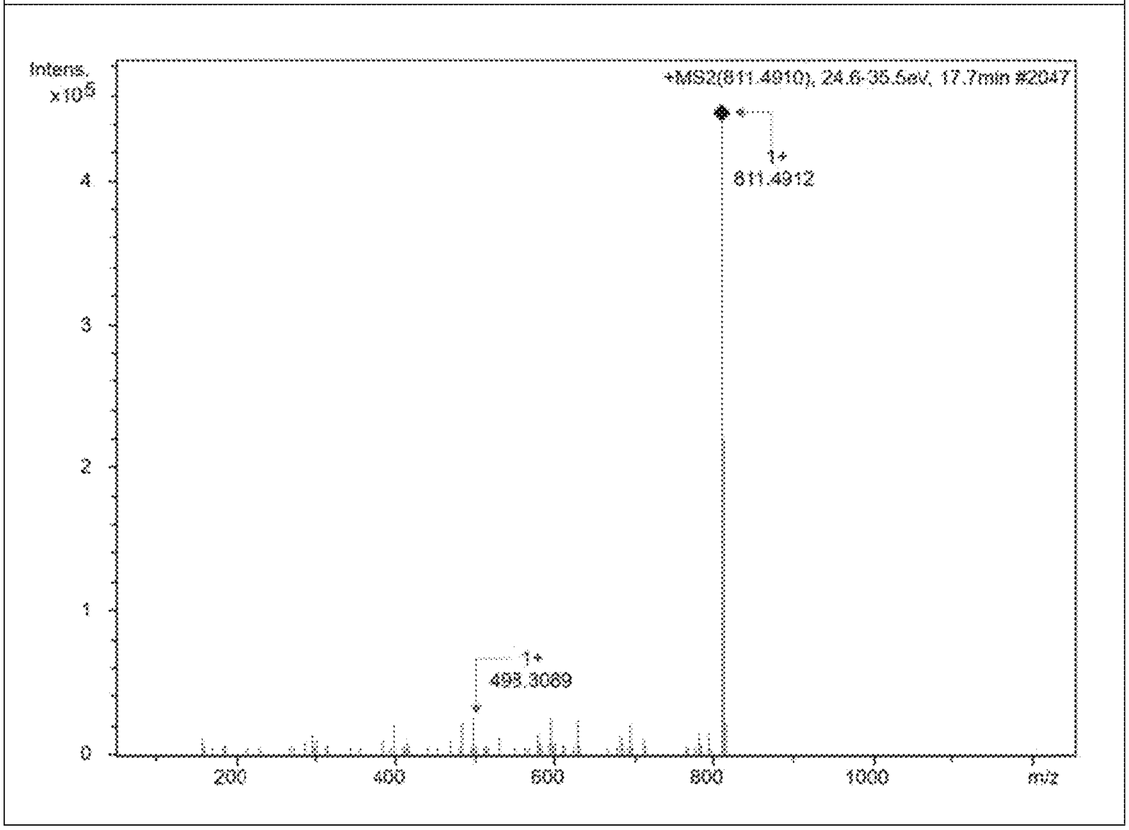
Figure 3:
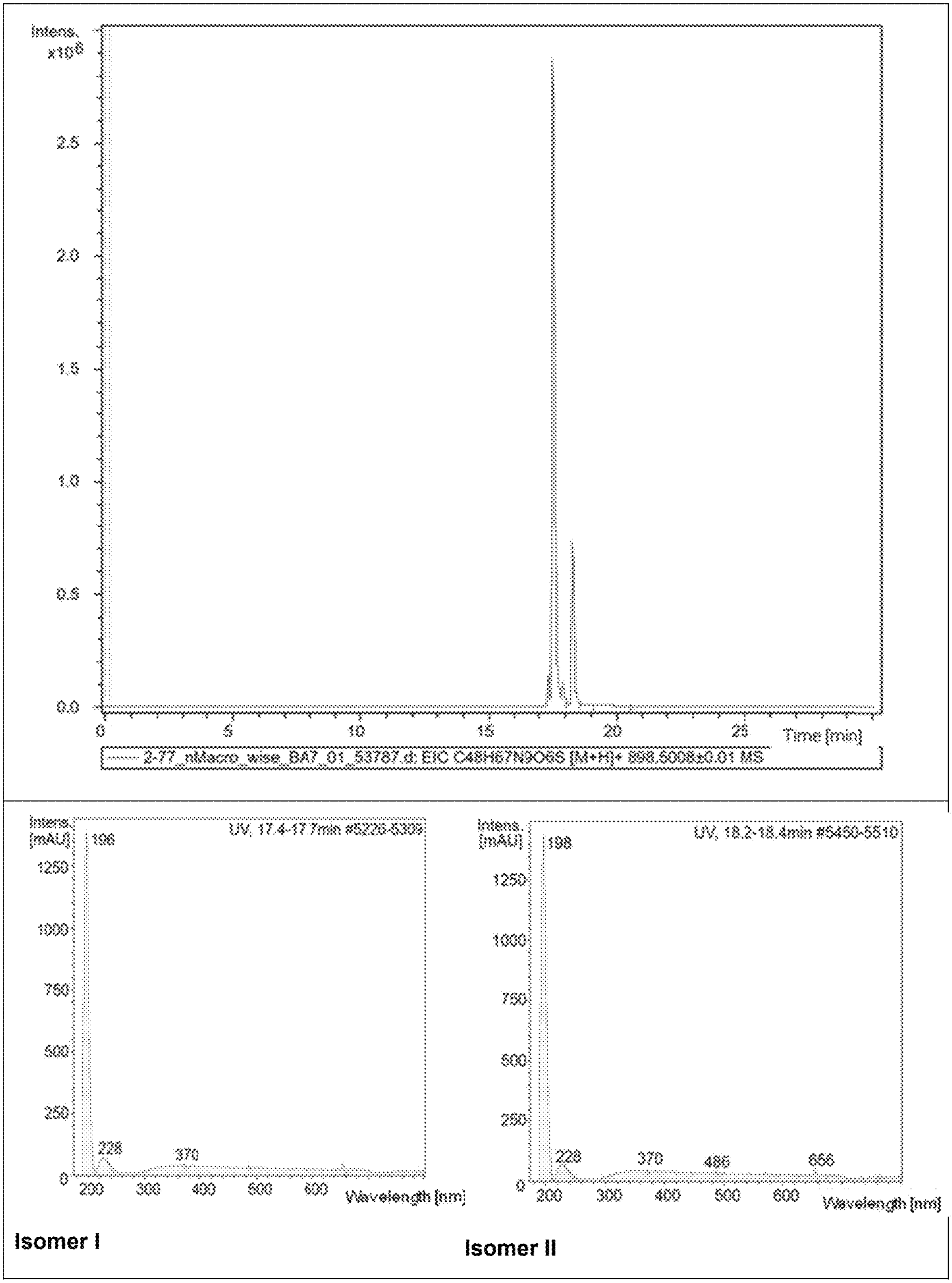
Figure 3:
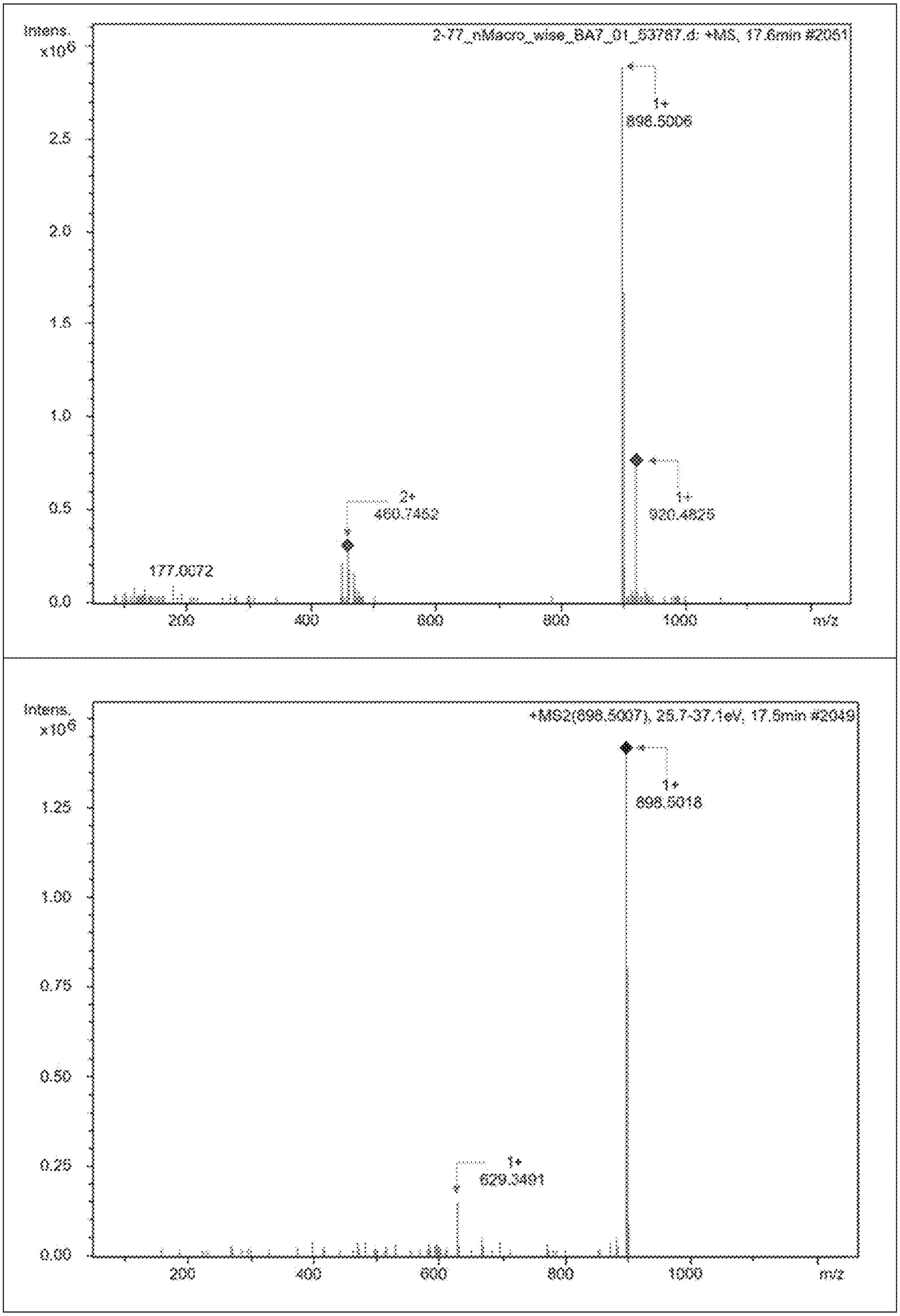
Figure 3:
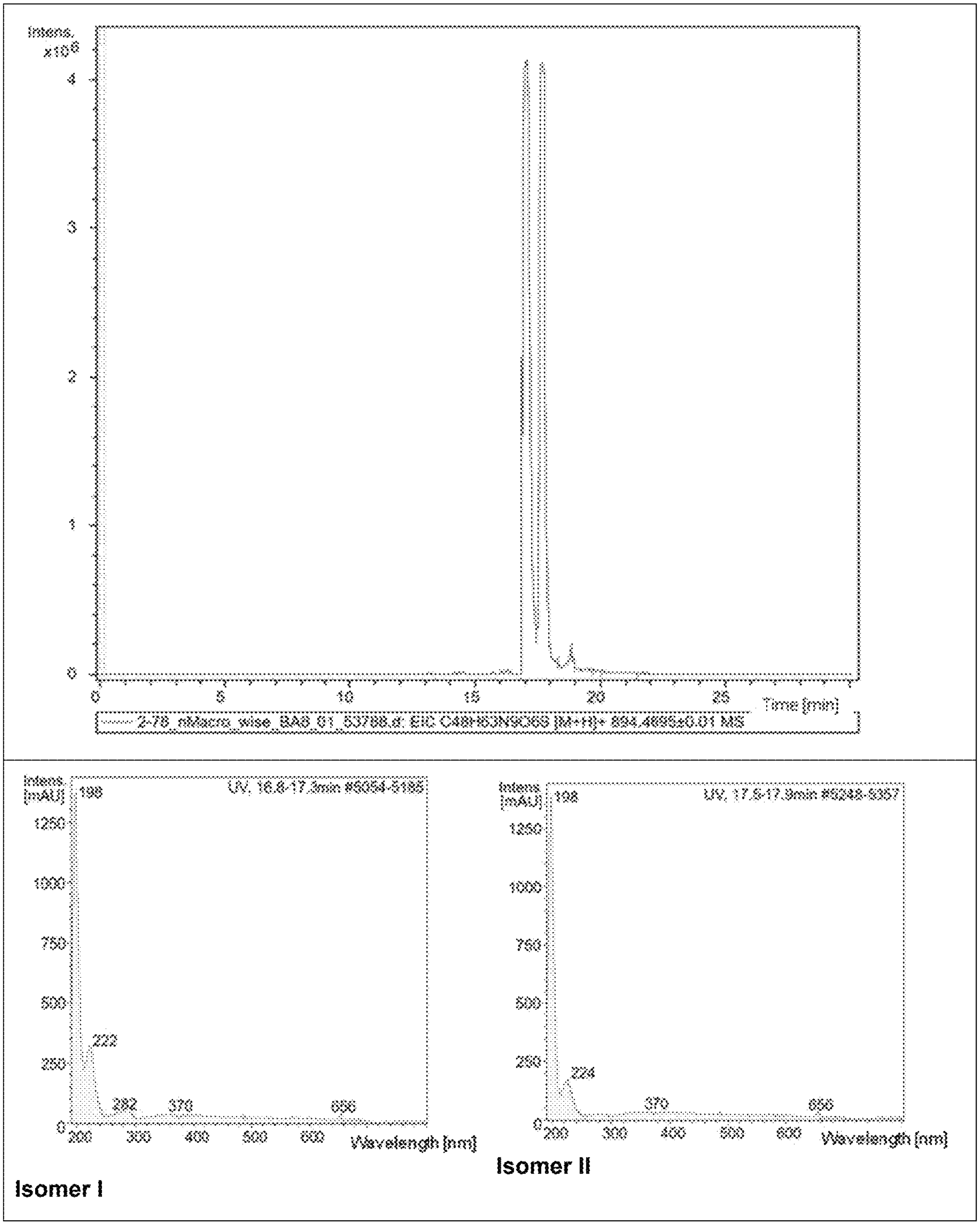
Figure 3:
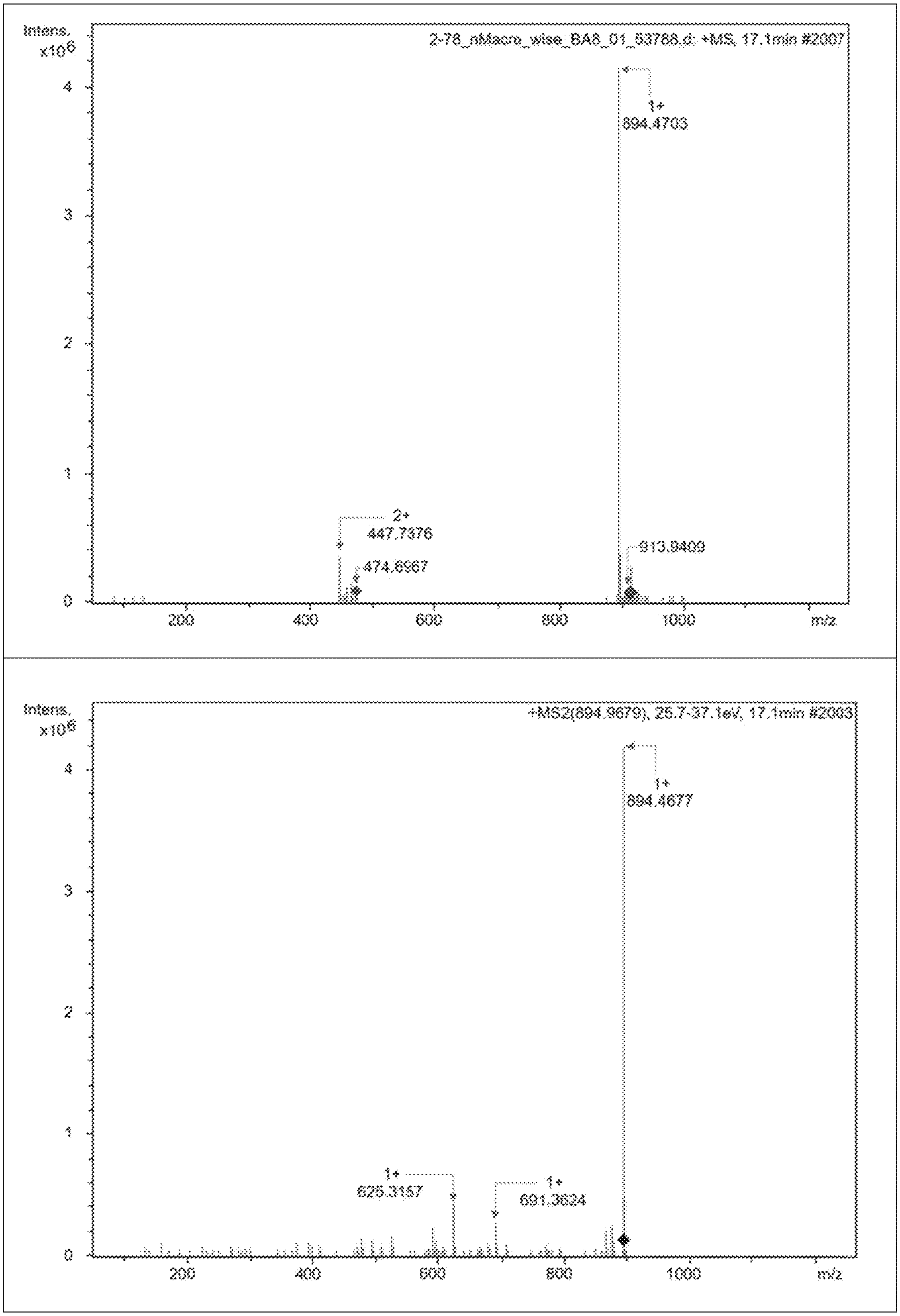

Mass spectra were recorded using a high-resolution ESI QTOF mass spectrometer (MaXis 4G, Bruker Daltonics GmbH) coupled to the HPLC instrument. The ESI source was operated at an atomizer pressure of 2.0 bar, and the dry gas was set to 8.0 L/min at 200° C. (sodium formate as internal calibration gas). MS/MS spectra were acquired with enabled collision energy stepping (i.e., using temporal gradation of collision energies which allows acquisition of MS spectra at lower and higher collision energies). The results of the mass spectrometer analysis are shown in FIG. 3.

C) $^1$H NMR Analysis of the Cyclic Compounds

Routine $^1$H NMR spectra of cyclic compounds I.1, I.2, and I.3 were recorded in DMSO-$D_6$ [$(CD_3)_2SO$] as solvent using a Bruker AMX-600 NMR spectrometer ($^1$H NMR: 600 MHz; Bruker BioSpin GmbH) or a Bruker AvanceIII-700 NMR spectrometer ($^1$H NMR: 700 MHz; Bruker BioSpin GmbH) at 30° C. (303 K).

Figure 4:
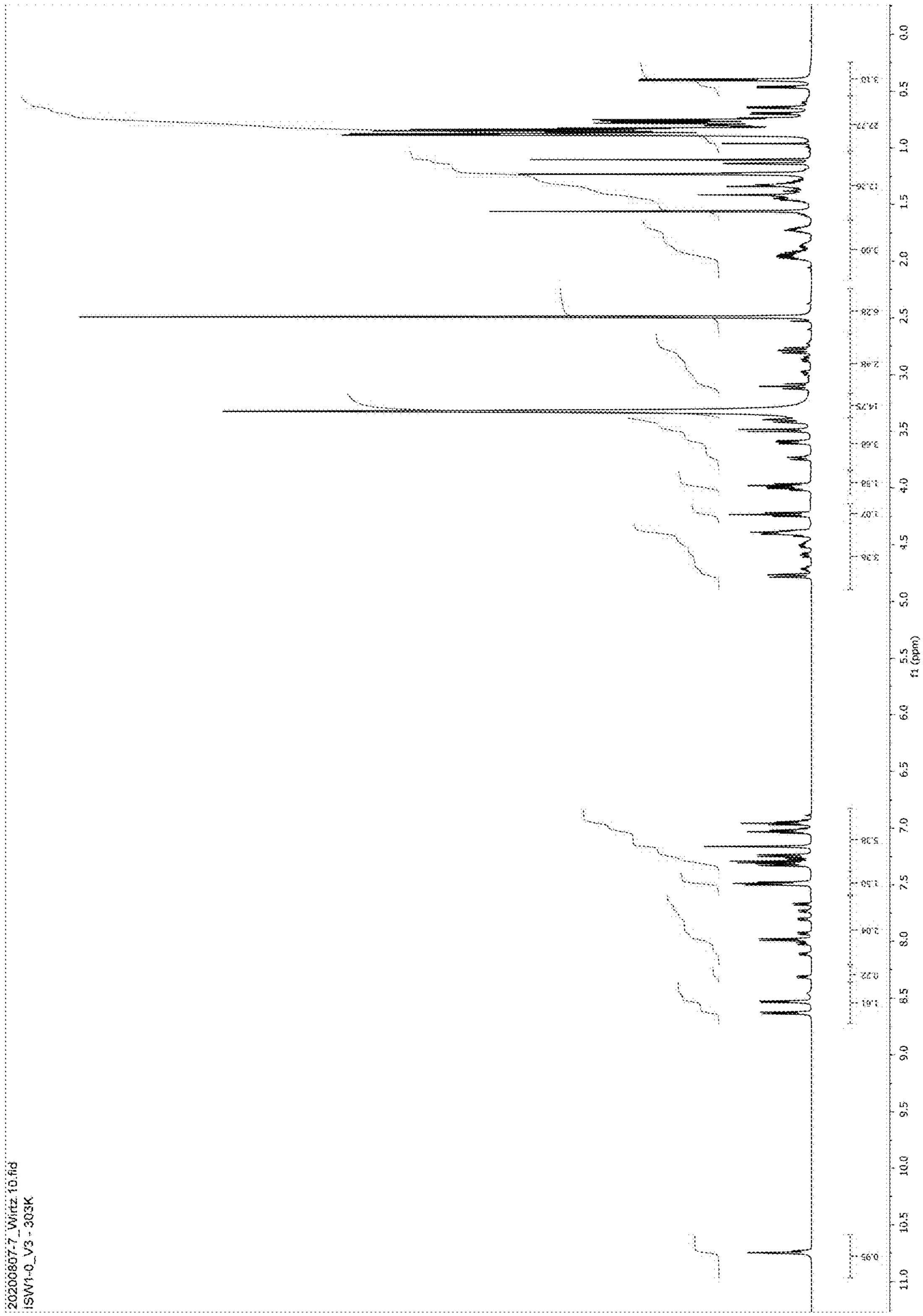
FIG. 4: Spectra of $^1$H-NMR analysis of the cyclic compounds: (A) $^1$H-NMR spectrum of compound I.1 (600 MHz, DMSO-$D_6$, 303 K), (B) $^1$H-NMR spectrum of compound I.2 (700 MHz, DMSO-$D_6$, 303 K), (C) $^1$H-NMR spectrum of compound I.3 (600 MHz, DMSO-$D_6$, 303 K); (D) $^1$H-NMR spectrum of compound I.19 (600 MHz, DMSO-$D_6$, 303 K); (E) $^1$H-NMR spectrum of compound I.20 (600 MHz, DMSO-$D_6$, 303 K); (F) $^1$H-NMR spectrum of compound I.21 (600 MHz, DMSO-$D_6$, 303 K); (G) $^1$H-NMR spectrum of compound I.22 (600 MHz, DMSO-$D_6$, 303 K); (H) $^1$H-NMR spectrum of compound I.23 (600 MHz, DMSO-$D_6$, 303 K); (I) $^1$H-NMR spectrum of compound I.24 (600 MHz, DMSO-$D_6$, 303 K); recorded with a Bruker AMX-600 NMR spectrometer or a Bruker AvanceIII-700 NMR spectrometer (Bruker BioSpin GmbH).
Figure 4:
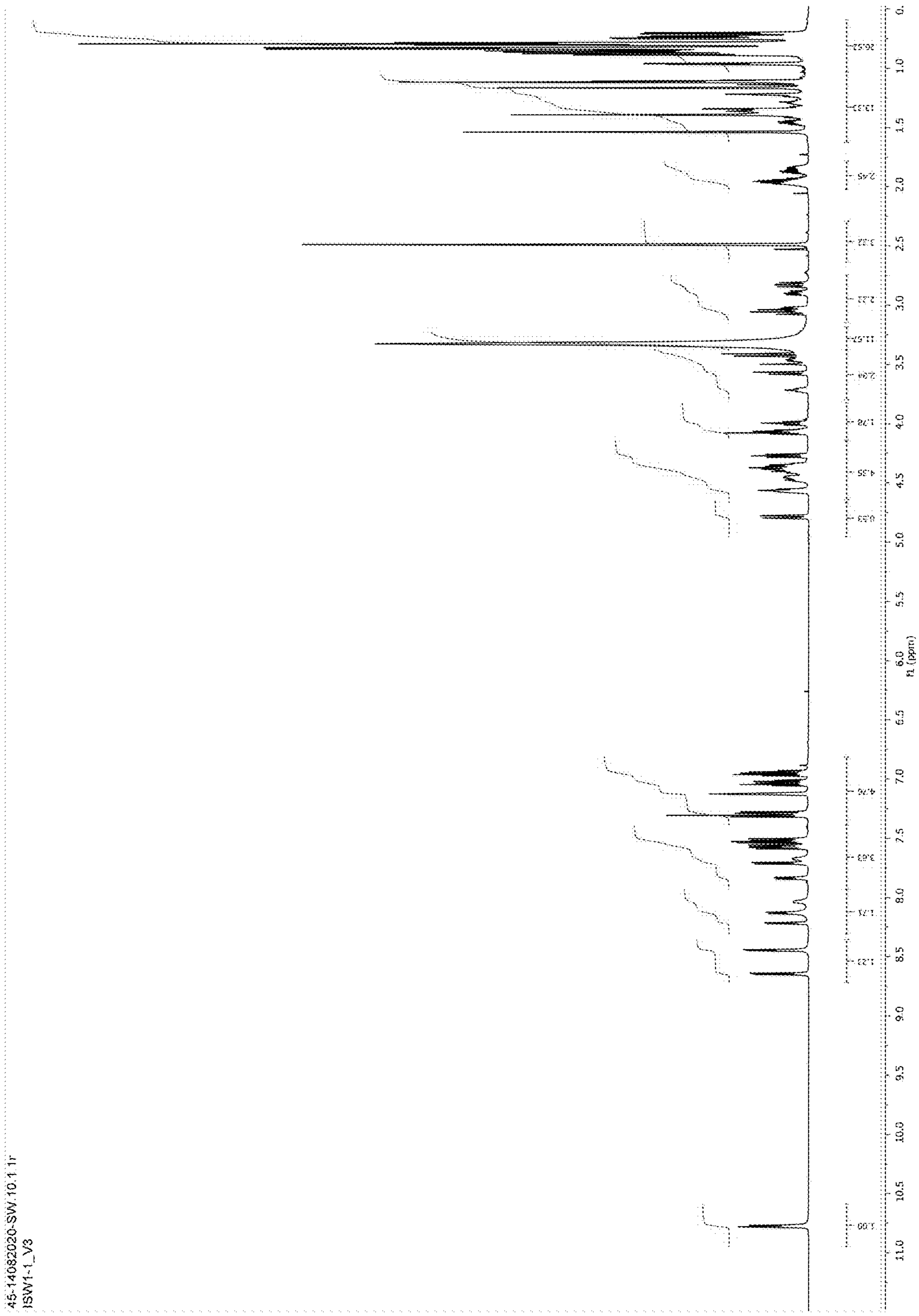
Figure 4:
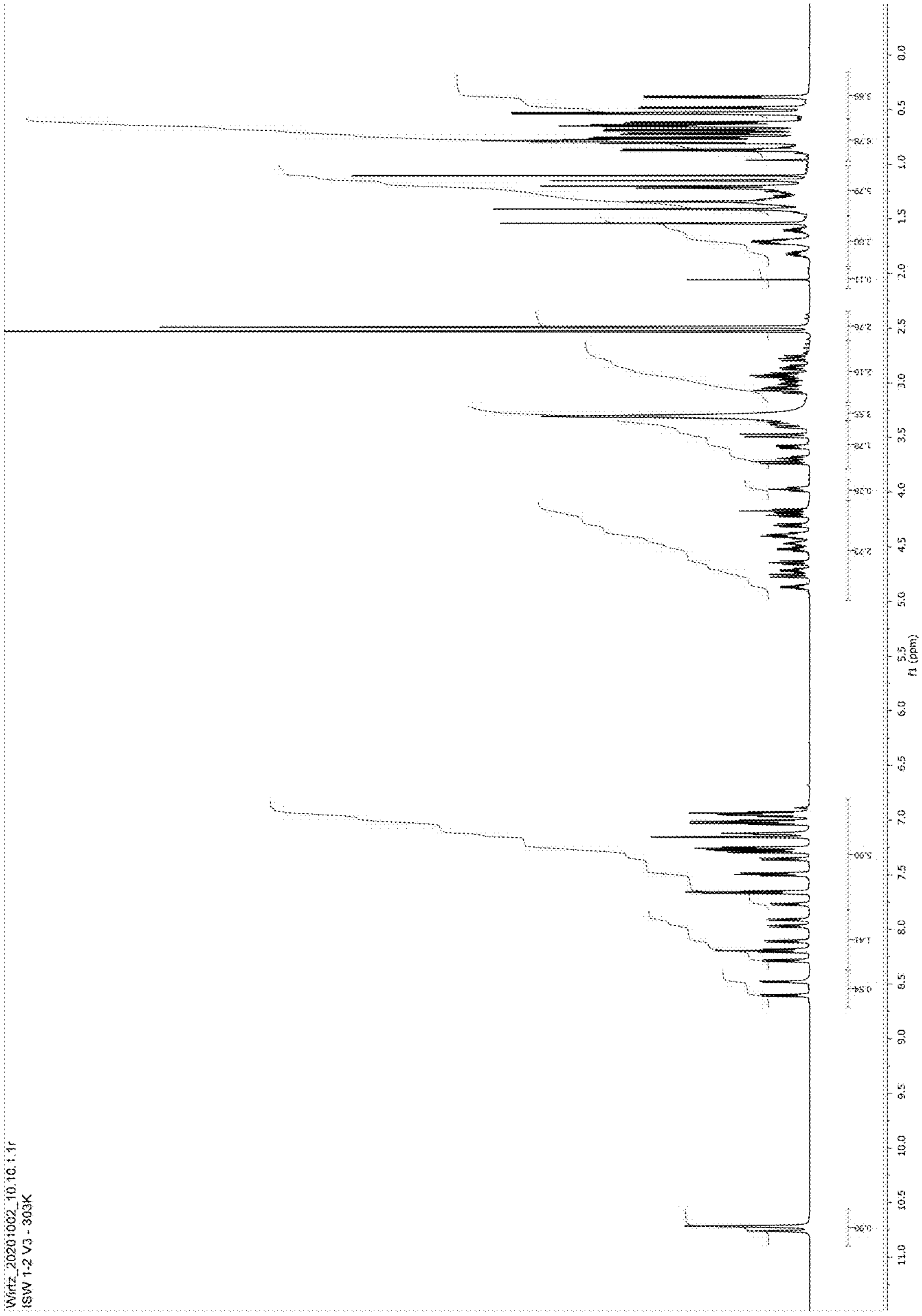
Figure 4:
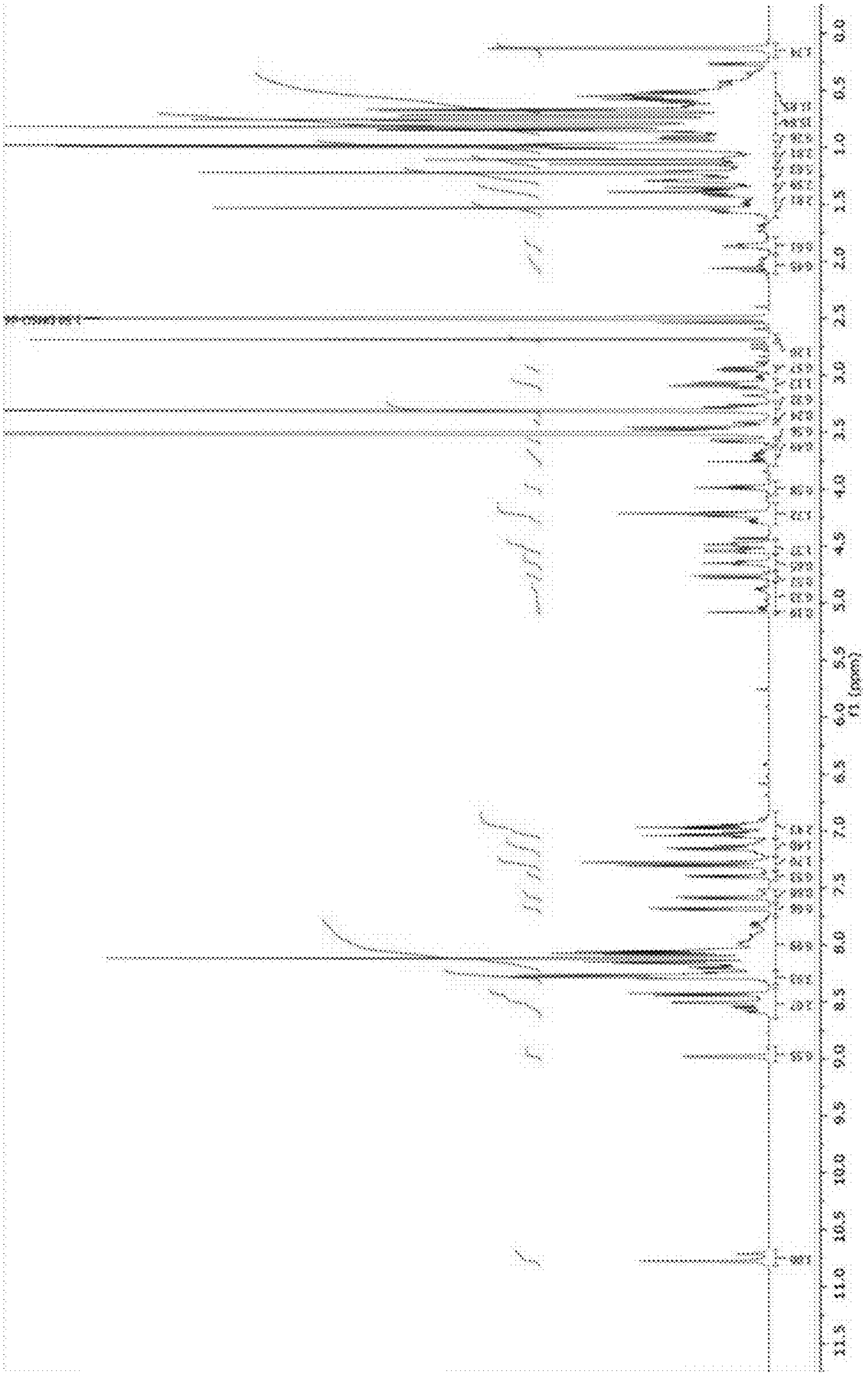
Figure 4:
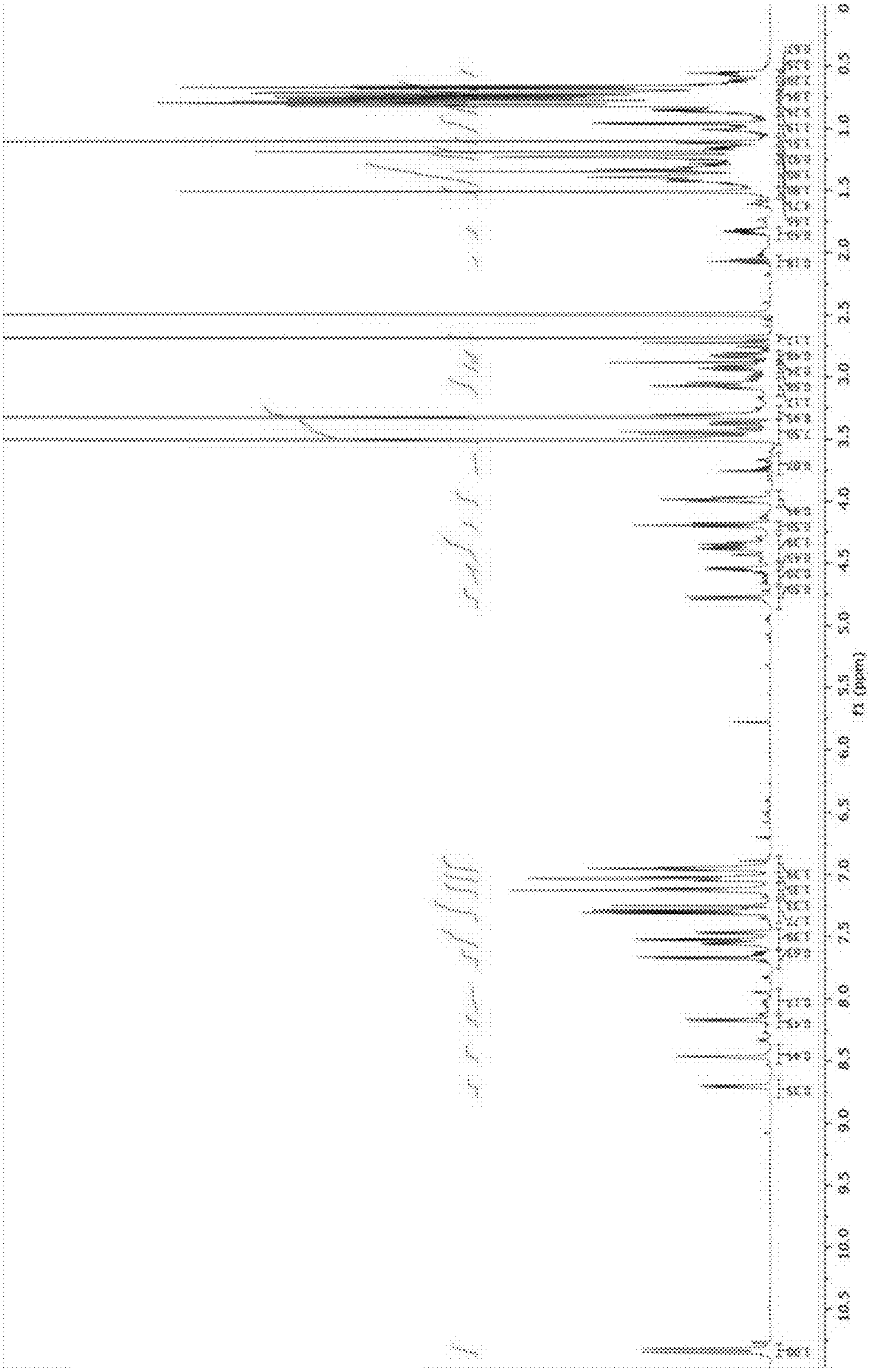
Figure 4:
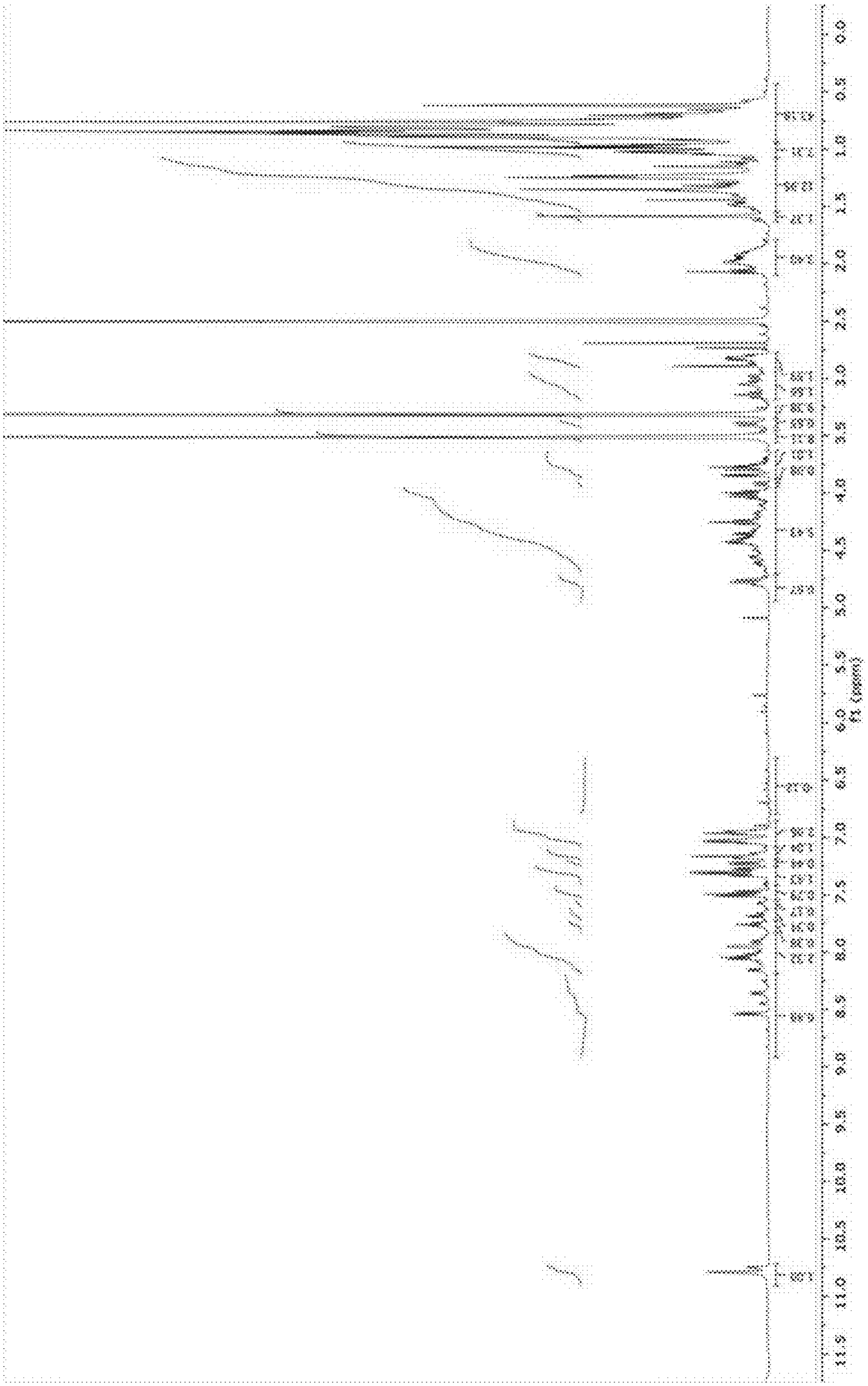
Figure 4:
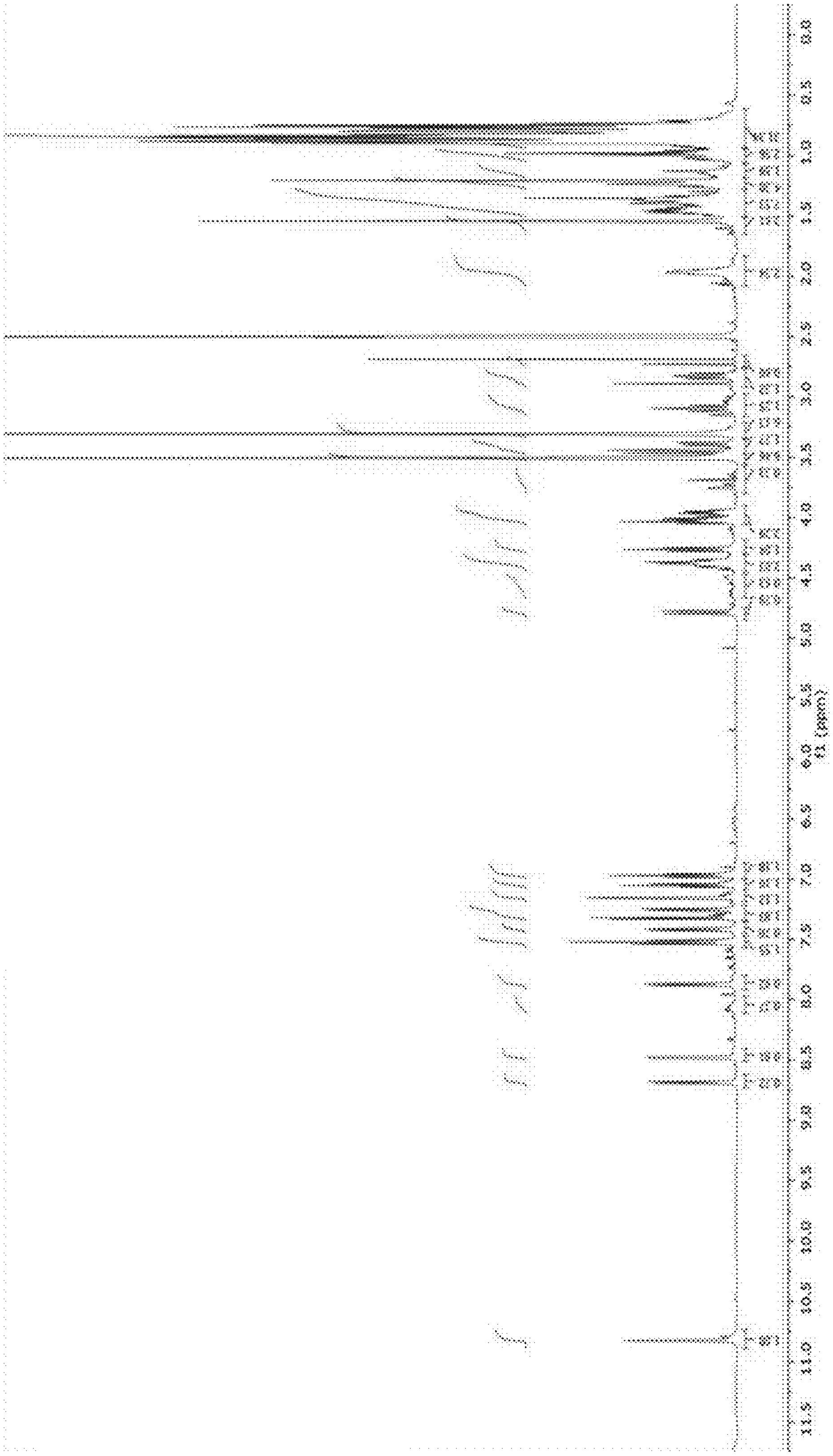
Figure 4:
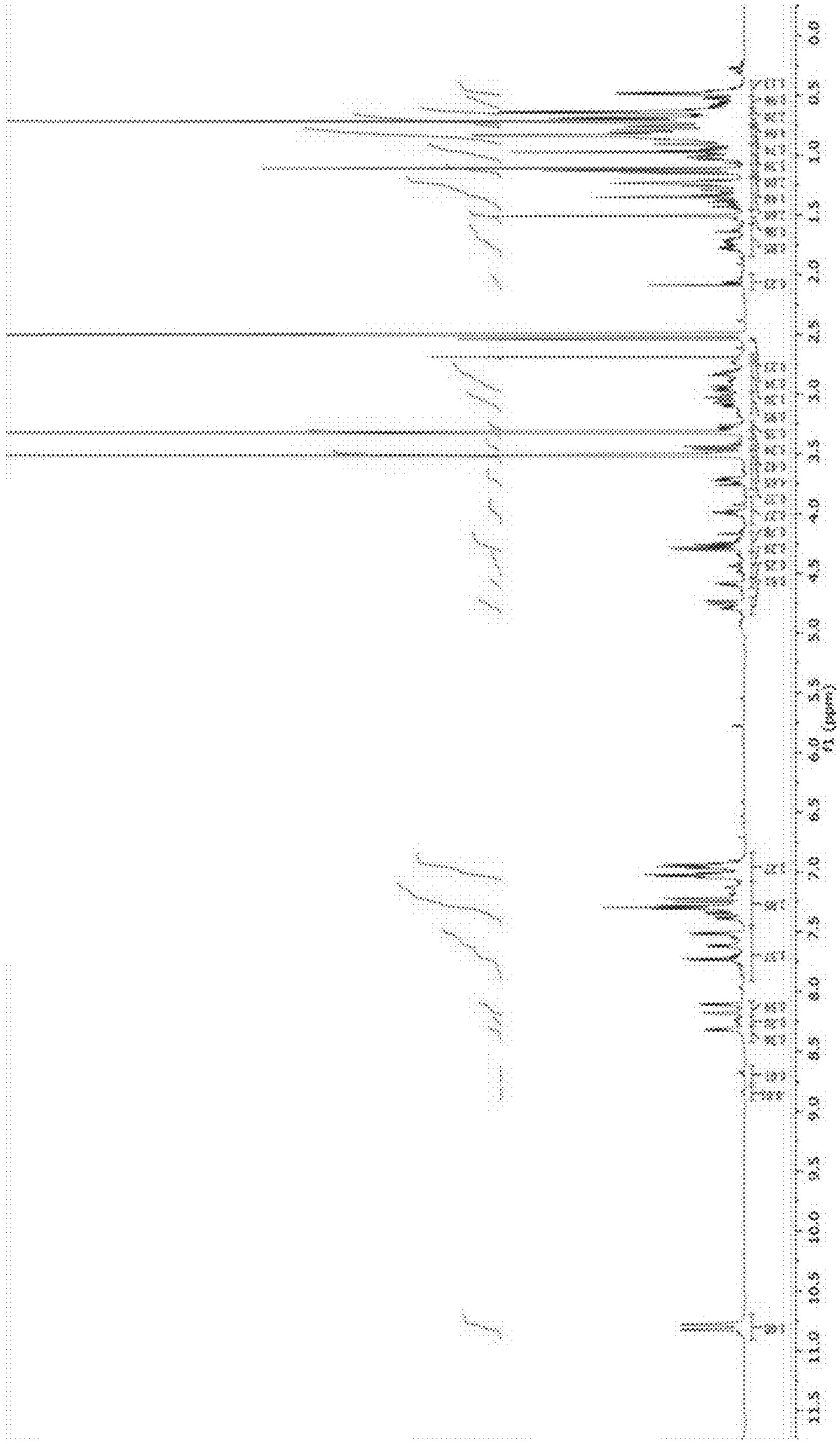
Figure 4:
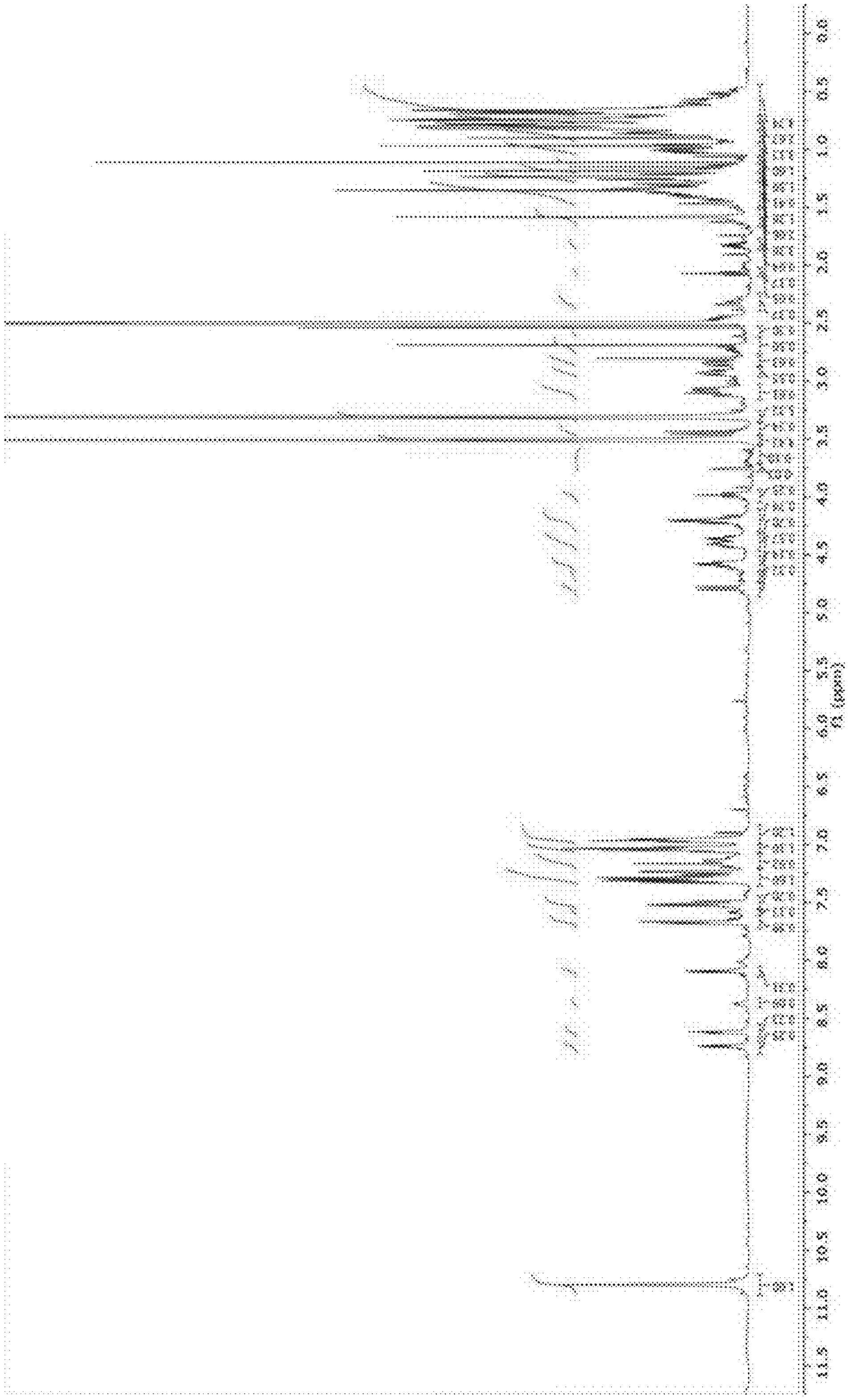

The results of the $^1$H NMR analysis are shown in FIG. 4. All chemical shifts are given in parts per million (ppm) relative to the solvent reference peak of $(CD_3)_2SO$ (δH 2.50). Coupling constants are given in Hertz.

Example 4: Bioassay in *S. aureus* LugIEFGH Vs. *S. aureus* Wild Type

The minimum inhibitory concentrations (MIC) of cyclic compound I.1 (ISW 1-0) according to the invention, and of the known compounds lugdunin and CCCP (carbonylcyanide-3-chrlophenylhydrazone) were compared for two *Staphylococcus aureus* strains.

The two *Staphylococcus aureus* strains were 1) *Staphylococcus aureus* N315 wild type (*S. aureus* Wt), and 2) the genetically modified strain *S. aureus* N315 LugIEFGH. This strain (*S. aureus* LugIEFGH) additionally carries the genes for the lugdunin ABC transporters LugIEFGH from the lugdunin producer *S. lugdunensis*. Cells from the two strains were spiked in serial dilutions with compound I.1, or the known compounds lugdunin or CCCP, and the MIC was determined in each case. MIC values were determined as described in Example 3 A), wherein MIC is defined as the concentration of an antimicrobial compound to be tested at which the optical density (OD600) reaches less than 75% of the control without the antimicrobial compound to be tested (MIC75).

Figure 5:
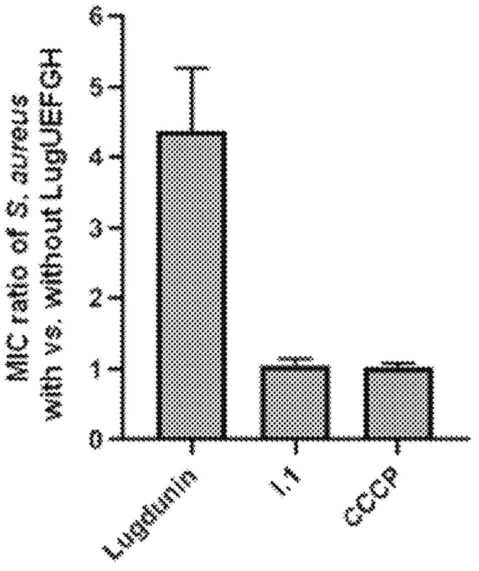
FIG. 5: Ratio of the minimum inhibitory concentration (MIC) of the cyclic compound I.1 according to the invention, and the known compounds lugdunin and CCCP (carbonyl cyanide-3-chrlophenylhydrazone) for a recombinant *S. aureus* strain with the lugdunin transporter genes LugIEFGH and the *S. aureus* N315 wild type: $MIC_{(S.\ aureus\ LugIEFGH)}/MIC_{(S.\ aureus\ WT)}$. From the results it can be derived that lugdunin, but neither I.1 nor CCCP, is recognized and transported by the transporters.

The results are shown in FIG. 5. Shown is the ratio of the MIC of the three compounds for the *S. aureus* strain with the ABC transporter genes LugIEFGH and the *S. aureus* wild type: $MIC_{(S.\ aureus\ LugIEFGH)}/MIC_{(S.\ aureus\ Wt)}$. For example, for lugdunin this results in [$MIC_{(S.\ aureus\ LugIEFGH)}$: $MIC_{(S.\ aureus\ Wt)}$]=33.7 μg/mL:8.15 μg/mL (respectively, approximately 10 μM:41 μM). While the MIC ratio for lugdunine is median 4.36, compound I.1 according to the invention has a ratio of 1.064. If the ratio is close to 1, there is no resistance increase by the transporters. This means that for compound I.1 according to the invention no formation of resistance is to be expected, and it indicates that compound I.1 according to the invention is different from lugdunin in terms of the mode of action.

Example 5: Synthesis (SPPS) of Compounds I.19, I.20, I.21, I.22, I.23 and I.24

The cyclic compounds I.19, I.20, I.21, I.22, I.23, and I.24 (see FIGS. 1 B and C) were synthesized by solid-phase peptide synthesis (SPPS) as described in Example 2. These compounds were then screened for possible bactericidal activity as described in Example 3 A. Furthermore, the compounds were analyzed by coupled HPLC mass spectrometry and $^1$H-NMR as described in Examples 3 B and 3 C. The results of the bactericidal activity measurement are shown in FIG. 2 B. The results of the mass spectrometry analysis of compounds I.19, I.20, I.21, I.22, I.23, and I.24 are shown in FIG. 3 (see FIG. 3 (I)-(T)). The results of the $^{1}H$ NMR analysis of compounds I.19, I.20, I.21, I.22, I.23, and I.24 are shown in FIG. 4 (see FIG. 4 (D)-(I)).

Example 6: Determination of Antiviral Activity Against SARS-CoV-2

To determine SARS-CoV-2 replication, immunostaining for detection of the nucleocapsid (N) protein was used. On day 1, A549 cells were inoculated at a density of $1.5 \times 10^4$ cells per well of a flat-bottomed 96-well plate (Corning). On day 2, SARS-CoV-2 (MOI=1.0) was added to the medium, which further contained either lugdunin or compound ISW 1-2 (I.3). On day 3, plates were fixed with 10% formaldehyde and inactivated by incubation in 6% formaldehyde for 30 minutes. Cells were then washed with PBS, permeabilized with 0.2% Triton X-100 in PBS for 15 minutes, and stained using an N-protein-specific antibody and a labeled secondary antibody. Staining was measured by determining absorbance at 450 nm using a Tecan XFluor4 reader (Wiesbaden, Germany). It was found that compound ISW 1-2 showed virus inhibition of about 80% in A549 cells already at a concentration of 3.7 μM (data not shown). The measured $EC_{50}$ value was 2.225 μM. For lugdunin, the measured $EC_{50}$ value was 19.77 μM (data not shown). Thus, compound ISW1-2 exhibits approximately 9-fold higher antiviral activity than lugdunin.

Example 7: Determination of Cytotoxicity

Figure 6A:
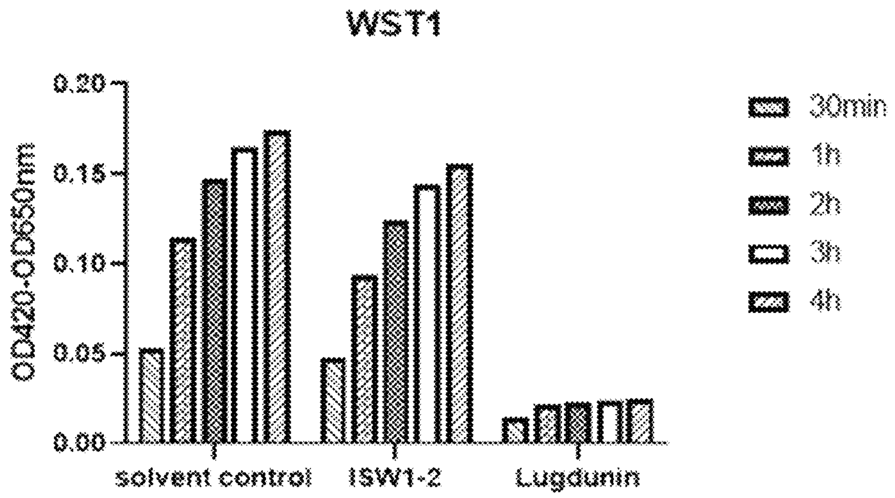
FIG. 6: Cytotoxicity of compound I.3 according to the invention, as well as the known compound lugdunin in primary keratinocytes. (A) Results from the WST1 cell proliferation assay. (B) Results from the lactate dehydrogenase (LDH) assay.
Figure 6B:
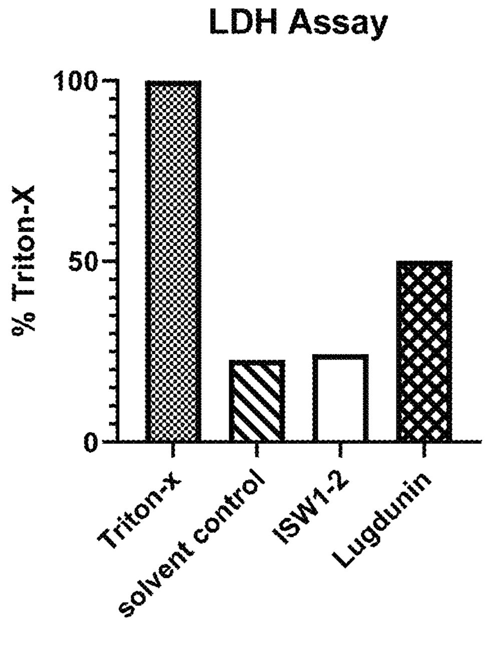

To determine possible cytotoxicity, a WST-1 assay was first performed using human primary keratinocytes from three different donors according to the manufacturer's instructions. The colorimetric assay measures cell viability of cells and can therefore be used to determine cytotoxic compounds incubated with the cells. The greater the number of viable cells, the higher the activity of mitochondrial dehydrogenases and the greater the amount of dye formed in the assay. Keratinocytes were incubated with the cyclic peptide lugdunin (3.1 μg/ml) or the compound ISW1-2 (3.1 μg/ml) for 6 h at 37° C., 5% $CO_2$. Cell culture supernatants were then removed, and WST1 reagent was added to the keratinocytes. The results are shown in FIG. 6 A. Shown in the diagram is the measurement of absorbance to detect mitochondrial activity of the cells at different points in time. DMSO served as a negative control (solvent control). The compound lugdunin showed a measurable cytotoxic effect on primary keratinocytes in the WST-1 assay. Surprisingly, the compound ISW1-2 showed no such cytotoxic effect on keratinocytes, as the measured absorbance values were in the solvent control range.

To verify the results, an LDH assay was performed using human primary keratinocytes from three different donors according to the manufacturer's instructions. This assay is based on the detection of the enzyme lactate dehydrogenase, which is released into the cell culture medium when the cell membrane is damaged, where it can then be detected. Keratinocytes were incubated with the cyclic peptide lugdunin (3.1 μg/ml) or the compound ISW1-2 (3.1 μg/ml) for 24 h at 37° C., 5% $CO_2$. Subsequently, 50 μl of each cell culture supernatant was transferred to a 96 well plate, mixed with 50 μl of LDH reagent and measured (according to manufacturer's instructions). The results are shown in FIG. 6 B. The results were plotted relative to Triton-X treatment (release=100%). DMSO served as a negative control (solvent control). The compound lugdunin also showed a cytotoxic effect on keratinocytes in the LDH assay. Similar to the negative control (solvent control), no significant cytotoxic effect on keratinocytes was measured for the compound ISW1-2, as the content of LDH in the cell culture medium was comparatively low.

The invention claimed is:

1. A cyclic compound of formula (I):

(I)

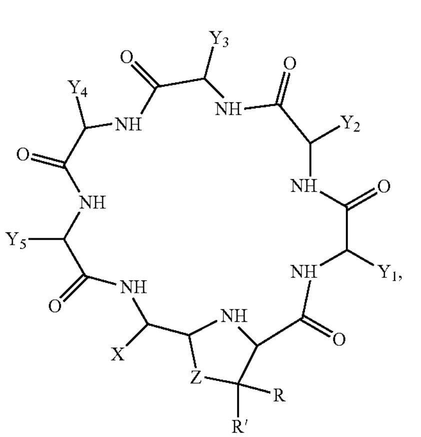

wherein:

X and $Y_1$ to $Y_5$ each represent methyl, ethyl, n-propyl, 2-propenyl ($H_2C{=}CH{-}CH_2{-}$), 1-methylethyl, n-butyl, 2-methylpropyl, 1-methylpropyl, 1,1-dimethylethyl, n-pentyl, 3-methylbutyl, benzyl (Bn), propargyl ($HC{\equiv}C{-}CH_2{-}$), 1H-indole-3-ylmethyl ( 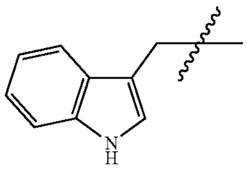 ), 1N-methyl-1H-indole-3-ylmethyl ( 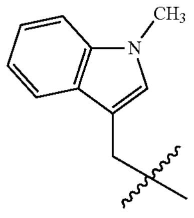 ), 3-benzothienylmethyl ( 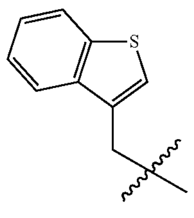 ), 1-naphthylmethyl

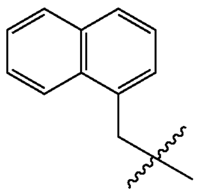

( ), 9-anthracenylmethyl

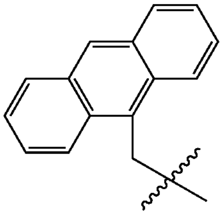

( )

or pyrenylmethyl;

Z equals O or S;

C atoms directly linked to substituents $Y_1$, $Y_2$, $Y_3$, $Y_4$, $Y_5$ and X, in this order, each have an alternating absolute stereochemical configuration; and the C atom linked to substituent X and the C atom in position 4 of a thiazolidine or oxazolidine ring have the same absolute stereochemical configuration when Z is O and an opposite absolute stereochemical configuration when Z is S;

R, R', X, $Y_2$ and $Y_5$ being combined as follows:

(i) R and R' are both methyl; $Y_2$ is 1H-indole-3-ylmethyl or pyrenylmethyl, if $Y_5$ is 1-methylethyl, or $Y_2$ is 1-methylethyl if $Y_5$ is 1H-indole-3-ylmethyl or pyrenylmethyl; and X represents 1-methylethyl; or (ii) R is H; R' is methyl, ethyl, n-propyl, 1-methylethyl, benzyl or propargyl; $Y_2$ is 1H-indole-3-ylmethyl or pyrenylmethyl, if $Y_5$ is 1-methylethyl, or $Y_2$ is 1-methylethyl, if $Y_5$ is 1H-indole-3-ylmethyl or pyrenylmethyl; and X is 1-methylethyl; or (iii) R is H; R' is methyl, n-propyl, 1-methylethyl, benzyl or propargyl; $Y_2$ is 1H-indole-3-ylmethyl or pyrenylmethyl, if $Y_5$ is 1-methylethyl, or $Y_2$ is 1-methylethyl if $Y_5$ is 1H-indole-3-ylmethyl or pyrenylmethyl; and X is 1-methylethyl or 2-methylpropyl; or (iv) R and R' are both 1-methylethyl; and $Y_2$ is 1H-indole-3-ylmethyl;

with the proviso that when X, $Y_1$, $Y_4$ and $Y_5$ are 1-methylethyl, $Y_2$ is 1H-indole-3-ylmethyl, $Y_3$ is 2-methylpropyl, R is H and R' is methyl, Z is not O;

or salts thereof, solvates thereof, and solvates of salts thereof.

2. The cyclic compound of claim 1, wherein (i) applies.

3. The cyclic compound of claim 1, wherein (ii) applies.

4. The cyclic compound of claim 1, wherein (iii) applies.

5. The cyclic compound of claim 1, wherein (iv) applies.

6. The cyclic compound of claim 1, wherein the compound has one of the following formulae:

I.1

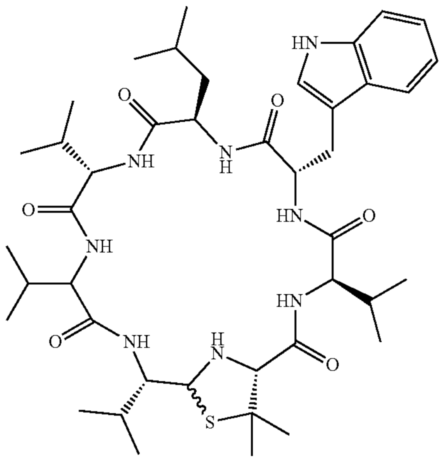

I.2

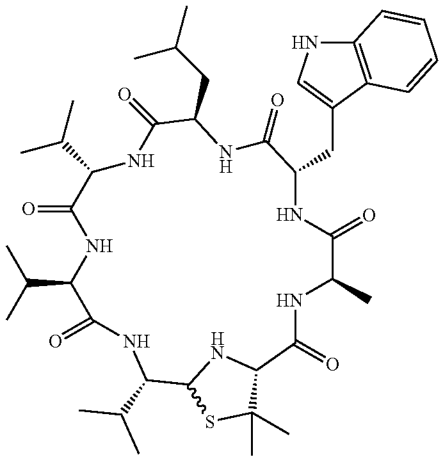

I.3

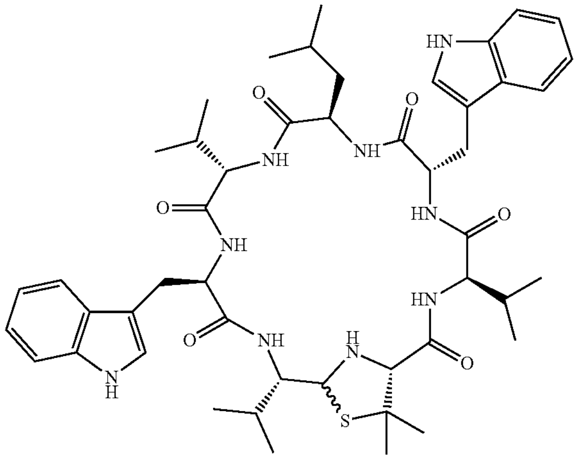

-continued
I.4
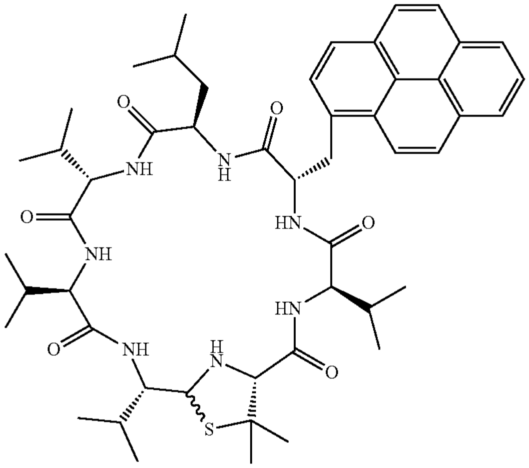
I.5
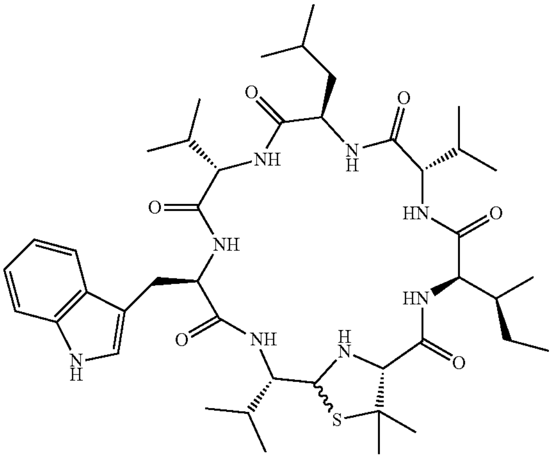
I.6
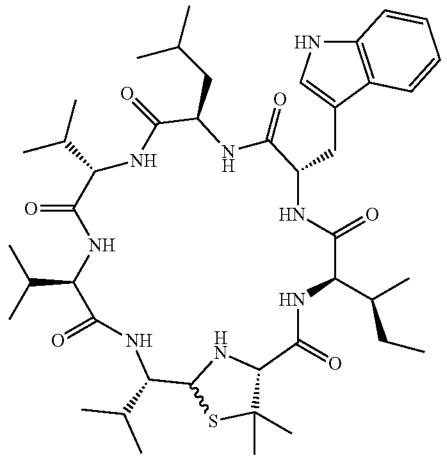
-continued
I.7
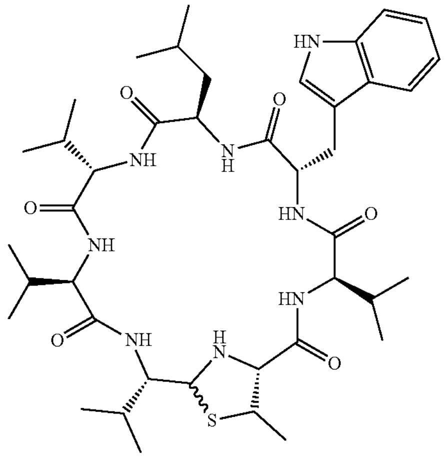
I.8
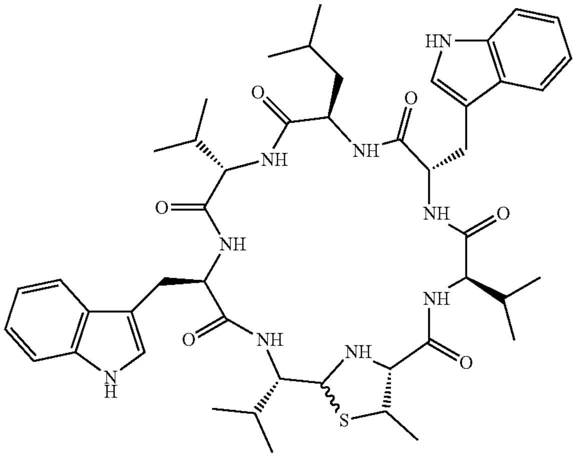
I.9
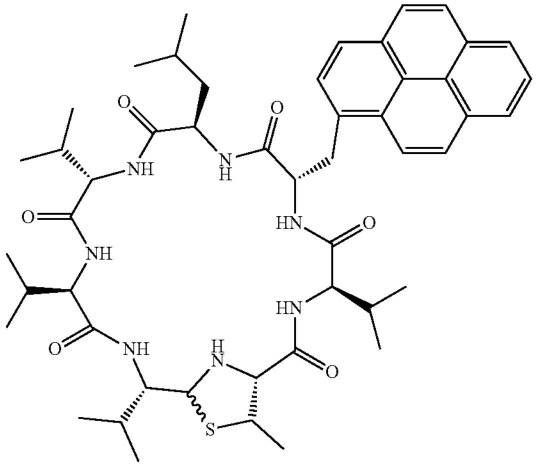

-continued
I.10
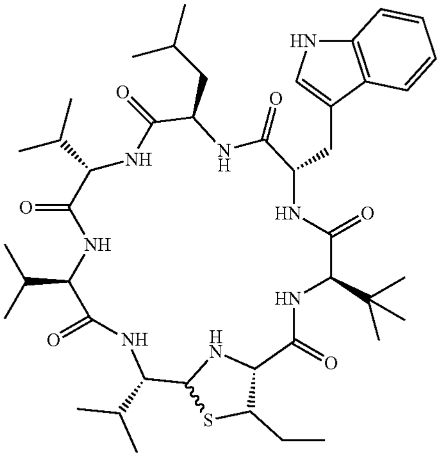
I.11
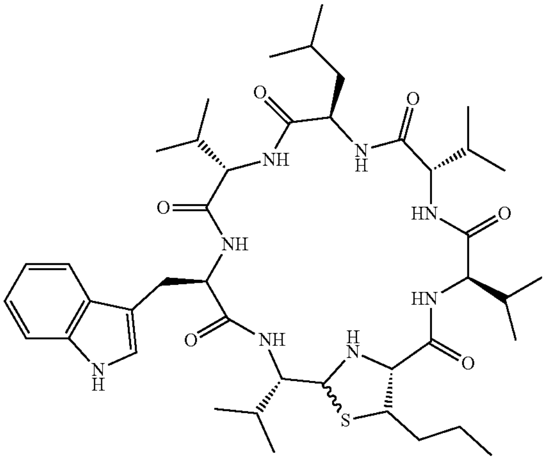
I.12
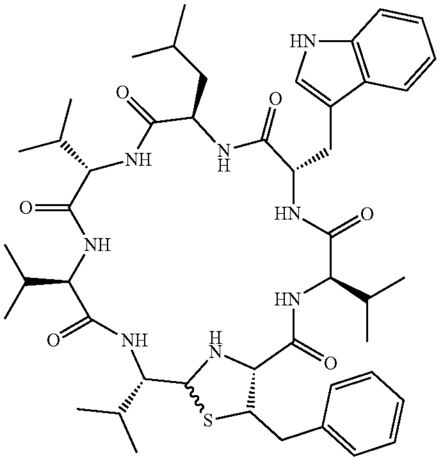
-continued
I.13
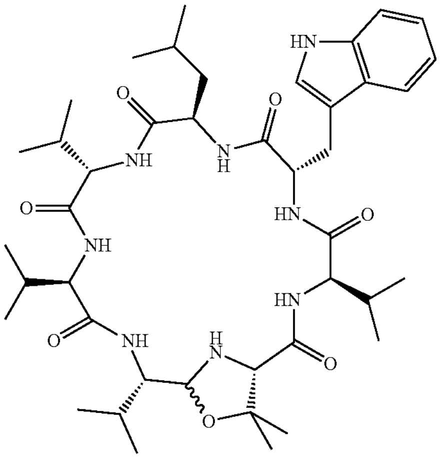
I.14
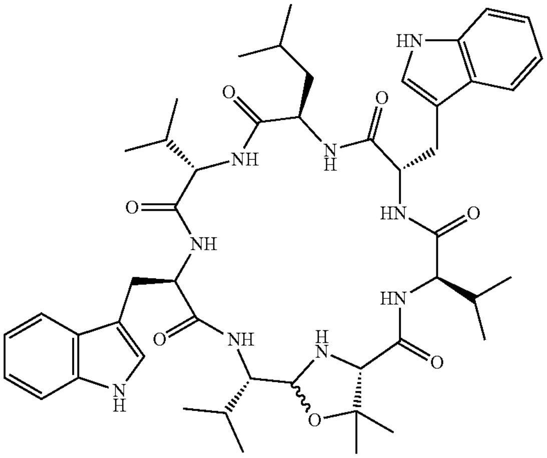
I.15
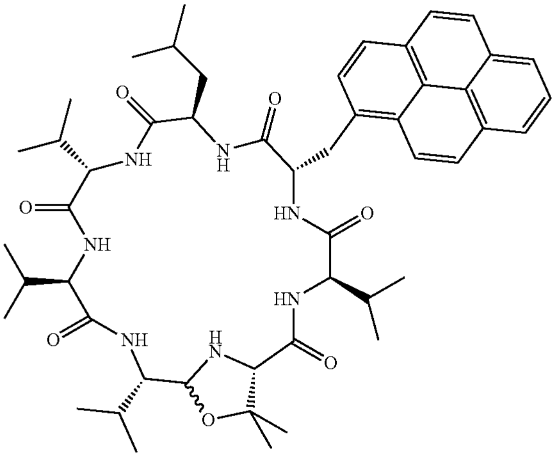

-continued
I.16
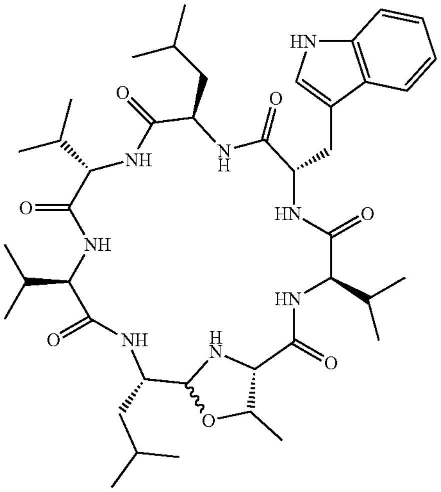
I.17
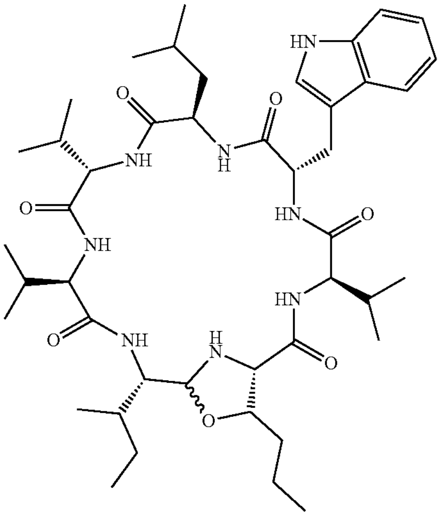
I.18
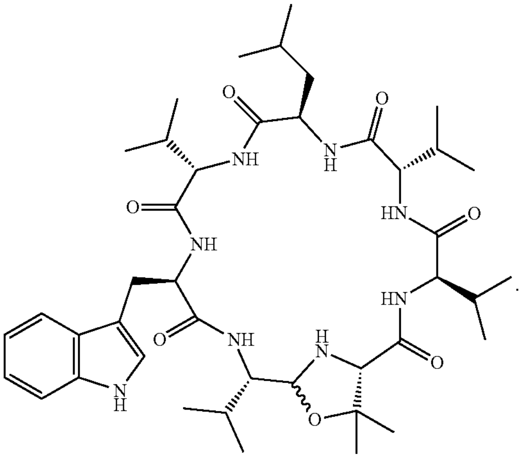
.
-continued
I.19
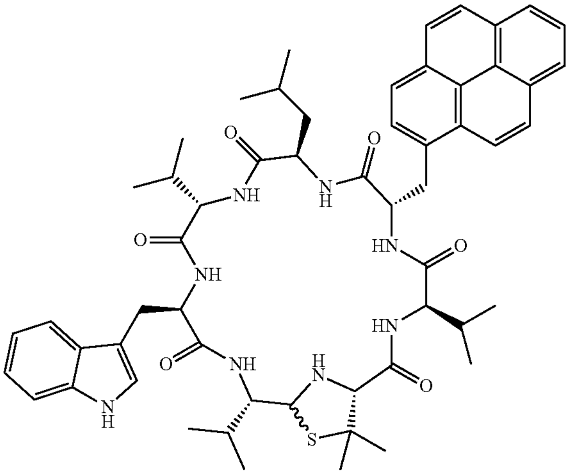
I.20
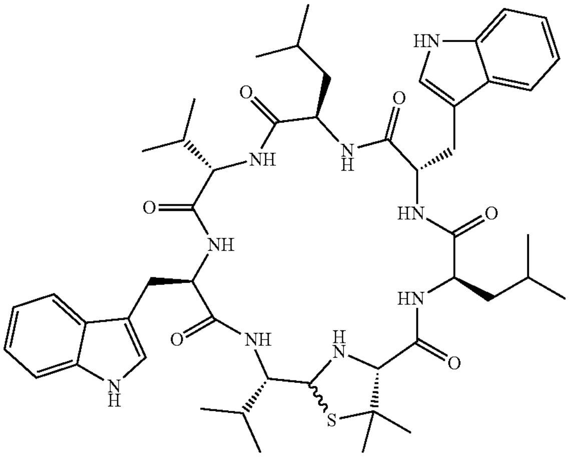
I.21
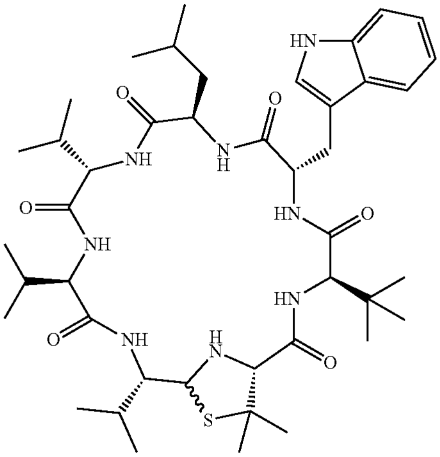

-continued
I.22
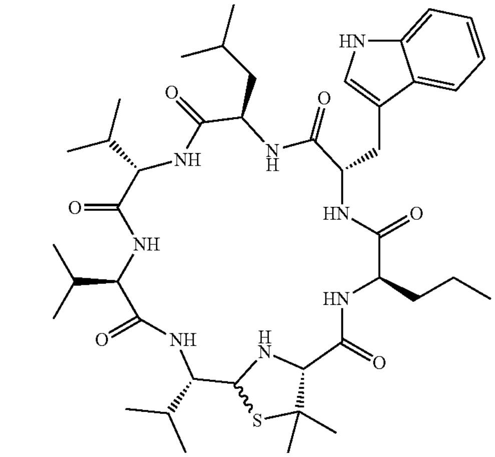
I.23
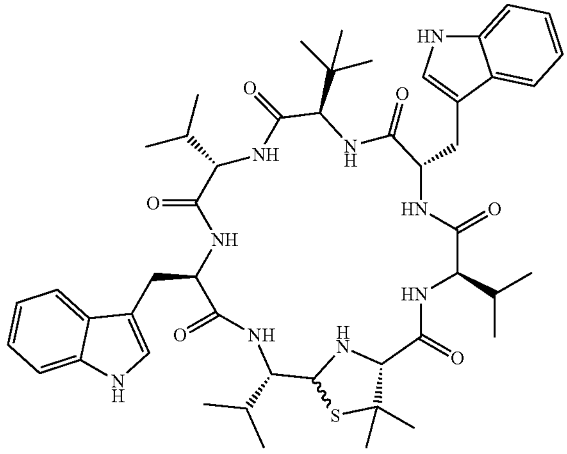
I.24
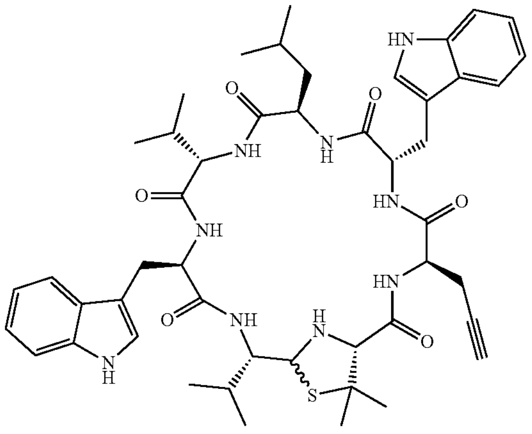
.
7. The cyclic compound of claim 1, wherein the compound exhibits antimicrobial activity and/or a supportive effect on innate immune response.
8. A thiazolidine or oxazolidine building block, wherein the building block has one of the following formulae
(II.1)
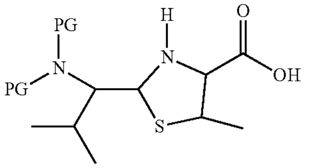
(II.2)
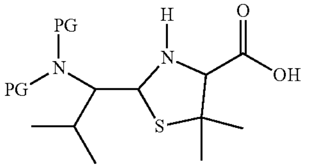
(II.3)
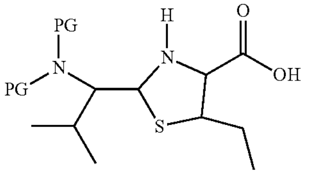
(II.4)
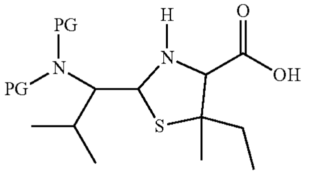
(II.5)
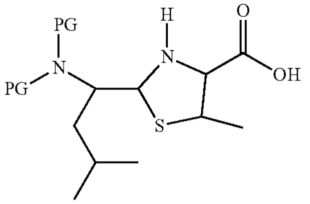
(II.6)
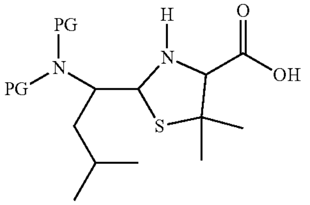
(II.7)
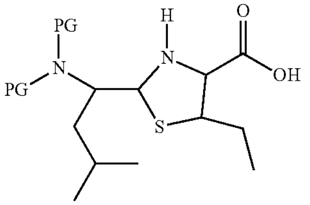
(II.8)
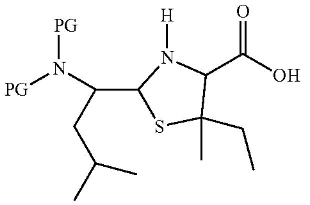

-continued
(II.9)
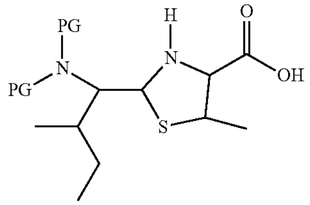
(II.10)
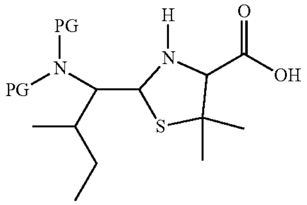
(II.11)
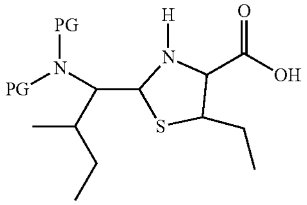
(II.12)
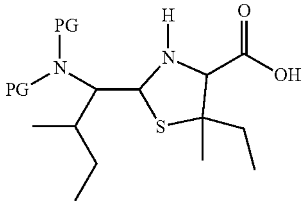
(II.13)
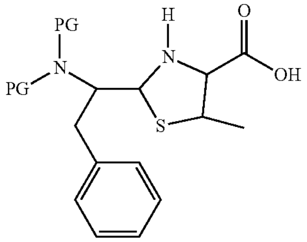
(II.14)
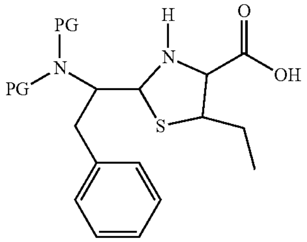
(II.15)
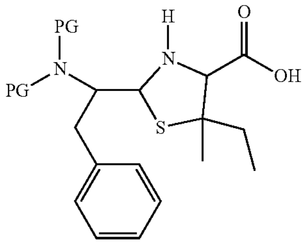
-continued
(II.16)
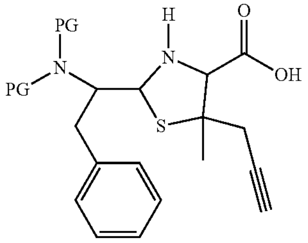
(II.17)
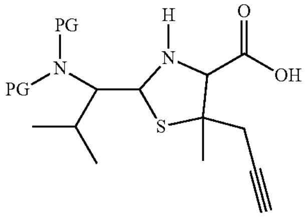
(II.18)
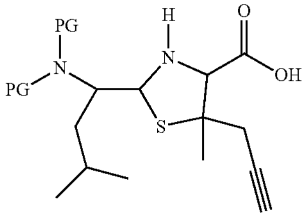
(II.19)
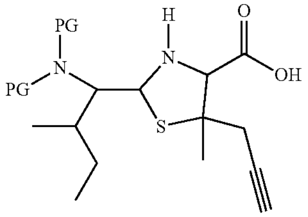
(II.20)
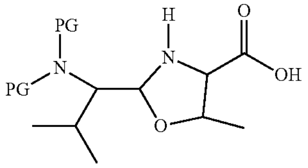
(II.21)
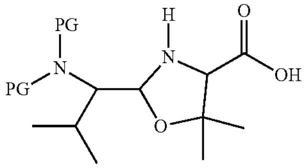
(II.22)
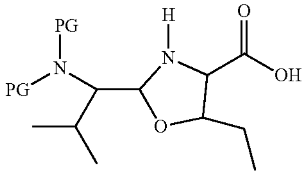

-continued
(II.23)
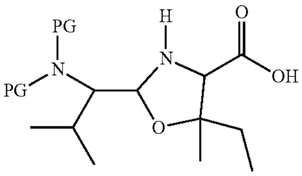
(II.24)
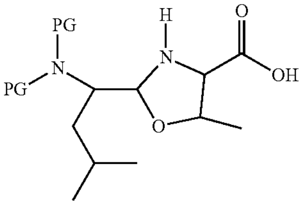
(II.25)
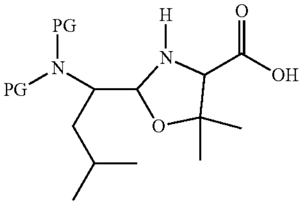
(II.26)
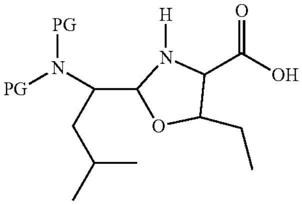
(II.27)
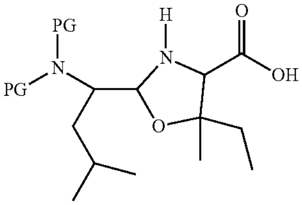
(II.28)
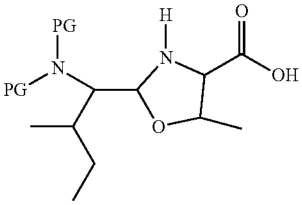
(II.29)
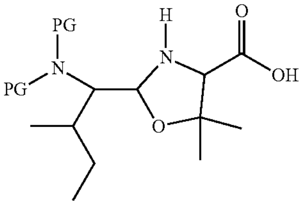
-continued
(II.30)
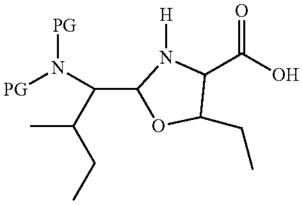
(II.31)
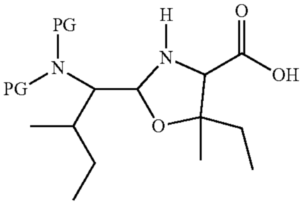
(II.32)
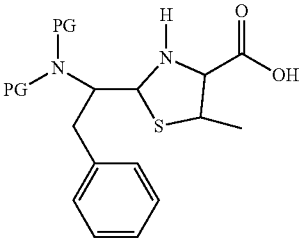
(II.33)
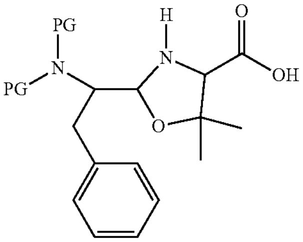
(II.34)
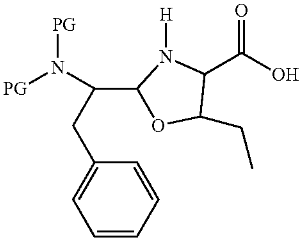
(II.35)
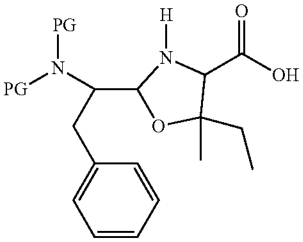

-continued (II.36)

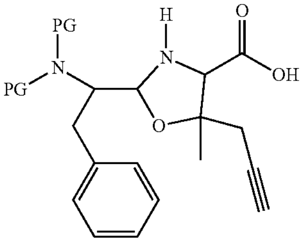

(II.37)

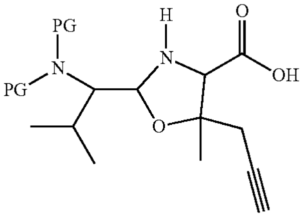

(II.38)

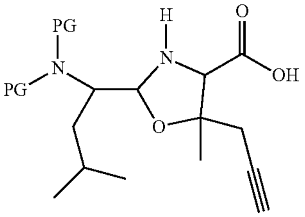

(II.39)

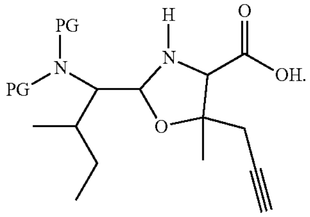

9. A cosmetic preparation, wherein the preparation is in the form of a dermatological preparation for topical application and comprises one or more cyclic compounds of claim 1; and one or more cosmetically acceptable carriers.

10. The preparation of claim 9, wherein the one or more cyclic compounds exhibit an antimicrobial activity and/or exhibit a supportive effect on an innate immune response.

11. The preparation of claim 9, wherein the preparation comprises (a) a cyclic compound of the following formula:

I.3

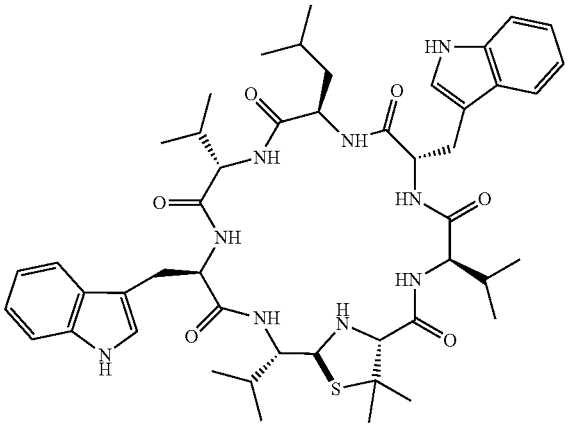

(b) one or more cosmetically acceptable carriers.

* * * * *